US010667835B2

(12) United States Patent
Weisenburgh, II et al.

(10) Patent No.: US 10,667,835 B2
(45) Date of Patent: *Jun. 2, 2020

(54) ULTRASONIC SURGICAL INSTRUMENT WITH END EFFECTOR HAVING RESTRICTED ARTICULATION

(71) Applicant: Ethicon LLC, Guaynabo, PR (US)

(72) Inventors: William B. Weisenburgh, II, Maineville, OH (US); Barry C. Worrell, Centerville, OH (US); David A. Monroe, Milford, OH (US); Jeffrey L. Aldridge, Lebanon, OH (US); Benjamin D. Dickerson, Cincinnati, OH (US); Craig N. Faller, Batavia, OH (US); William D. Fox, New Richmond, OH (US); Michael J. Stokes, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 777 days.

This patent is subject to a terminal disclaimer.

(21) Appl. No.: 14/688,692

(22) Filed: Apr. 16, 2015

(65) Prior Publication Data
US 2015/0320438 A1    Nov. 12, 2015

Related U.S. Application Data

(60) Provisional application No. 62/176,880, filed on Apr. 22, 2014.

(51) Int. Cl.
*A61B 17/32* (2006.01)
*A61N 7/00* (2006.01)
(Continued)

(52) U.S. Cl.
CPC ........ *A61B 17/320016* (2013.01); *A61N 7/00* (2013.01); *A61B 2017/22018* (2013.01);
(Continued)

(58) Field of Classification Search
CPC .... A61B 17/320092; A61B 17/320068; A61B 2017/00327; A61B 2017/320072;
(Continued)

(56) References Cited

U.S. PATENT DOCUMENTS 2,906,143 A    9/1959   Walton
5,322,055 A    6/1994   Davison et al.
(Continued)

FOREIGN PATENT DOCUMENTS

CN    103281979 A    9/2013
EP      2668911 A2   12/2013
(Continued)

OTHER PUBLICATIONS

U.S. Appl. No. 14/258,179, filed Apr. 22, 2014.
(Continued)

*Primary Examiner* — Katherine Houston
*Assistant Examiner* — Michael G Mendoza
(74) *Attorney, Agent, or Firm* — Frost Brown Todd LLC

(57) ABSTRACT

An apparatus comprises a body assembly, a shaft, an acoustic waveguide, an articulation section, an end effector, and an articulation drive assembly. The shaft extends distally from the body assembly and defines a longitudinal axis. The acoustic waveguide comprises a flexible portion. The articulation section is coupled with the shaft. A portion of the articulation section encompasses the flexible portion of the waveguide. The articulation section comprises a plurality of body portions aligned along the longitudinal axis and a flexible locking member. The flexible locking member is operable to secure the body portions in relation to each other and in relation to the shaft. The end effector comprises an ultrasonic blade in acoustic communication with the waveguide. The articulation drive assembly is operable to drive
(Continued)

articulation of the articulation section to thereby deflect the end effector from the longitudinal axis.

18 Claims, 75 Drawing Sheets

(51) Int. Cl.
*A61B 18/00* (2006.01)
*A61B 17/29* (2006.01)
*A61B 17/22* (2006.01)

(52) U.S. Cl.
CPC .............. *A61B 2017/2929* (2013.01); *A61B 2017/2932* (2013.01); *A61B 2017/320069* (2017.08); *A61B 2017/320071* (2017.08); *A61B 2017/320089* (2017.08); *A61B 2017/320094* (2017.08); *A61B 2017/320095* (2017.08); *A61B 2018/0063* (2013.01)

(58) Field of Classification Search
CPC .. A61B 2017/2908; A61B 2017/00318; A61B 2017/00314
See application file for complete search history.

(56) References Cited

U.S. PATENT DOCUMENTS

| | | | |
|---|---|---|---|
| 5,873,873 A | 2/1999 | Smith et al. | |
| 5,897,523 A * | 4/1999 | Wright | A61B 17/32006 600/459 |
| 5,980,510 A | 11/1999 | Tsonton et al. | |
| 5,989,264 A | 11/1999 | Wright | |
| 6,063,098 A * | 5/2000 | Houser | A61B 17/22012 606/169 |
| 6,090,120 A | 7/2000 | Wright et al. | |
| 6,325,811 B1 | 12/2001 | Messerly | |
| 6,454,782 B1 | 9/2002 | Schwemberger | |
| 6,500,176 B1 | 12/2002 | Truckai et al. | |
| 6,589,200 B1 | 7/2003 | Schwemberger et al. | |
| 6,752,815 B2 | 6/2004 | Beaupre | |
| 6,773,444 B2 | 8/2004 | Messerly | |
| 6,783,524 B2 | 8/2004 | Anderson et al. | |
| 7,112,201 B2 | 9/2006 | Truckai et al. | |
| 7,125,409 B2 | 10/2006 | Truckai et al. | |
| 7,135,030 B2 | 11/2006 | Schwemberger et al. | |
| 7,169,146 B2 | 1/2007 | Truckai et al. | |
| 7,186,253 B2 | 3/2007 | Truckai et al. | |
| 7,189,233 B2 | 3/2007 | Truckai et al. | |
| 7,220,951 B2 | 5/2007 | Truckai et al. | |
| 7,309,849 B2 | 12/2007 | Truckai et al. | |
| 7,311,709 B2 | 12/2007 | Truckai et al. | |
| 7,354,440 B2 | 4/2008 | Truckai et al. | |
| 7,381,209 B2 | 6/2008 | Truckai et al. | |
| 7,621,930 B2 | 11/2009 | Houser | |
| 8,461,744 B2 | 6/2013 | Wiener et al. | |
| 8,591,536 B2 | 11/2013 | Robertson | |
| 8,623,027 B2 | 1/2014 | Price et al. | |
| 8,888,809 B2 | 11/2014 | Davison et al. | |
| 8,939,974 B2 | 1/2015 | Boudreaux et al. | |
| 8,986,302 B2 | 3/2015 | Aldridge et al. | |
| 9,089,327 B2 | 7/2015 | Worrell et al. | |
| 9,161,803 B2 | 10/2015 | Yates et al. | |
| 2003/0191494 A1* | 10/2003 | Gray | A61B 17/122 606/205 |
| 2006/0079874 A1 | 4/2006 | Faller et al. | |
| 2007/0191713 A1 | 8/2007 | Eichmann et al. | |
| 2007/0282333 A1 | 12/2007 | Fortson et al. | |
| 2008/0200940 A1 | 8/2008 | Eichmann et al. | |
| 2010/0069940 A1 | 3/2010 | Miller et al. | |
| 2012/0078243 A1 | 3/2012 | Worrell et al. | |
| 2012/0078244 A1 | 3/2012 | Worrell et al. | |
| 2012/0078247 A1 | 3/2012 | Worrell et al. | |
| 2012/0078248 A1 | 3/2012 | Worrell et al. | |
| 2012/0112687 A1 | 5/2012 | Houser et al. | |
| 2012/0116265 A1 | 5/2012 | Houser et al. | |
| 2013/0023868 A1 | 1/2013 | Worrell et al. | |
| 2013/0289592 A1 | 10/2013 | Stulen et al. | |
| 2014/0005677 A1 | 1/2014 | Shelton et al. | |
| 2014/0005701 A1 | 1/2014 | Olson et al. | |
| 2014/0005703 A1 | 1/2014 | Stulen et al. | |
| 2014/0114334 A1 | 4/2014 | Olson et al. | |
| 2015/0066022 A1* | 3/2015 | Shelton, IV | A61B 18/082 606/41 |
| 2015/0080924 A1 | 3/2015 | Stulen et al. | |
| 2015/0245850 A1 | 9/2015 | Hibner et al. | |
| 2016/0302812 A1 | 10/2016 | Monroe et al. | |
| 2016/0302817 A1 | 10/2016 | Worrell et al. | |
| 2016/0302818 A1 | 10/2016 | Weisenburgh et al. | |
| 2016/0302819 A1 | 10/2016 | Stulen et al. | |
| 2016/0302820 A1 | 10/2016 | Hibner et al. | |
| 2016/0302840 A1 | 10/2016 | Scheib et al. | |
| 2016/0303403 A1 | 10/2016 | Shapiro et al. | |

FOREIGN PATENT DOCUMENTS

| | | | |
|---|---|---|---|
| JP | H10-262983 A | 10/1998 | |
| JP | 2002-017663 A | 1/2002 | |
| WO | WO 2012/088167 A2 | 6/2012 | |
| WO | WO 2014/004117 A2 | 1/2014 | |

OTHER PUBLICATIONS

U.S. Appl. No. 14/688,684, filed Apr. 16, 2015.
U.S. Appl. No. 61/410,603, filed Nov. 5, 2010.
U.S. Appl. No. 62/176,880, filed Apr. 22, 2014.
International Search Report and Written Opinion dated Jun. 5, 5015 re Application No. PCT/US2015/026322.
Australian Office Action dated Feb. 18, 2019 for Application No. 2015250102, 3 pages.
Chinese Office Action dated Nov. 8, 2018 for Application No. 201580033609.1, 2 pages.
Chinese Search Report dated Jan. 8, 2019 for Application No. 201580033609.1, 1 page.
Chinese Office Action dated Jul. 16, 2019 for Application No. 201580033609.1, 2 pages.
Japanese Notification of Reasons for Refusal dated Mar. 19, 2019 for Application No. 2016-564091, 5 pages.

* cited by examiner

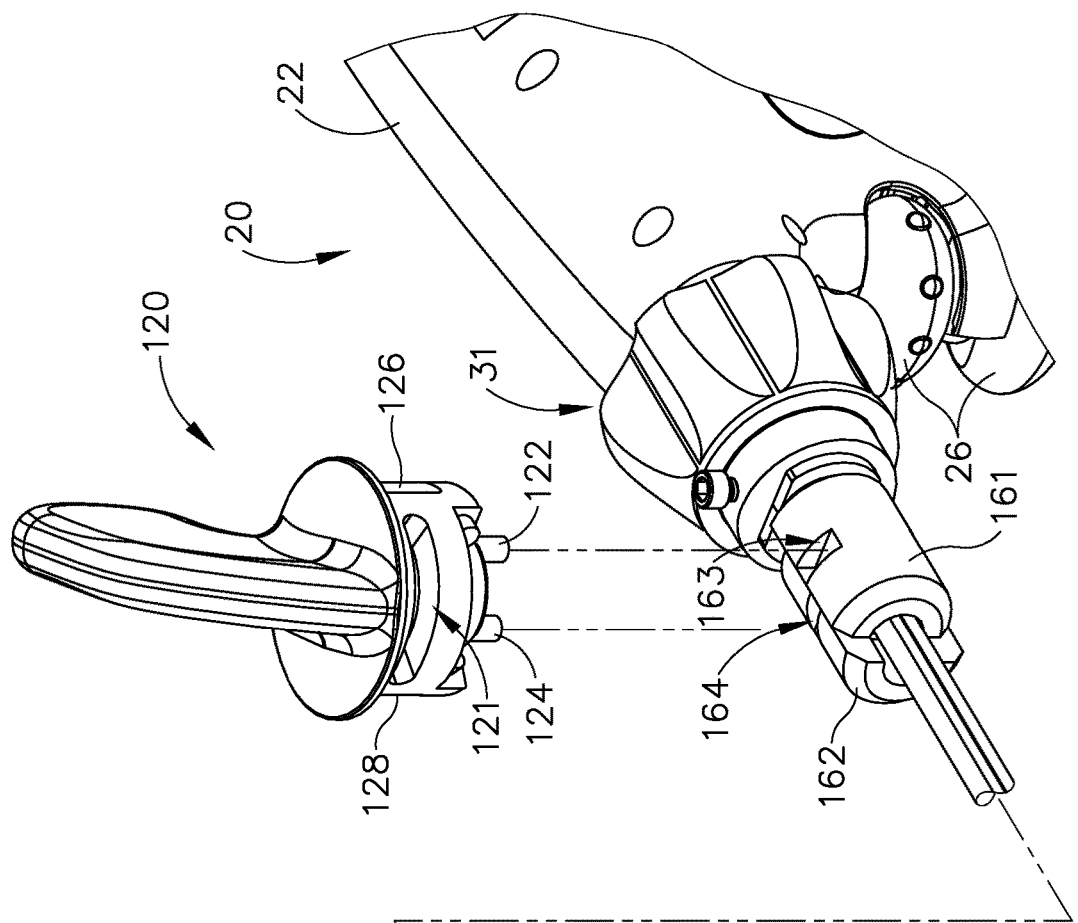
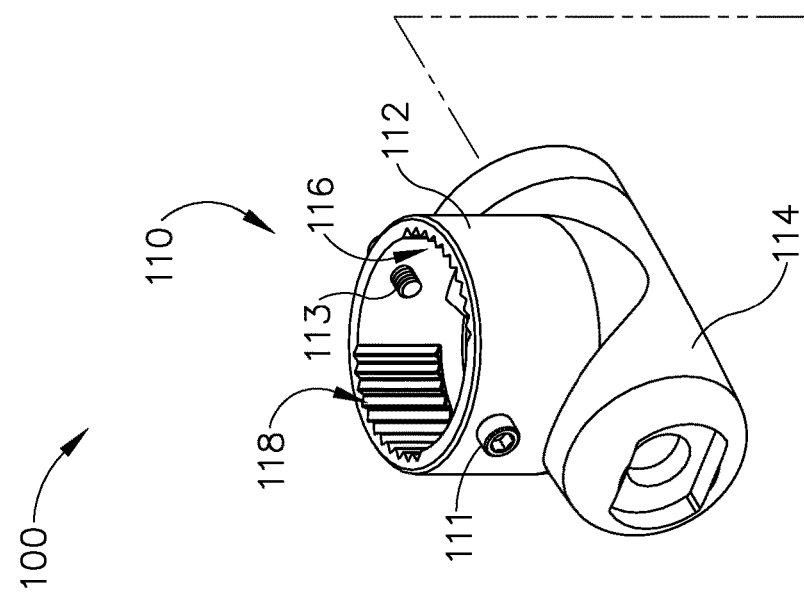
Fig. 9

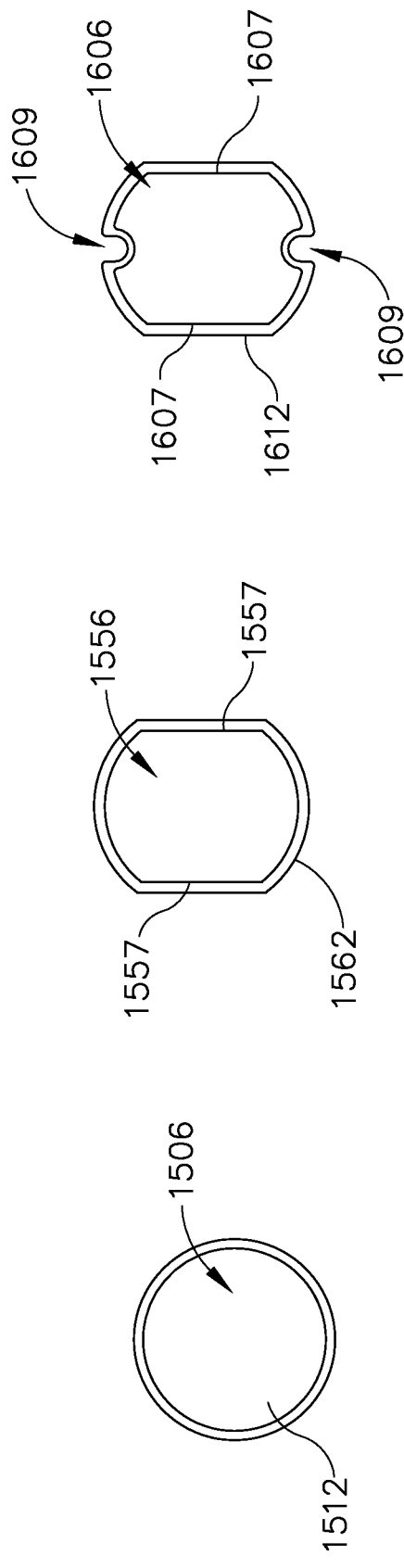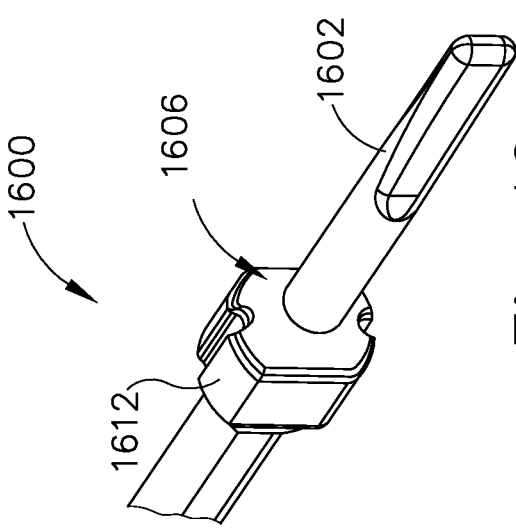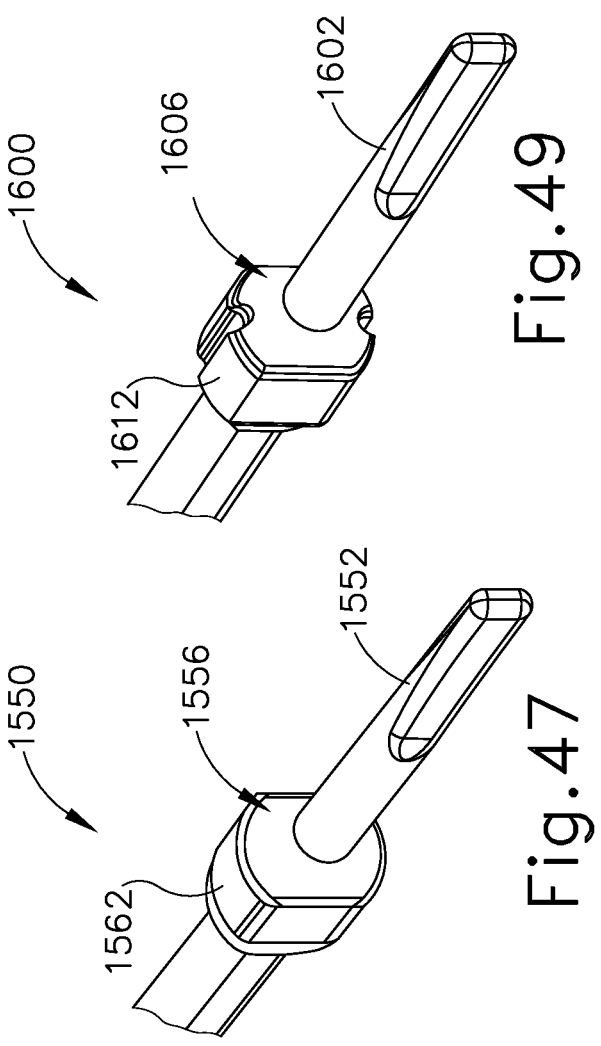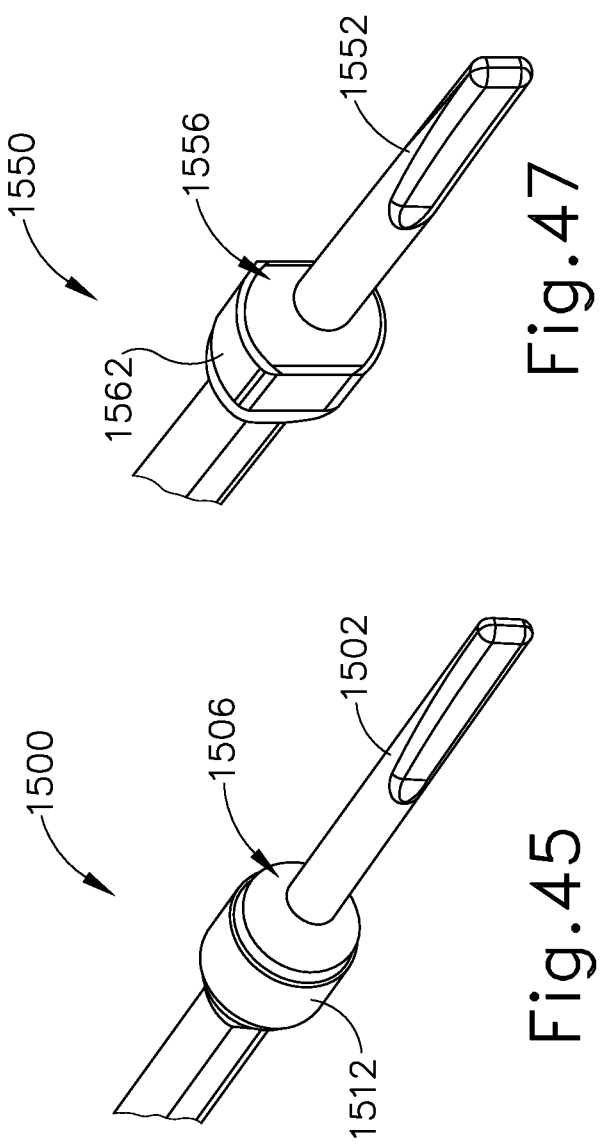

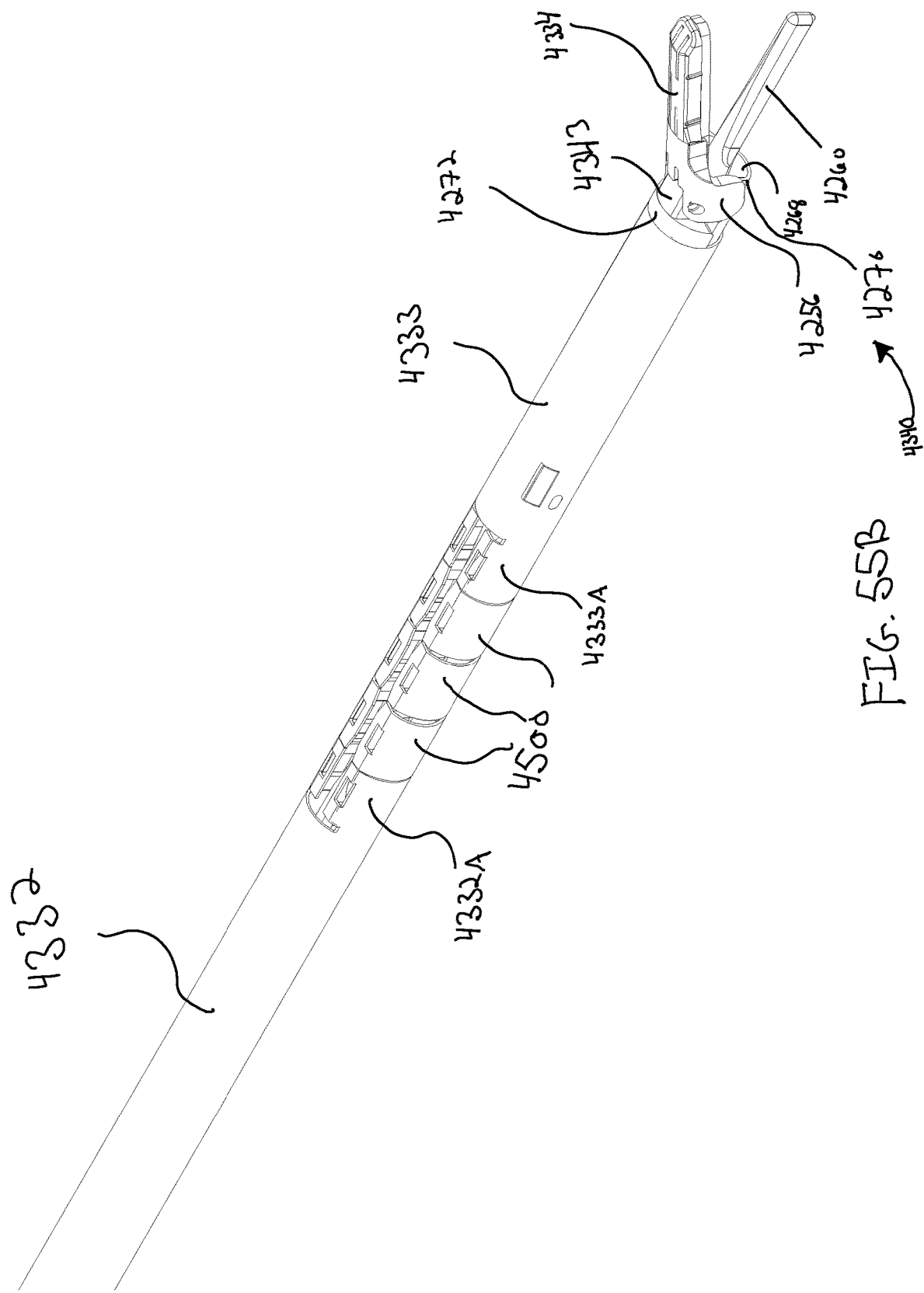

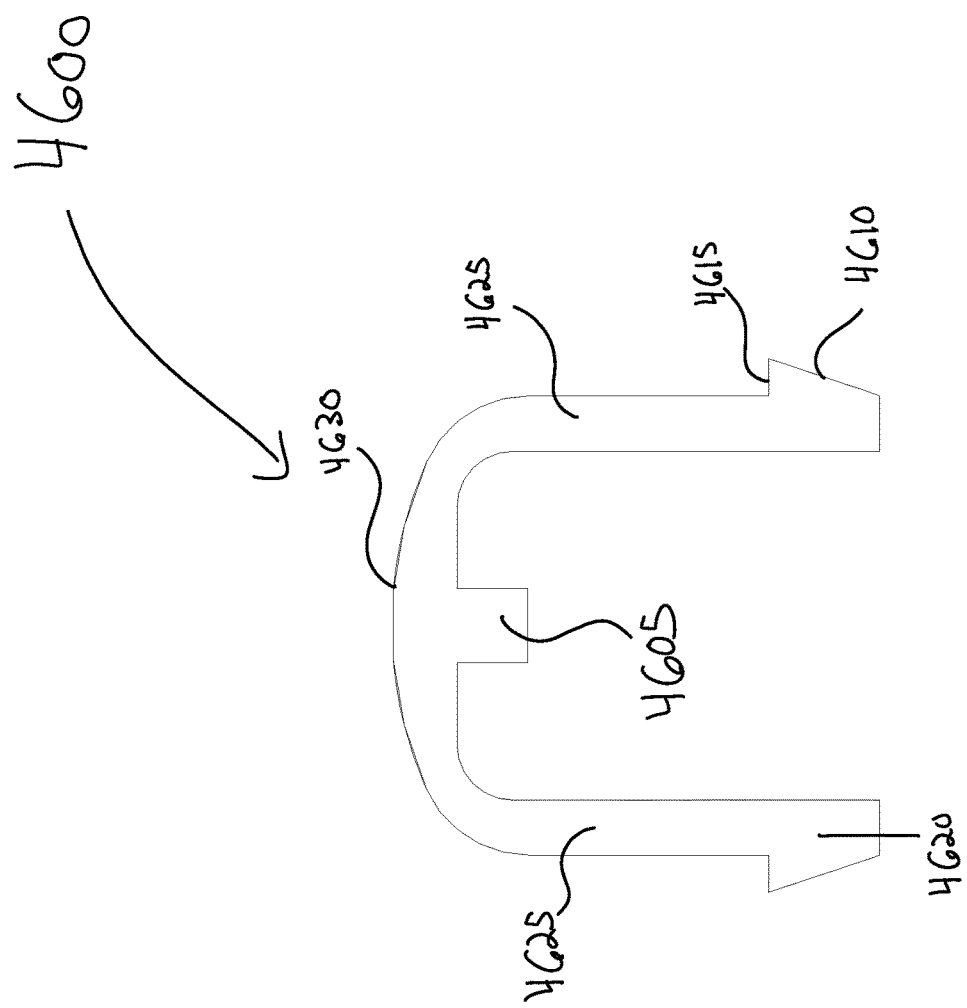

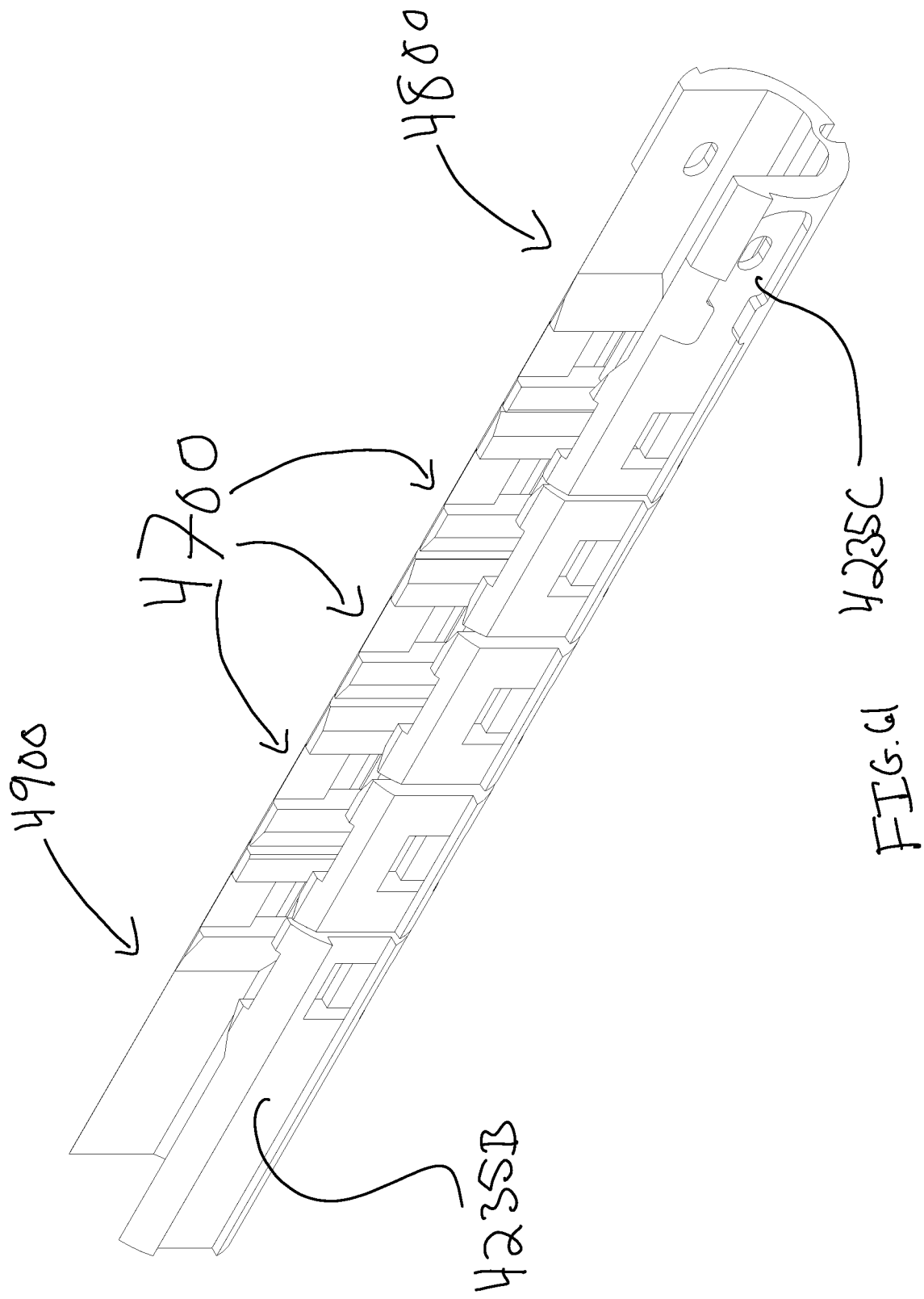

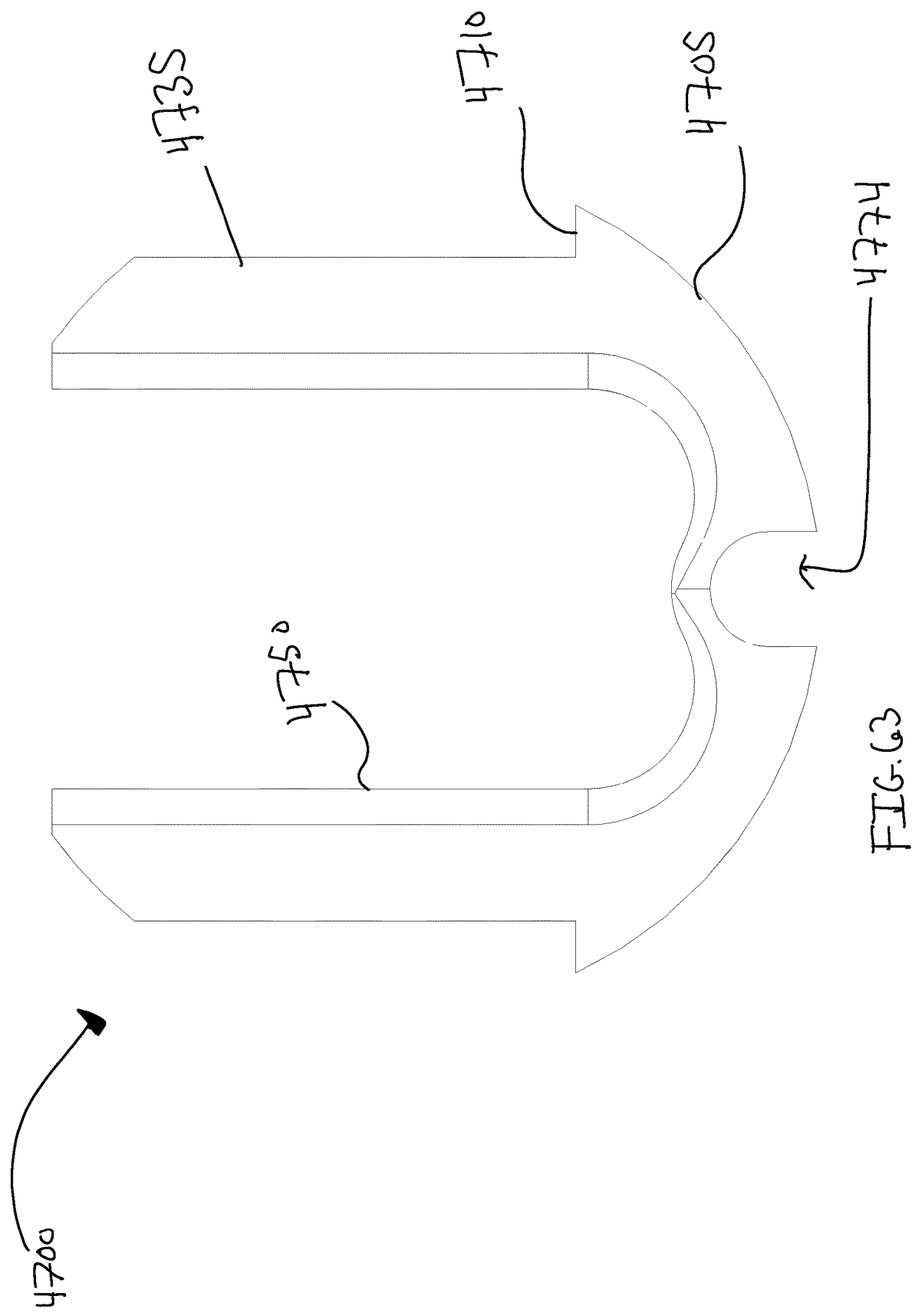

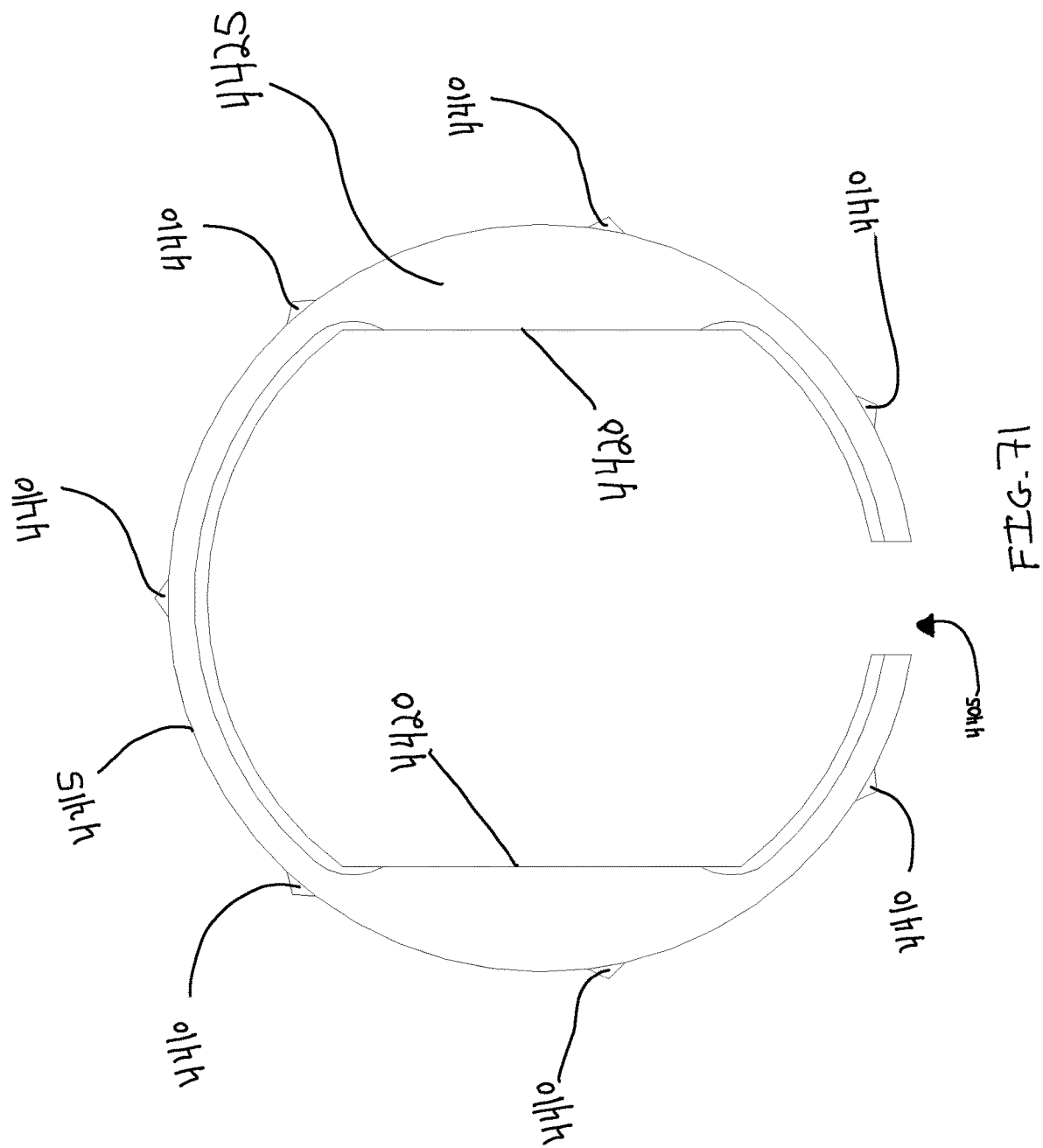

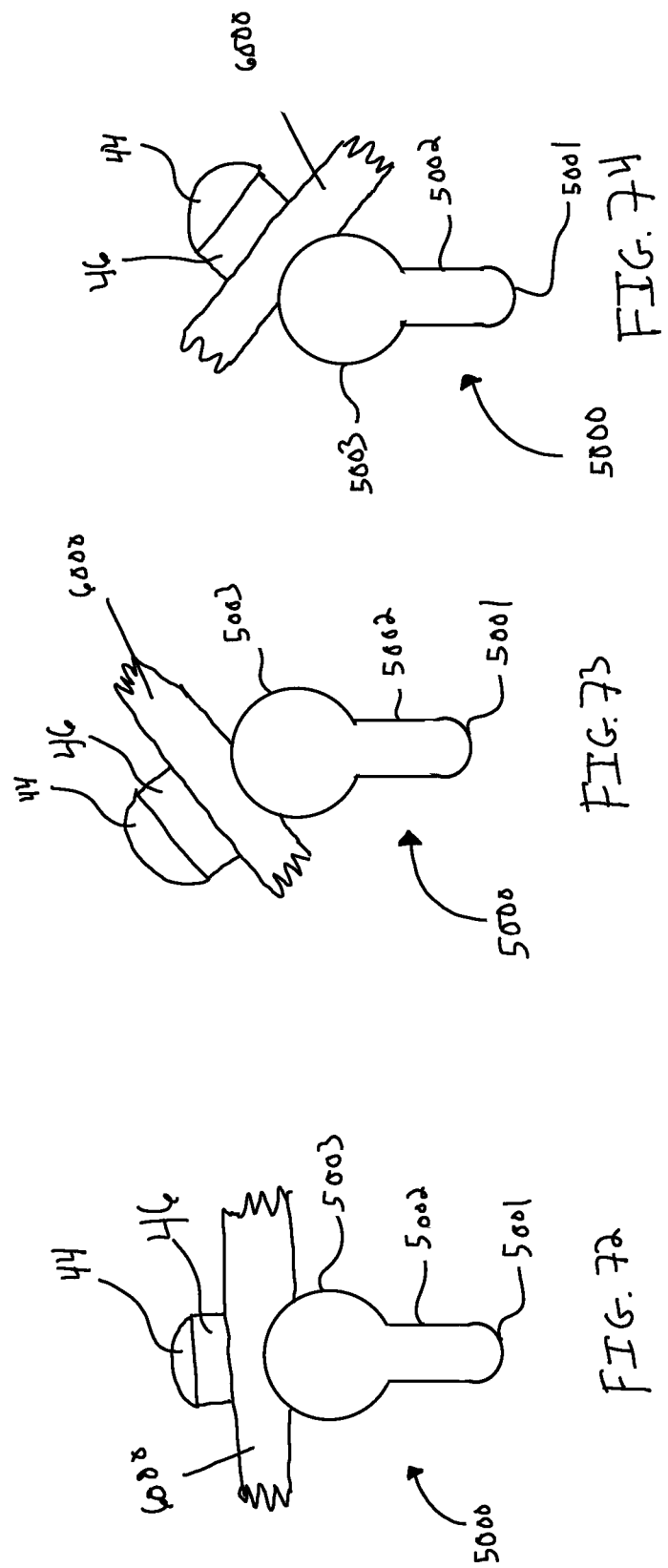

of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; and U.S. Pat. No. 6,783,524, entitled "Robotic Surgical Tool with Ultrasound Cauterizing and Cutting Instrument," issued Aug. 31, 2004, the disclosure of which is incorporated by reference herein.

ULTRASONIC SURGICAL INSTRUMENT WITH END EFFECTOR HAVING RESTRICTED ARTICULATION

PRIORITY

This application claims priority to U.S. Provisional Pat. App. No. 62/176,880, entitled "Ultrasonic Surgical Device with Articulating End Effector," filed Apr. 22, 2014, the disclosure of which is incorporated by reference herein.

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; and U.S. Pat. No. 6,783,524, entitled "Robotic Surgical Tool with Ultrasound Cauterizing and Cutting Instrument," issued Aug. 31, 2004, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pat. No. 8,623,027, entitled "Ergonomic Surgical Instruments," issued Jan. 7, 2014, the disclosure of which is incorporated by reference herein; U.S. Pub. No. 2010/0069940, entitled "Ultrasonic Device for Fingertip Control," published Mar. 18, 2010, issued as U.S. Pat. No. 9,023,071 on May 5, 2015, the disclosure of which is incorporated by reference herein; and U.S. Pat. No. 8,461,744, entitled "Rotating Transducer Mount for Ultrasonic Surgical Instruments," published Jan. 20, 2011, the disclosure of which is incorporated by reference herein; and U.S. Pat. No. 8,591,536, entitled "Ultrasonic Surgical Instrument Blades," published Feb. 2, 2012, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, issued as U.S. Pat. No. 9,381,058 on Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section and/or a bendable ultrasonic waveguide. Examples of such ultrasonic surgical instruments are disclosed in U.S. Pat. No. 5,897,523, entitled "Articulating Ultrasonic Surgical Instrument," issued Apr. 27, 1999, the disclosure of which is incorporated by reference herein; U.S. Pat. No. 5,989,264, entitled "Ultrasonic Polyp Snare," issued Nov. 23, 1999, the disclosure of which is incorporated by reference herein; U.S. Pat. No. 6,063,098, entitled "Articulable Ultrasonic Surgical Apparatus," issued May 16, 2000, the disclosure of which is incorporated by reference herein; U.S. Pat. No. 6,090,120, entitled "Articulating Ultrasonic Surgical Instrument," issued Jul. 18, 2000, the disclosure of which is incorporated by reference herein; U.S. Pat. No. 6,454,782, entitled "Actuation Mechanism for Surgical Instruments," issued Sep. 24, 2002, the disclosure of which is incorporated by reference herein; U.S. Pat. No. 6,589,200, entitled "Articulating Ultrasonic Surgical Shears," issued Jul. 8, 2003, the disclosure of which is incorporated by reference herein; U.S. Pat. No. 6,752,815, entitled "Method and Waveguides for Changing the Direction of Longitudinal Vibrations," issued Jun. 22, 2004, the disclosure of which is incorporated by reference herein; U.S. Pat. No. 7,135,030, entitled "Articulating Ultrasonic Surgical Shears," issued Nov. 14, 2006; U.S. Pat. No. 7,621,930, entitled "Ultrasound Medical Instrument Having a Medical Ultrasonic Blade," issued Nov. 24, 2009, the disclosure of which is incorporated by reference herein; U.S. Pub. No. 2014/0005701, published Jan. 2, 2014, issued as U.S. Pat. No. 9,393,037 on Jul. 19, 2016, entitled "Surgical Instruments with Articulating Shafts," the disclosure of which is incorporated by reference herein; U.S. Pub. No. 2014/0005703, entitled "Surgical Instruments with Articulating Shafts," published Jan. 2, 2014, issued as U.S. Pat. No. 9,408,622 on Aug. 9, 2016, the disclosure of which is incorporated by reference herein; U.S. Pub. No. 2014/0114334, entitled "Flexible Harmonic Waveguides/Blades for Surgical Instruments," published Apr. 24, 2014, issued as U.S. Pat. No. 9,095,367 on Aug. 4, 2015, the disclosure of which is incorporated by reference herein; U.S. Pub. No. 2015/0080924, entitled "Articulation Features for Ultrasonic Surgical Instrument," published Mar. 19, 2015, issued as U.S. Pat. No. 10,172,636 on Jan. 8, 2019, the disclosure of which is incorporated by reference herein; and U.S. patent application Ser. No. 14/258,179, entitled Ultrasonic Surgical Device with Articulating End Effector," filed Apr. 22, 2014, now Provisional App. 62/176,880 the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 9 depicts a partially exploded perspective view of an articulation control assembly of the instrument of FIG. 1;

FIG. 45 depicts a detailed perspective view of the flange of FIG. 44;

FIG. 46 depicts a cross-sectional end view of the flange of FIG. 44;

FIG. 47 depicts a detailed perspective view of an exemplary alternative flange;

FIG. 48 depicts a cross-sectional end view of the flange of FIG. 47;

FIG. 49 depicts a detailed perspective view of another exemplary alternative flange;

FIG. 50 depicts a cross-sectional end view of the flange of FIG. 49;

FIG. 55B depicts a perspective view of the articulation section of the shaft assembly and the end effector of FIG. 55A with certain elements omitted to show greater detail;

FIG. 61 depicts a perspective view of body portions of the articulation section of FIG. 55A longitudinally aligned with one another;

FIG. 62 depicts a perspective view of the intermediate body portion of FIG. 55A;

FIG. 63 depicts a front elevational view of the intermediate body portion of FIG. 55A;

FIG. 71 depicts a front elevational view of the distal node bumper of FIG. 70;

FIG. 72 depicts a front elevational view of tissue clamped between an exemplary keyhole blade and clamp arm assembly that may be incorporated into the end effector of FIG. 2, in an on-plane configuration;

FIG. 73 depicts a front elevational view of tissue clamped between the keyhole blade and clamp arm assembly of FIG. 71, in a first off-plane configuration; and FIG. 74 depicts a front elevational view of tissue clamped between the keyhole blade and clamp arm assembly of FIG. 71, in a second off-plane configuration.

Figure 1:
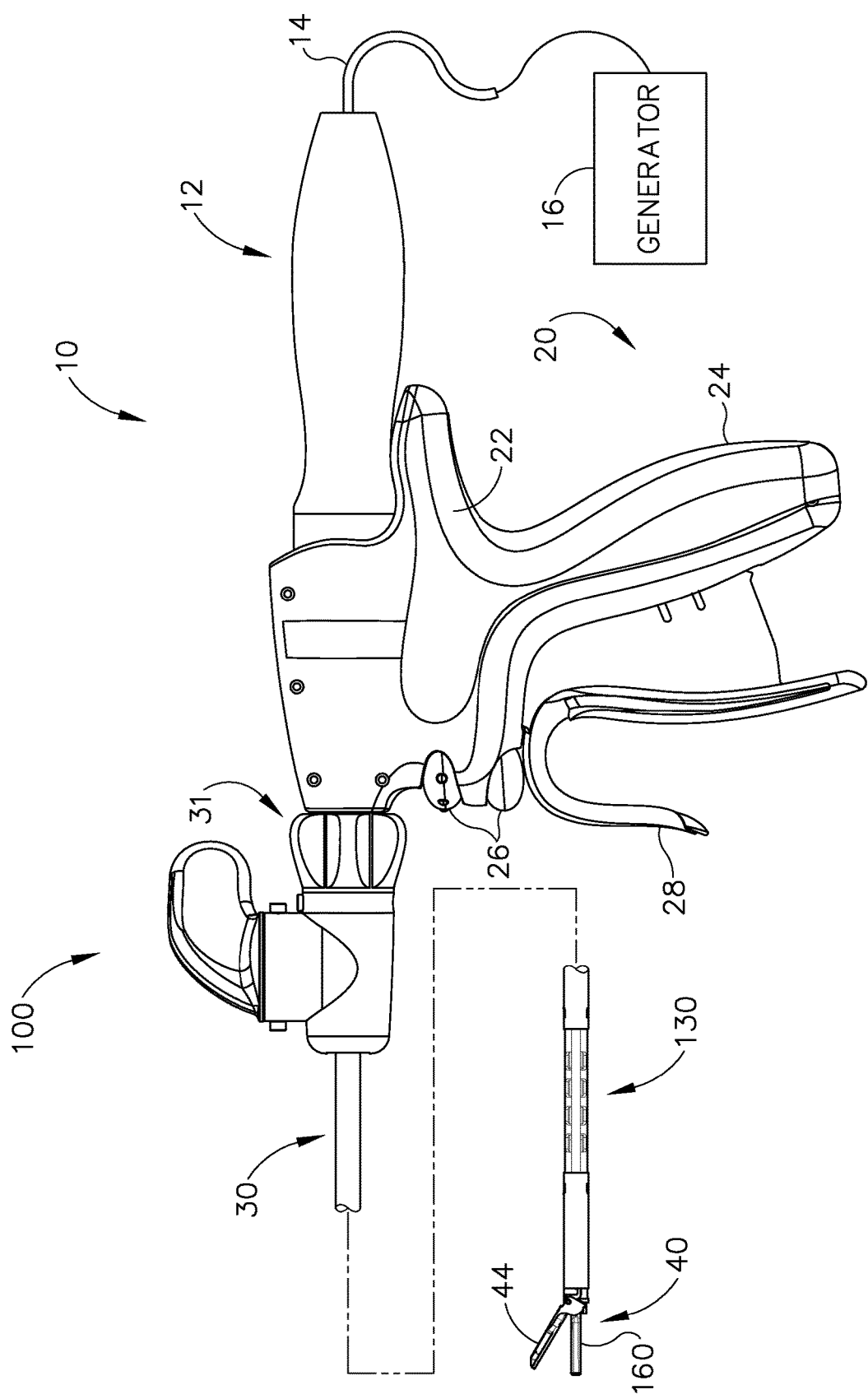
FIG. 1 depicts a side elevational view of an exemplary ultrasonic surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers to the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

I. EXEMPLARY ULTRASONIC SURGICAL INSTRUMENT

FIG. 1 shows an exemplary ultrasonic surgical instrument (10). At least part of instrument (10) may be constructed and operable in accordance with at least some of the teachings of any of the various patents, patent application publications, and patent applications that are cited herein. As described therein and as will be described in greater detail below, instrument (10) is operable to cut tissue and seal or weld tissue (e.g., a blood vessel, etc.) substantially simultaneously. It should also be understood that instrument (10) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instrument (10) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instrument (10), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

Instrument (10) of the present example comprises a handle assembly (20), a shaft assembly (30), and an end effector (40). Handle assembly (20) comprises a body (22) including a pistol grip (24) and a pair of buttons (26). Handle assembly (20) also includes a trigger (28) that is pivotable toward and away from pistol grip (24). It should be understood, however, that various other suitable configurations may be used, including but not limited to a scissor grip configuration. End effector (40) includes an ultrasonic blade (160) and a pivoting clamp arm (44). Clamp arm (44) is coupled with trigger (28) such that clamp arm (44) is pivotable toward ultrasonic blade (160) in response to pivoting of trigger (28) toward pistol grip (24); and such that clamp arm (44) is pivotable away from ultrasonic blade (160) in response to pivoting of trigger (28) away from pistol grip (24). Various suitable ways in which clamp arm (44) may be coupled with trigger (28) will be apparent to those of ordinary skill in the art in view of the teachings herein. In some versions, one or more resilient members are used to bias clamp arm (44) and/or trigger (28) to the open position shown in FIG. 1.

An ultrasonic transducer assembly (12) extends proximally from body (22) of handle assembly (20). Transducer assembly (12) is coupled with a generator (16) via a cable (14), such that transducer assembly (12) receives electrical power from generator (16). Piezoelectric elements in transducer assembly (12) convert that electrical power into ultrasonic vibrations. Generator (16) may include a power source and control module that is configured to provide a power profile to transducer assembly (12) that is particularly suited for the generation of ultrasonic vibrations through transducer assembly (12). By way of example only, generator (16) may comprise a GEN 300 sold by Ethicon Endo-Surgery, Inc. of Cincinnati, Ohio. In addition or in the alternative, generator (16) may be constructed in accordance with at least some of the teachings of U.S. Pat. No. 8,986,302, entitled "Surgical Generator for Ultrasonic and Electrosurgical Devices," published Apr. 14, 2011, the disclosure of which is incorporated by reference herein. It should also be understood that at least some of the functionality of generator (16) may be integrated into handle assembly (20), and that handle assembly (20) may even include a battery or other on-board power source such that cable (14) is omitted. Still other suitable forms that generator (16) may take, as well as various features and operabilities that generator (16) may provide, will be apparent to those of ordinary skill in the art in view of the teachings herein.

A. Exemplary End Effector and Acoustic Drivetrain

Figure 2:
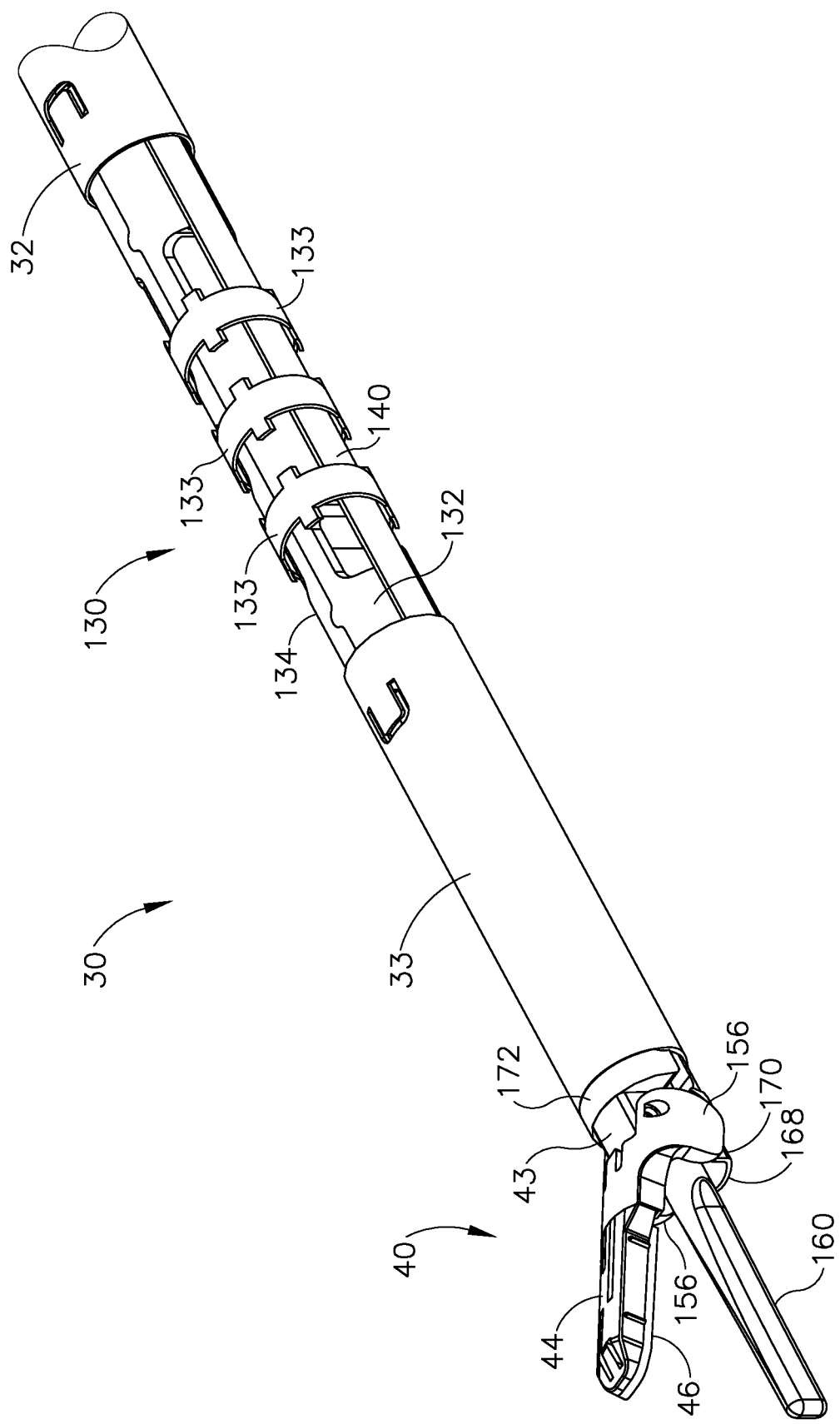
FIG. 2 depicts a perspective view of an articulation section of a shaft assembly and an end effector of the surgical instrument of FIG. 1.
Figure 3:
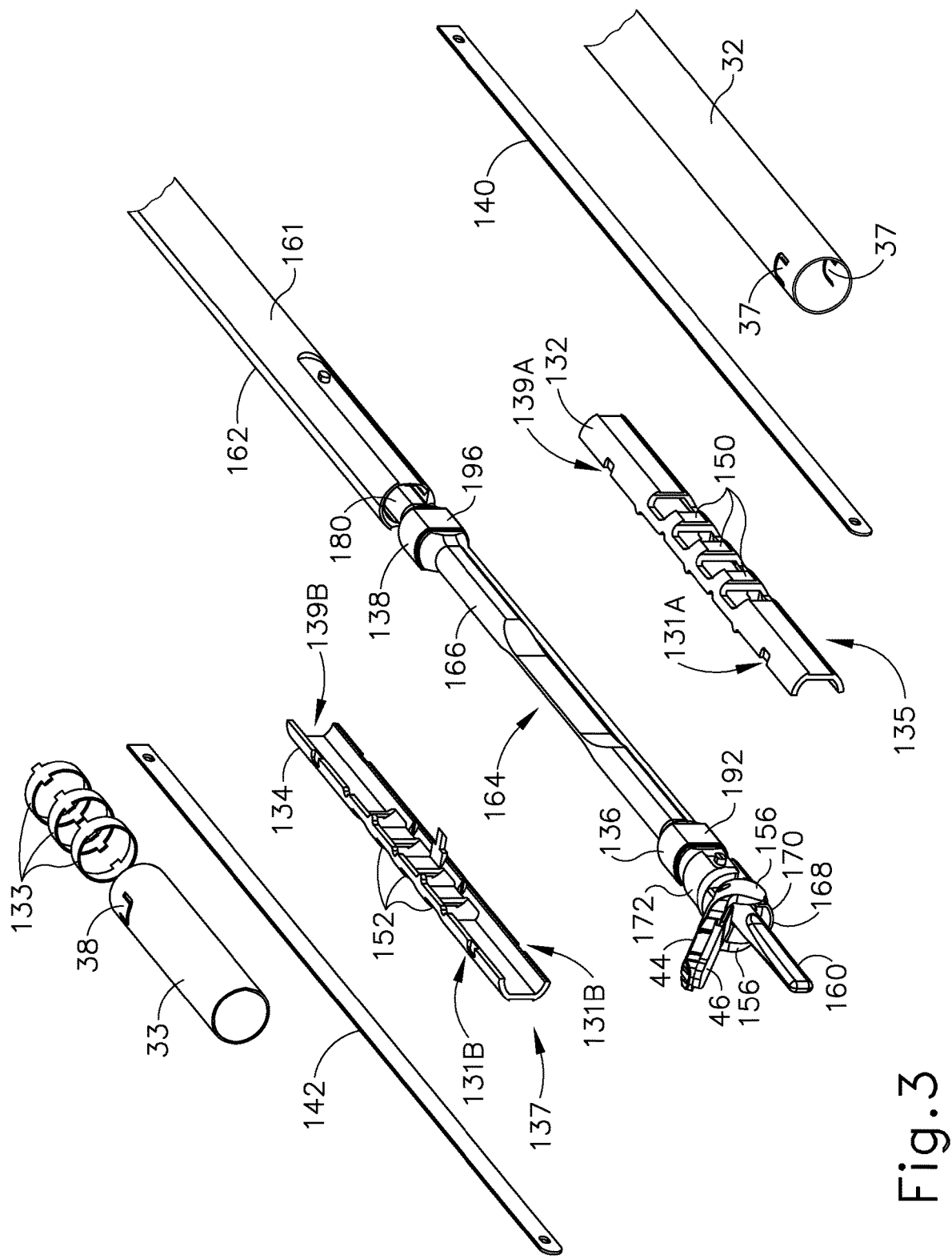
FIG. 3 depicts an exploded perspective view of an articulation section of the shaft assembly of FIG. 2.
Figure 4:
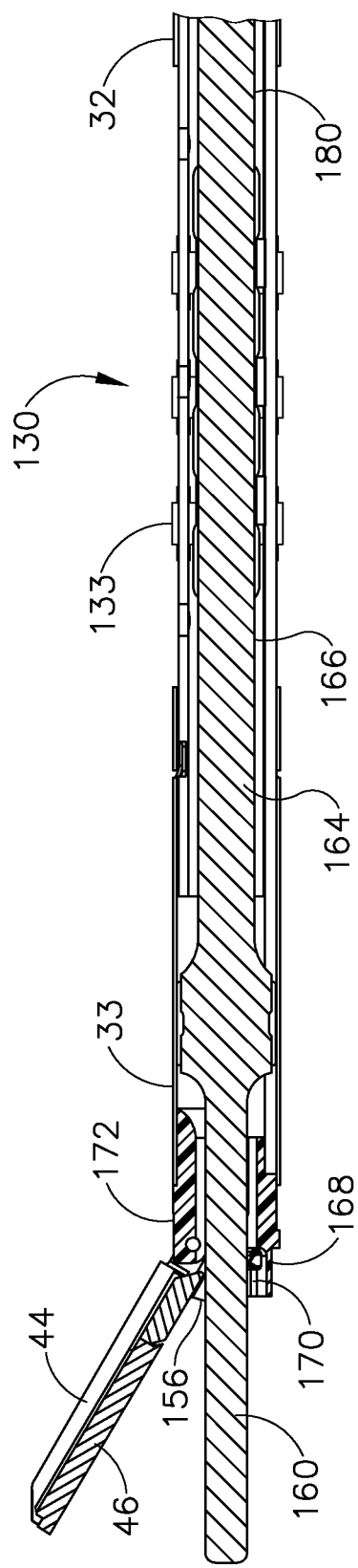
FIG. 4 depicts a cross-sectional side view of the shaft assembly and end effector of FIG. 2.

As best seen in FIGS. 2-4, end effector (40) of the present example comprises clamp arm (44) and ultrasonic blade (160). Clamp arm (44) includes a clamp pad (46) that is secured to the underside of clamp arm (44), facing blade (160). Clamp pad (46) may comprise polytetrafluoroethylene (PTFE) and/or any other suitable material(s). Clamp arm (44) is pivotally secured to a distally projecting tongue (43) of an upper distal shaft element (172), which is fixedly secured within a distal portion of a distal outer sheath (33). Clamp arm (44) is operable to selectively pivot toward and away from blade (160) to selectively clamp tissue between clamp arm (44) and blade (160). A pair of arms (156) extend transversely from clamp arm (44) and are pivotally secured to a lower distal shaft element (170), which is slidably disposed within the distal portion of distal outer sheath (33).

Figure 7:
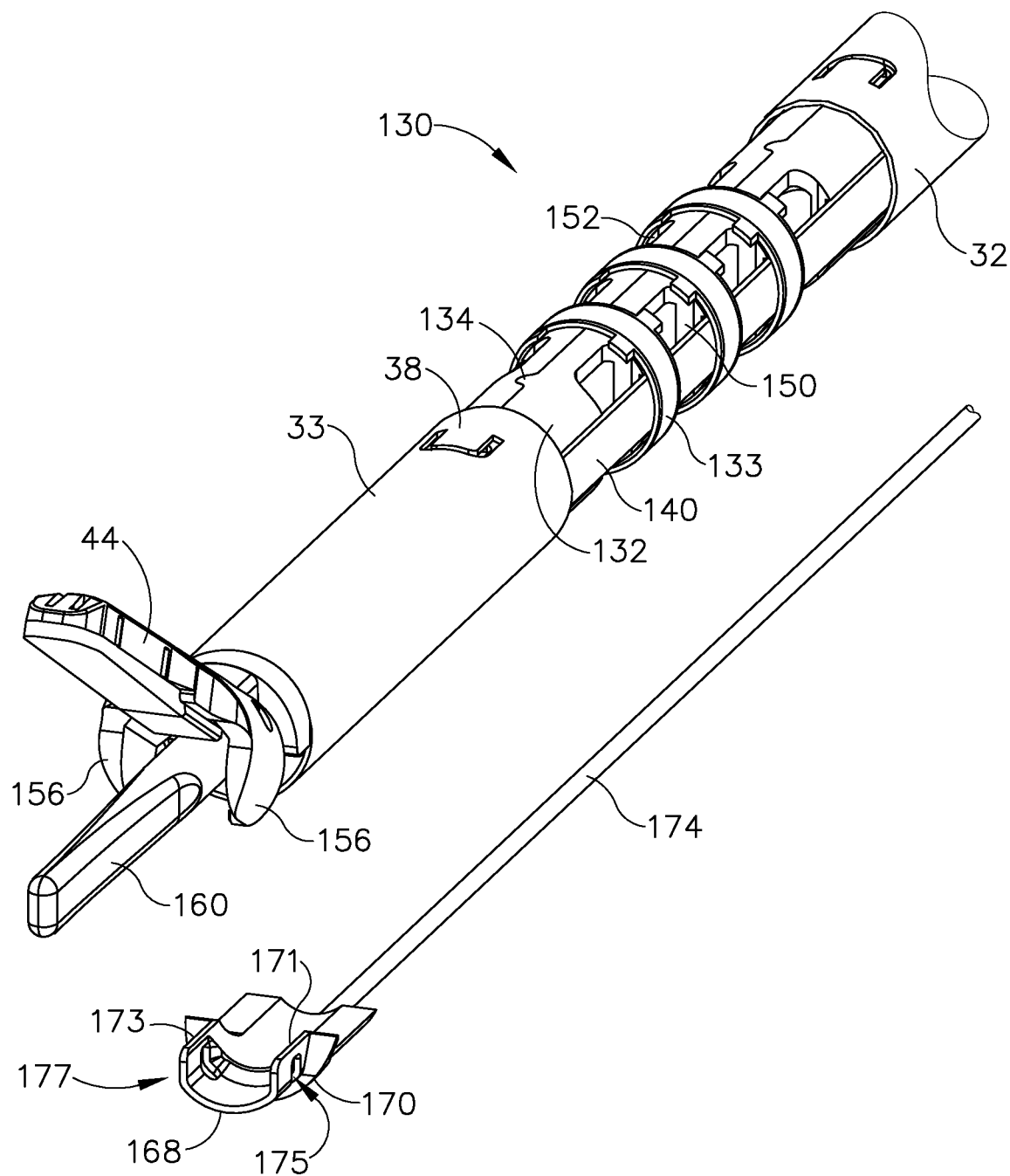
FIG. 7 depicts a partially exploded perspective view of the shaft assembly and end effector of FIG. 2.
Figure 8:
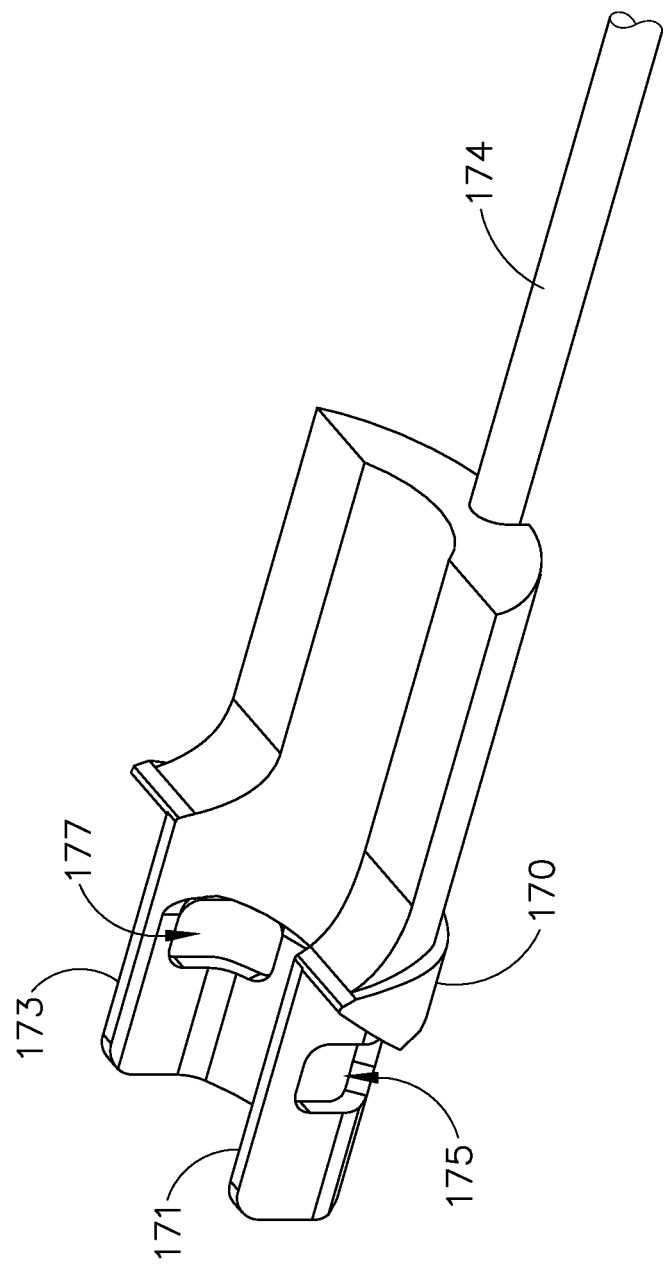
FIG. 8 depicts a perspective view of a distal collar and a drive cable of the shaft assembly of FIG. 2.

As best seen in FIGS. 7-8, a cable (174) is secured to lower distal shaft element (170). Cable (174) is operable to translate longitudinally relative to an articulation section (130) of shaft assembly (30) to selectively pivot clamp arm (44) toward and away from blade (160). In particular, cable (174) is coupled with trigger (28) such that cable (174) translates proximally in response to pivoting of trigger (28) toward pistol grip (24), and such that clamp arm (44) thereby pivots toward blade (160) in response to pivoting of trigger (28) toward pistol grip (24). In addition, cable (174) translates distally in response to pivoting of trigger (28) away from pistol grip (24), such that clamp arm (44) pivots away from blade (160) in response to pivoting of trigger (28) away from pistol grip (24). Clamp arm (44) may be biased toward the open position, such that (at least in some instances) the operator may effectively open clamp arm (44) by releasing a grip on trigger (28).

Figure 10A:
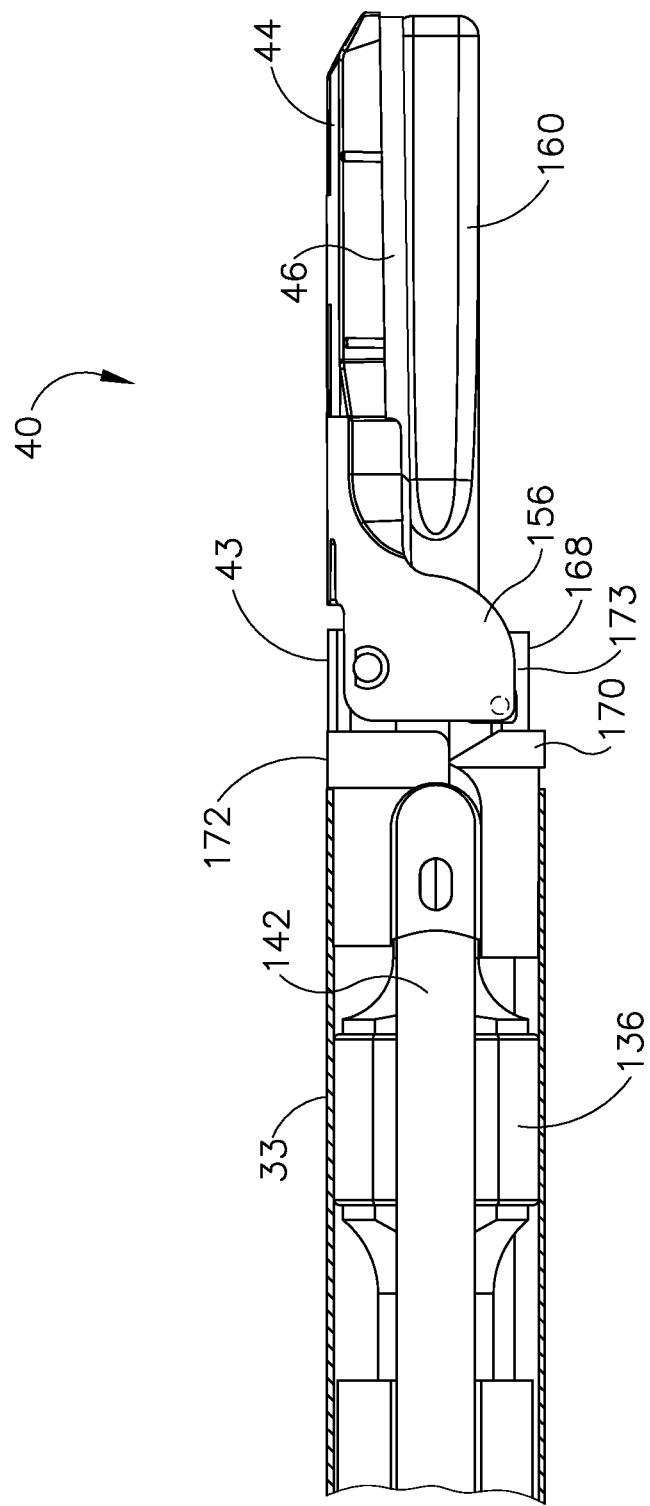
FIG. 10A depicts a side elevational view of an exemplary alternative end effector and the distal portion of a shaft assembly, configured for incorporation in the instrument of FIG. 1, with a clamp arm of the end effector in a closed position, and with an outer sheath shown in cross-section to reveal components within the outer sheath.
Figure 10B:
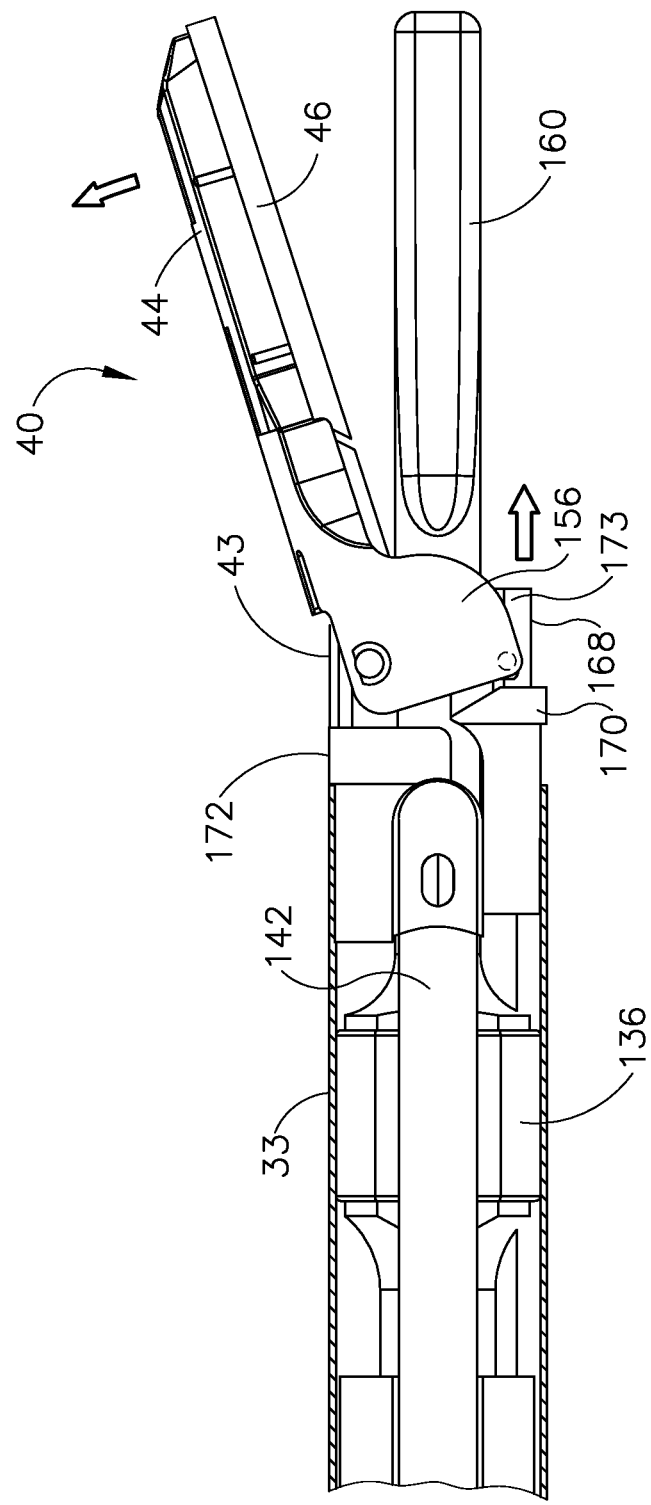
FIG. 10B depicts a side elevational view of the shaft assembly and end effector of FIG. 10A, with the clamp arm moved to a partially open position.
Figure 10C:
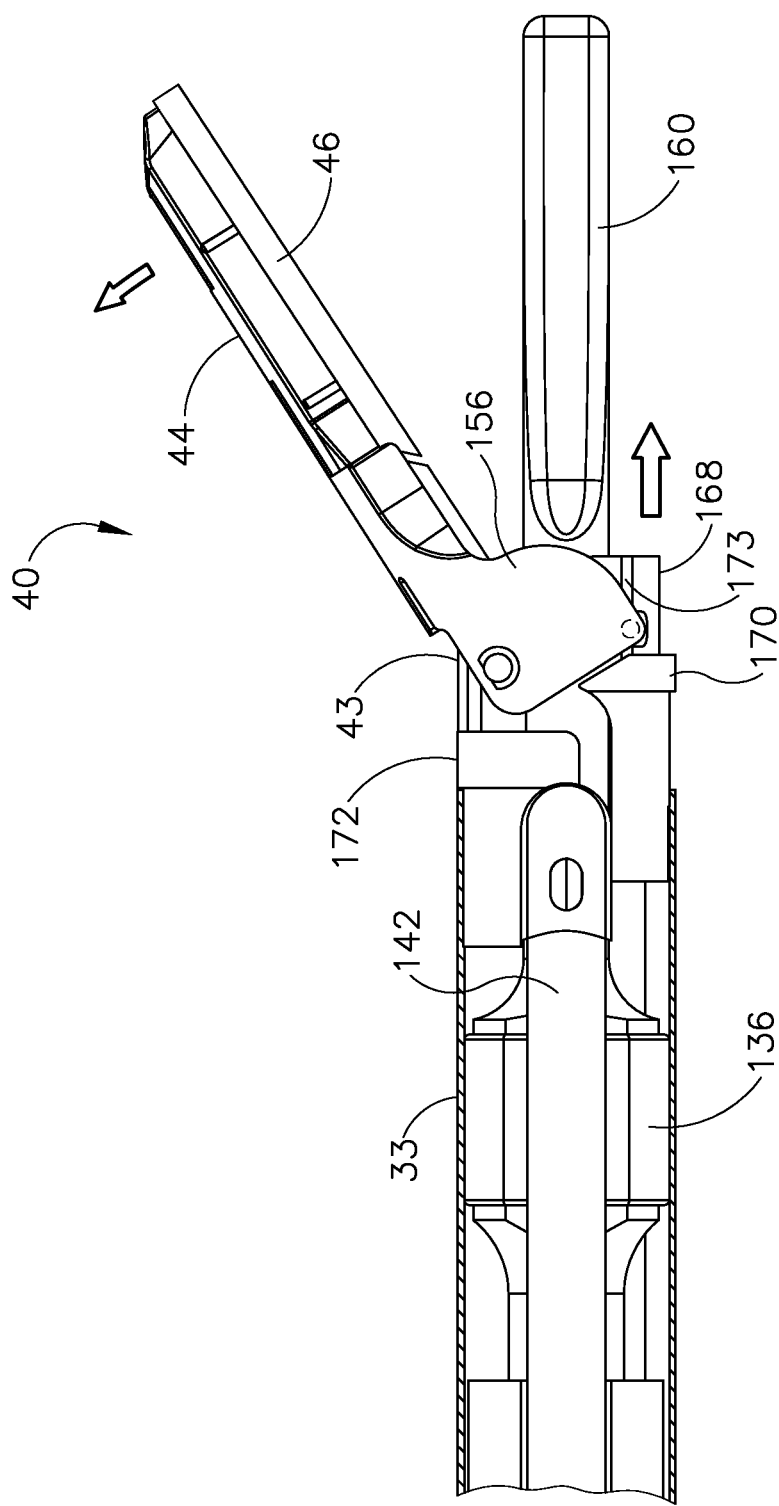
FIG. 10C depicts a side elevational view of the shaft assembly and end effector of FIG. 10A, with the clamp arm moved to a fully open position.

As shown in FIGS. 7-8, cable (174) is secured to a proximal end of lower distal shaft element (170). Lower distal shaft element (170) comprises a pair of distal flanges (171, 173) extending from a semi-circular base (168). Flanges (171, 173) each comprise a respective opening (175, 177). Clamp arm (44) is rotatably coupled to lower distal shaft element (170) via a pair of inwardly extending integral pins (41, 45). Pins (41, 45) extend inwardly from arms (156) of clamp arm (44) and are rotatably disposed within respective openings (175, 177) of lower distal shaft element (170). As shown in FIGS. 10A-10C, longitudinal translation of cable (174) causes longitudinal translation of lower distal shaft element (170) between a proximal position (FIG. 10A) and a distal position (FIG. 10C). Longitudinal translation of lower distal shaft element (170) causes rotation of clamp arm (44) between a closed position (FIG. 10A) and an open position (FIG. 10C).

Blade (160) of the present example is operable to vibrate at ultrasonic frequencies in order to effectively cut through and seal tissue, particularly when the tissue is being compressed between clamp pad (46) and blade (160). Blade (160) is positioned at the distal end of an acoustic drivetrain. This acoustic drivetrain includes transducer assembly (12) and an acoustic waveguide (180). Acoustic waveguide (180) comprises a flexible portion (166). Transducer assembly (12) includes a set of piezoelectric discs (not shown) located proximal to a horn (not shown) of waveguide (180). The piezoelectric discs are operable to convert electrical power into ultrasonic vibrations, which are then transmitted along waveguide (180), including flexible portion (166) of waveguide (180) to blade (160) in accordance with known configurations and techniques. By way of example only, this portion of the acoustic drivetrain may be configured in accordance with various teachings of various references that are cited herein.

As best seen in FIG. 3, flexible portion (166) of waveguide (180) includes a distal flange (136), a proximal flange (138), and a narrowed section (164) located between flanges (136, 138). In the present example, flanges (136, 138) are located at positions corresponding to nodes associated with resonant ultrasonic vibrations communicated through flexible portion (166) of waveguide (180). Narrowed section (164) is configured to allow flexible portion (166) of waveguide (180) to flex without significantly affecting the ability of flexible portion (166) of waveguide (180) to transmit ultrasonic vibrations. By way of example only, narrowed section (164) may be configured in accordance with one or more teachings of U.S. Pub. No. 2014/0005701 issued as U.S. Pat. No. 9,393,037 on Jul. 19, 2016 and/or U.S. Pub. No. 2014/0114334, issued as U.S. Pat. No. 9,095,367 on Aug. 4, 2015, the disclosures of which are incorporated by reference herein. It should be understood that waveguide (180) may be configured to amplify mechanical vibrations transmitted through waveguide (180). Furthermore, waveguide (180) may include features operable to control the gain of the longitudinal vibrations along waveguide (180) and/or features to tune waveguide (180) to the resonant frequency of the system. Various suitable ways in which waveguide (180) may be mechanically and acoustically coupled with transducer assembly (12) will be apparent to those of ordinary skill in the art in view of the teachings herein.

In the present example, the distal end of blade (160) is located at a position corresponding to an anti-node associated with resonant ultrasonic vibrations communicated through flexible portion (166) of waveguide (180), in order to tune the acoustic assembly to a preferred resonant frequency $f_o$ when the acoustic assembly is not loaded by tissue. When transducer assembly (12) is energized, the distal end of blade (160) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (12) of the present example is activated, these mechanical oscillations are transmitted through waveguide (180) to reach blade (160), thereby providing oscillation of blade (160) at the resonant ultrasonic frequency. Thus, when tissue is secured between blade (160) and clamp pad (46), the ultrasonic oscillation of blade (160) may simultaneously sever the tissue and denature the proteins in adjacent tissue cells, thereby providing a coagulative effect with relatively little thermal spread. In some versions, an electrical current may also be provided through blade (160) and clamp arm

(44) to also cauterize the tissue. While some configurations for an acoustic transmission assembly and transducer assembly (12) have been described, still other suitable configurations for an acoustic transmission assembly and transducer assembly (12) will be apparent to one or ordinary skill in the art in view of the teachings herein. Similarly, other suitable configurations for end effector (40) will be apparent to those of ordinary skill in the art in view of the teachings herein.

B. Exemplary Shaft Assembly and Articulation Section

Shaft assembly (30) of the present example extends distally from handle assembly (20). As shown in FIGS. 2-7, shaft assembly (30) includes distal outer sheath (33) and a proximal outer sheath (32) that enclose clamp arm (44) drive features and the above-described acoustic transmission features. Shaft assembly (30) further includes an articulation section (130), which is located at a distal portion of shaft assembly (30), with end effector (40) being located distal to articulation section (130). As shown in FIG. 1, a knob (31) is secured to a proximal portion of proximal outer sheath (32). Knob (31) is rotatable relative to body (22), such that shaft assembly (30) is rotatable about the longitudinal axis defined by outer sheath (32), relative to handle assembly (20). Such rotation may provide rotation of end effector (40), articulation section (130), and shaft assembly (30) unitarily. Of course, rotatable features may simply be omitted if desired.

Articulation section (130) is operable to selectively position end effector (40) at various lateral deflection angles relative to a longitudinal axis defined by outer sheath (32). Articulation section (130) may take a variety of forms. By way of example only, articulation section (130) may be configured in accordance with one or more teachings of U.S. Pub. No. 2012/0078247, issued as U.S. Pat. No. 9,402,682 on Aug. 2, 2016, the disclosure of which is incorporated by reference herein. As another merely illustrative example, articulation section (130) may be configured in accordance with one or more teachings of U.S. Pub. No. 2014/0005701, issued as U.S. Pat. No. 9,393,037 on Jul. 19, 2016 and/or U.S. Pub. No. 2014/0114334, issued as U.S. Pat. No. 9,095,367 on Aug. 4, 2015, the disclosures of which are incorporated by reference herein. Various other suitable forms that articulation section (130) may take will be apparent to those of ordinary skill in the art in view of the teachings herein.

As best seen in FIGS. 2-6B articulation section (130) of this example comprises a set of three retention collars (133) and a pair of ribbed body portions (132, 134), with a pair of articulation bands (140, 142) extending along respective channels (135, 137) defined between interior surfaces of retention collars (133) and exterior surfaces of ribbed body portions (132, 134). Ribbed body portions (132, 134) are longitudinally positioned between flanges (136, 138) of flexible portion (166) of waveguide (180). In some versions, ribbed body portions (132, 134) snap together about flexible portion (166) of waveguide (180). Ribbed body portions (132, 134) are configured to flex with flexible portion (166) of waveguide (180) when articulation section (130) bends to achieve an articulated state.

FIG. 3 shows ribbed body portions (132, 134) in greater detail. In the present example, ribbed body portions (132, 134) are formed of a flexible plastic material, though it should be understood that any other suitable material may be used. Ribbed body portion (132) comprises a set of three ribs (150) that are configured to promote lateral flexing of ribbed body portion (132). Of course, any other suitable number of ribs (150) may be provided. Ribbed body portion (132) also defines a channel (135) that is configured to receive articulation band (140) while allowing articulation band (140) to slide relative to ribbed body portion (132). Similarly, ribbed body portion (134) comprises a set of three ribs (152) that are configured to promote lateral flexing of ribbed body portion (134). Of course, any other suitable number of ribs (152) may be provided. Ribbed body portion (134) also defines a channel (137) that is configured to receive articulation band (142) while allowing articulation band (142) to slide relative to ribbed body portion (137).

Figure 5:
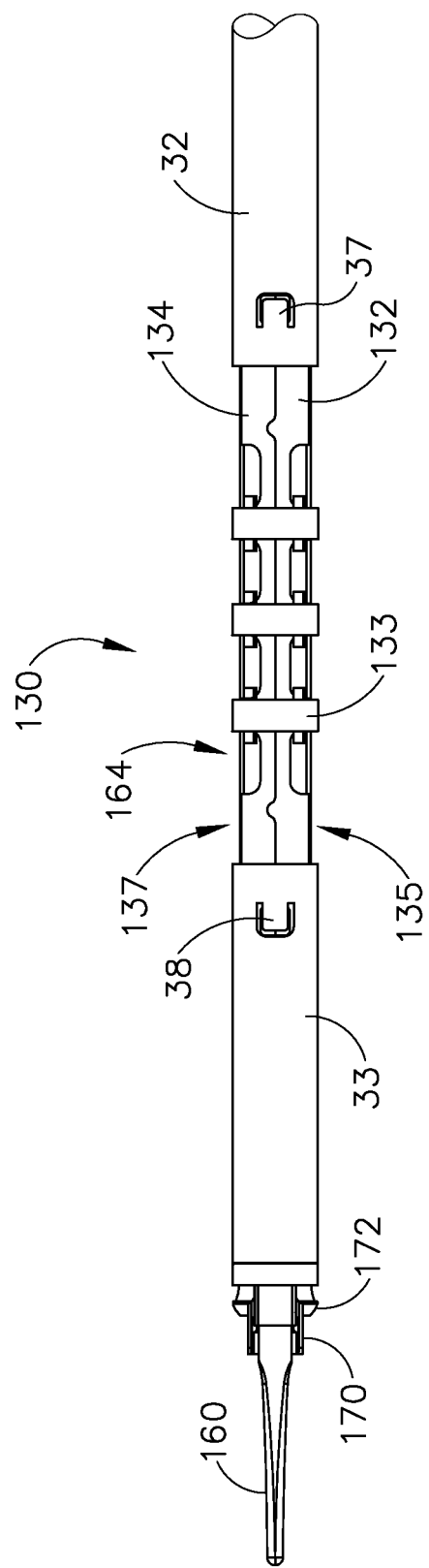
FIG. 5 depicts a top plan view of the shaft assembly and end effector of FIG. 2.

As best seen in FIG. 5, ribbed body portions (132, 134) are laterally interposed between articulation bands (140, 142) and flexible portion (166) of waveguide (180). Ribbed body portions (132, 134) mate with each other such that they together define an internal passage sized to accommodate flexible portion (166) of waveguide (180) without contacting waveguide (180). In addition, when ribbed body portions (132, 134) are coupled together, a pair of complementary distal notches (131A, 131B) formed in ribbed body portions (132, 134) align to receive a pair of inwardly projecting resilient tabs (38) of distal outer sheath (33). This engagement between tabs (38) and notches (131A, 131B) longitudinally secures ribbed body portions (132, 134) relative to distal outer sheath (33). Similarly, when ribbed body portions (132, 134) are coupled together, a pair of complementary proximal notches (139A, 139B) formed in ribbed body portions (132, 134) align to receive a pair of inwardly projecting resilient tabs (37) of proximal outer sheath (32). This engagement between tabs (37) and notches (139A, 139B) longitudinally secures ribbed body portions (132, 134) relative to proximal outer sheath (32). Of course, any other suitable kinds of features may be used to couple ribbed body portions (132, 134) with proximal outer sheath (32) and/or distal outer sheath (33).

Figure 6A:
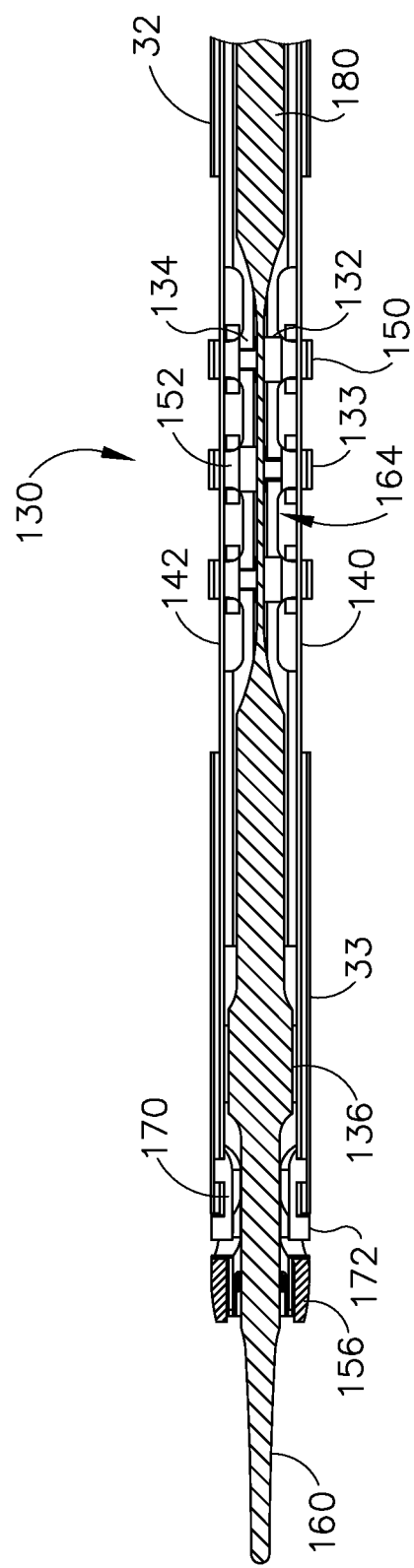
FIG. 6A depicts a cross-sectional top view of the shaft assembly and end effector of FIG. 2 in a straight configuration.
Figure 6B:
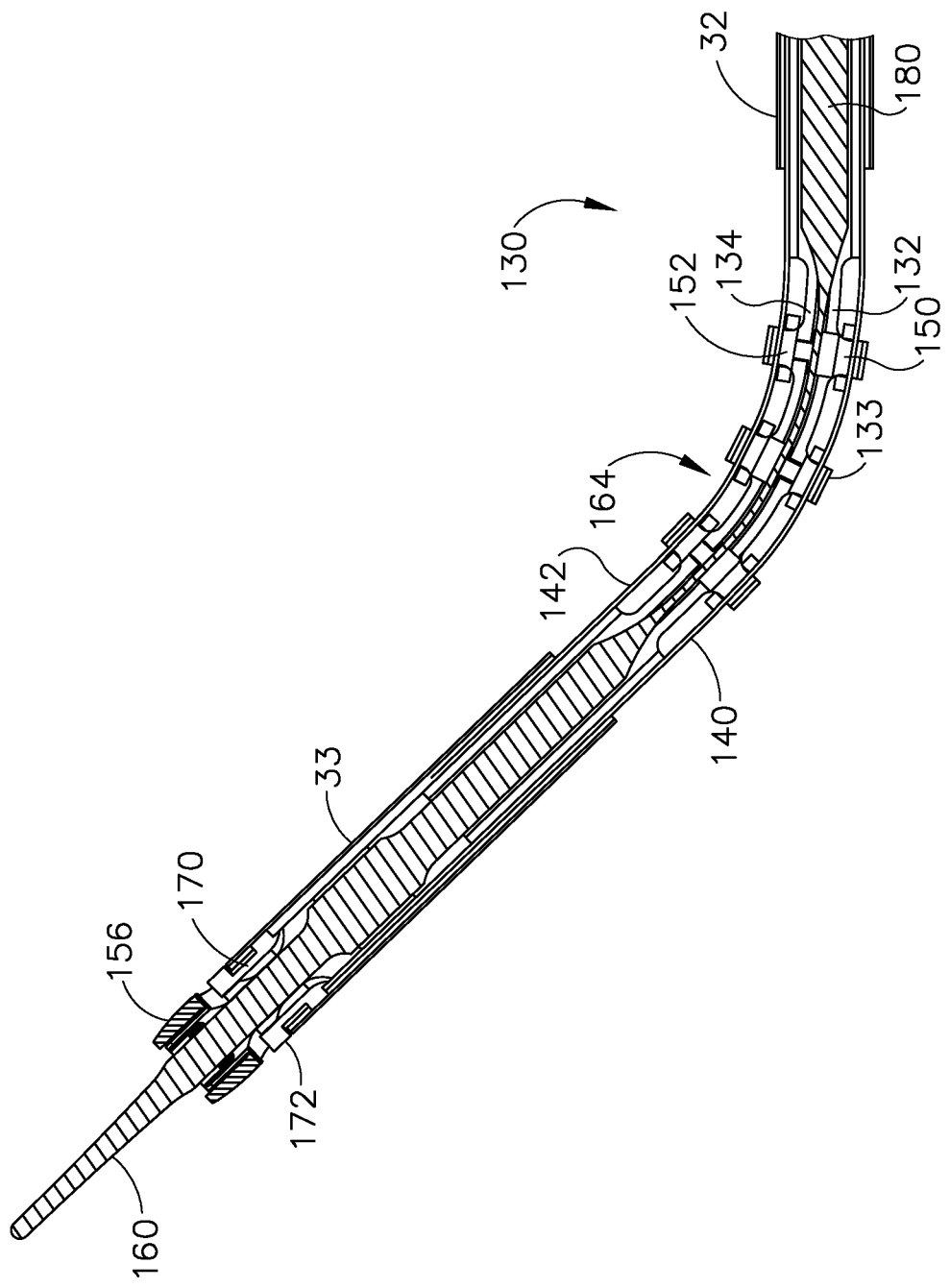
FIG. 6B depicts a cross-sectional top view of the shaft assembly and end effector of FIG. 2 in an articulated configuration.

The distal ends of articulation bands (140, 142) are unitarily secured to upper distal shaft element (172). When articulation bands (140, 142) translate longitudinally in an opposing fashion, this will cause articulation section (130) to bend, thereby laterally deflecting end effector (40) away from the longitudinal axis of shaft assembly (30) from a straight configuration as shown in FIG. 6A to an articulated configuration as shown in FIG. 6B. In particular, end effector (40) will be articulated toward the articulation band (140, 142) that is being pulled proximally. During such articulation, the other articulation band (140, 142) may be pulled distally by upper distal shaft element (172). Alternatively, the other articulation band (140, 142) may be driven distally by an articulation control. Ribbed body portions (132, 134) and narrowed section (164) are all sufficiently flexible to accommodate the above-described articulation of end effector (40). Furthermore, flexible acoustic waveguide (166) is configured to effectively communicate ultrasonic vibrations from waveguide (180) to blade (160) even when articulation section (130) is in an articulated state as shown in FIG. 6B.

As best seen in FIG. 3, each flange (136, 138) of waveguide (180) includes a respective pair of opposing flats (192, 196). Flats (192, 196) are oriented along vertical planes that are parallel to a vertical plane extending through narrowed section (164) of flexible portion (166). Flats (192, 196) are configured to provide clearance for articulation bands (140, 142). In particular, flats (196) of proximal flange (138) accommodate articulation bands (140, 142) between proximal flange (138) and the inner diameter of proximal outer sheath (32): while flats (192) of distal flange (136) accommodate articulation bands (140, 142) between distal flange (136) and the inner diameter of distal outer sheath (33). Of course, flats (192, 196) could be substituted with a variety of features, including but not limited to slots, channels, etc., with any suitable kind of profile (e.g., square, flat, round, etc.). In the present example, flats (192, 196) are formed in a milling process, though it should be understood that any other suitable process(es) may be used. Various suitable alternative configurations and methods of forming flats (192, 196) will be apparent to those of ordinary skill in the art in view of the teachings herein. It should also be understood that waveguide (180) may include flats formed in accordance with at least some of the teachings of U.S. Pub. No. 2013/0289592, entitled "Ultrasonic Device for Cutting and Coagulating," published Oct. 31, 2013, issued as U.S. Pat. No. 10,238,416 on Mar. 26, 2019, the disclosure of which is incorporated by reference herein.

In the present example, outer rings (133) are located at longitudinal positions corresponding to ribs (150, 152), such that three rings (133) are provided for three ribs (150, 152). Articulation band (140) is laterally interposed within channel (135) between rings (133) and ribbed body portion (132); while articulation band (142) is laterally interposed within channel (137) between rings (133) and ribbed body portion (134). Rings (133) are configured to keep articulation bands (140, 142) in a parallel relationship, particularly when articulation section (130) is in a bent configuration (e.g., similar to the configuration shown in FIG. 6B). In other words, when articulation band (140) is on the inner diameter of a curved configuration presented by a bent articulation section (130), rings (133) may retain articulation band (140) such that articulation band (140) follows a curved path that complements the curved path followed by articulation band (142). It should be understood that channels (135, 137) are sized to accommodate respective articulation bands (140, 142) in such a way that articulation bands (140, 142) may still freely slide through articulation section (130), even with rings (133) being secured to ribbed body portions (150, 152). It should also be understood that rings (133) may be secured to ribbed body portions (132, 134) in various ways, including but not limited to interference fitting, adhesives, welding, etc.

When articulation bands (140, 142) are translated longitudinally in an opposing fashion, a moment is created and applied to a distal end of distal outer sheath (33) via upper distal shaft element (172). This causes articulation section (130) and narrowed section (164) of flexible portion (166) of waveguide (180) to articulate, without transferring axial forces in articulation bands (140, 142) to waveguide (180). It should be understood that one articulation band (140, 142) may be actively driven distally while the other articulation band (140, 142) is passively permitted to retract proximally. As another merely illustrative example, one articulation band (140, 142) may be actively driven proximally while the other articulation band (140, 142) is passively permitted to advance distally. As yet another merely illustrative example, one articulation band (140, 142) may be actively driven distally while the other articulation band (140, 142) is actively driven proximally. Various suitable ways in which articulation bands (140, 142) may be driven will be apparent to those of ordinary skill in the art in view of the teachings herein.

As best seen in FIG. 9, an articulation control assembly (100) is secured to a proximal portion of outer sheath (32). Articulation control assembly (100) comprises a housing (110) and a rotatable knob (120). Housing (110) comprises a pair of perpendicularly intersecting cylindrical portions (112, 114). Knob (120) is rotatably disposed within a first hollow cylindrical portion (112) of housing (110) such that knob (120) is operable to rotate within cylindrical portion (112) of housing (110). Shaft assembly (30) is slidably and rotatably disposed within a second cylindrical portion (114).

Shaft assembly (30) comprises a pair of translatable members (161, 162), both of which extend slidably and longitudinally through the proximal portion of outer sheath (32). Translatable members (161, 162) are longitudinally translatable within second cylindrical portion (114) between a distal position and a proximal position. Translatable members (161, 162) are mechanically coupled with respective articulation bands (140, 142) such that longitudinal translation of translatable member (161) causes longitudinal translation of articulation band (140), and such that longitudinal translation of translatable member (162) causes longitudinal translation of articulation band (142).

Knob (120) comprises a pair of pins (122, 124) extending downwardly from a bottom surface of knob (120). Pins (122, 124) extend into second cylindrical portion (114) of housing (110) and are rotatably and slidably disposed within a respective pair of channels (163, 164) formed in top surfaces of translatable members (161, 162). Channels (163, 164) are positioned on opposite sides of an axis of rotation of knob (120), such that rotation of knob (120) about that axis causes opposing longitudinal translation of translatable members (161, 162). For instance, rotation of knob (120) in a first direction causes distal longitudinal translation of translatable member (161) and articulation band (140), and proximal longitudinal translation of translatable member (162) and articulation band (142); and rotation of knob (120) in a second direction causes proximal longitudinal translation of translatable member (161) and articulation band (140), and distal longitudinal translation of translatable member (162) and articulation band (142). Thus, it should be understood that rotation of rotation knob (120) causes articulation of articulation section (130).

Housing (110) of articulation control assembly (100) comprises a pair of set screws (111, 113) extending inwardly from an interior surface of first cylindrical portion (112). With knob (120) rotatably disposed within first cylindrical portion (112) of housing (110), set screws (111, 113) are slidably disposed within a pair of arcuate channels (121, 123) formed in knob (120). Thus, it should be understood that rotation of knob (120) will be limited by movement of set screws (111, 113) within channels (121, 123). Set screws (111, 113) also retain knob (120) in housing (110), preventing knob (120) from traveling vertically within first cylindrical portion (112) of housing (110).

An interior surface of first cylindrical portion (112) of housing (110) comprises a first angular array of teeth (116) and a second angular array of teeth (118) formed in an interior surface of first cylindrical portion (112). Rotation knob (120) comprises a pair of outwardly extending engagement members (126, 128) that are configured to engage teeth (116, 118) of first cylindrical portion (112) in a detent relationship to thereby selectively lock knob (120) in a particular rotational position. The engagement of engagement members (126, 128) with teeth (116, 118) may be overcome by a user applying sufficient rotational force to knob (120); but absent such force, the engagement will suffice to maintain the straight or articulated configuration of articulation section (130). It should therefore be understood that the ability to selectively lock knob (120) in a particular rotational position lock will enable an operator to selectively lock articulation section (130) in a particular deflected position relative to the longitudinal axis defined by outer sheath (32).

In some versions of instrument (10), articulation section (130) of shaft assembly (30) is operable to achieve articulation angles up to between approximately 15° and approximately 30°, both relative to the longitudinal axis of shaft assembly (30) when shaft assembly (30) is in a straight (non-articulated) configuration. Alternatively, articulation section (130) may be operable to achieve any other suitable articulation angles.

In some versions of instrument (10), narrowed section (164) of waveguide (180) has a thickness between approximately 0.01 inches and approximately 0.02 inches. Alternatively, narrowed section (164) may have any other suitable thickness. Also in some versions, narrowed section (164) has a length of between approximately 0.4 inches and approximately 0.65 inches. Alternatively, narrowed section (164) may have any other suitable length. It should also be understood that the transition regions of waveguide (180) leading into and out of narrowed section (164) may be quarter rounded, tapered, or have any other suitable configuration.

In some versions of instrument (10), flanges (136, 138) each have a length between approximately 0.1 inches and approximately 0.2 inches. Alternatively, flanges (136, 138) may have any other suitable length. It should also be understood that the length of flange (136) may differ from the length of flange (138). Also in some versions, flanges (136, 138) each have a diameter between approximately 0.175 inches and approximately 0.2 inches. Alternatively, flanges (136, 138) may have any other suitable outer diameter. It should also be understood that the outer diameter of flange (136) may differ from the outer diameter of flange (138).

While the foregoing exemplary dimensions are provided in the context of instrument (10) as described above, it should be understood that the same dimensions may be used in any of the other examples described herein. It should also be understood that the foregoing exemplary dimensions are merely optional. Any other suitable dimensions may be used.

C. Exemplary Alternative End Effector and Shaft Assembly Configuration with Dual Role Bands and Flex Section as Ground FIGS. 11A-12B show an exemplary alternative shaft assembly (200) and end effector (240) that may be readily incorporated into instrument (10). Shaft assembly (200) of this example comprises a distal outer sheath (202), a proximal outer sheath (204), and an articulation section (210) configured to operate substantially similar to articulation section (130) discussed above except for the differences discussed below. In particular, articulation section (210) is operable to selectively position end effector (240) at various lateral deflection angles relative to a longitudinal axis defined by proximal outer sheath (204). End effector (240) includes an ultrasonic blade (242) and a pivoting clamp arm (244) having a clamp pad (245). End effector (240) is configured to operate substantially similar to end effector (40) discussed above except for the differences discussed below. In particular, clamp arm (244) of end effector (240) is operable to compress tissue against blade (242). When blade (242) is activated while clamp arm (244) compresses tissue against blade (242), end effector (240) simultaneously severs the tissue and denatures the proteins in adjacent tissue cells, thereby providing a coagulative effect.

Clamp arm (244) is operable to selectively pivot toward and away from blade (242) to selectively clamp tissue between clamp pad (245) and blade (242). Clamp arm (244) is pivotably secured to an upper distal end of distal outer sheath (202) via a pin (222). Distal outer sheath (202) is mechanically grounded to an instrument body (e.g., handle assembly (20), etc.) via articulation section (210) and proximal outer sheath (204). A pair of arms (247) extend transversely from clamp arm (244) and are pivotably secured to a collar (220) via a pin (224). Collar (220) is slidably disposed within distal outer sheath (202). Thus, it should be understood that longitudinal movement of collar (220) within distal outer sheath (202) causes pivoting of clamp arm (244) about pin (222) toward and away from blade (242). Collar (220) is longitudinally driven within distal outer sheath (202) as described in greater detail below.

Figure 11A:
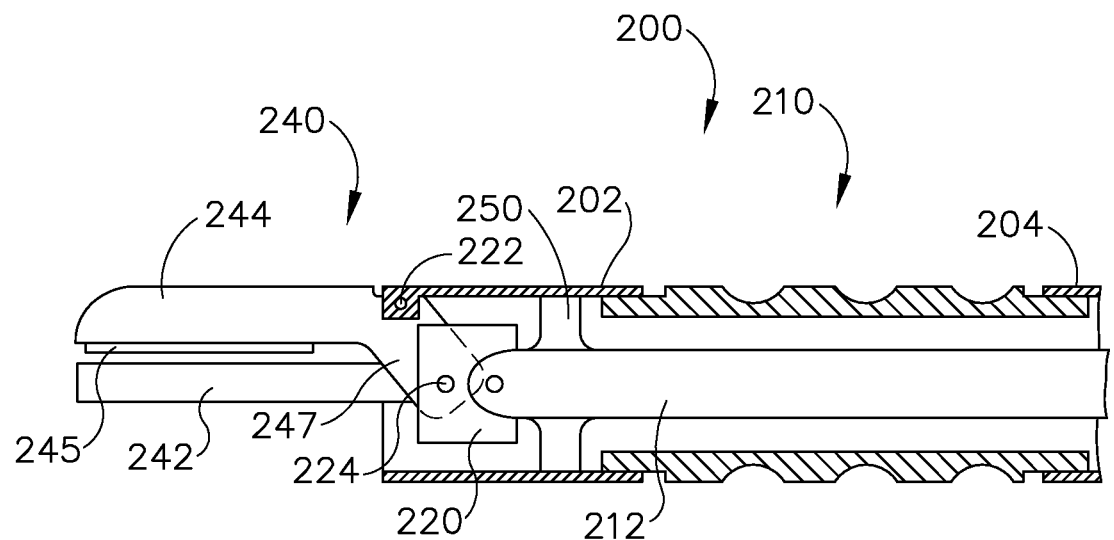
FIG. 11A depicts a side elevational view of another exemplary alternative end effector and the distal portion of a shaft assembly and end effector, configured for incorporation in the instrument of FIG. 1, with a clamp arm of the end effector in a closed position, and with the shaft assembly shown in side cross-section.
Figure 11B:
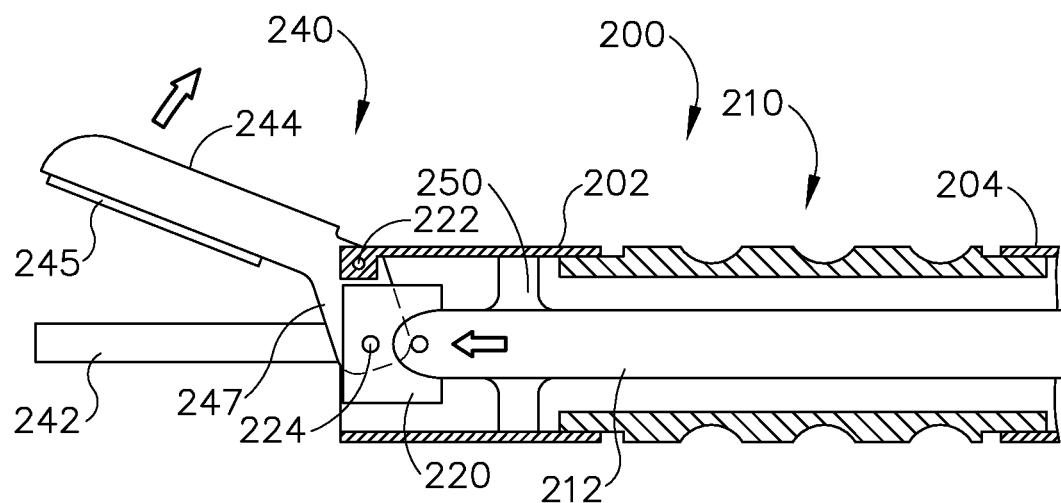
FIG. 11B depicts a side elevational view of the shaft assembly and end effector of FIG. 11A, with the clamp arm moved to an open position, and with the shaft assembly shown in side cross-section.

Blade (242) is positioned at the distal end of an acoustic drivetrain, which passes through an inner bore of collar (220) without contacting collar (220). This acoustic drivetrain includes a transducer assembly (not shown) and an acoustic waveguide (246). Waveguide (246) comprises a flexible portion (248). Flexible portion (248) of waveguide (246) includes a distal flange (250), a proximal flange (not shown), and a narrowed section (249) located between distal flange (250) and the proximal flange. In the present example, distal flange (250) and the proximal flange are located at positions corresponding to nodes associated with resonant ultrasonic vibrations communicated through flexible portion (248) of waveguide (246). Narrowed section (249) is configured to allow flexible portion (248) of waveguide (246) to flex without significantly affecting the ability of flexible portion (248) of waveguide (246) to transmit ultrasonic vibrations. As best seen in FIG. 11A-11B, distal flange (250) engages an interior surface of distal outer sheath (202). In some versions, a gap is defined between distal flange (250) and the interior surface of distal outer sheath (202). In some other versions, a dampening element such as an o-ring is interposed between distal flange (250) and the interior surface of distal outer sheath (202).

Figure 12A:
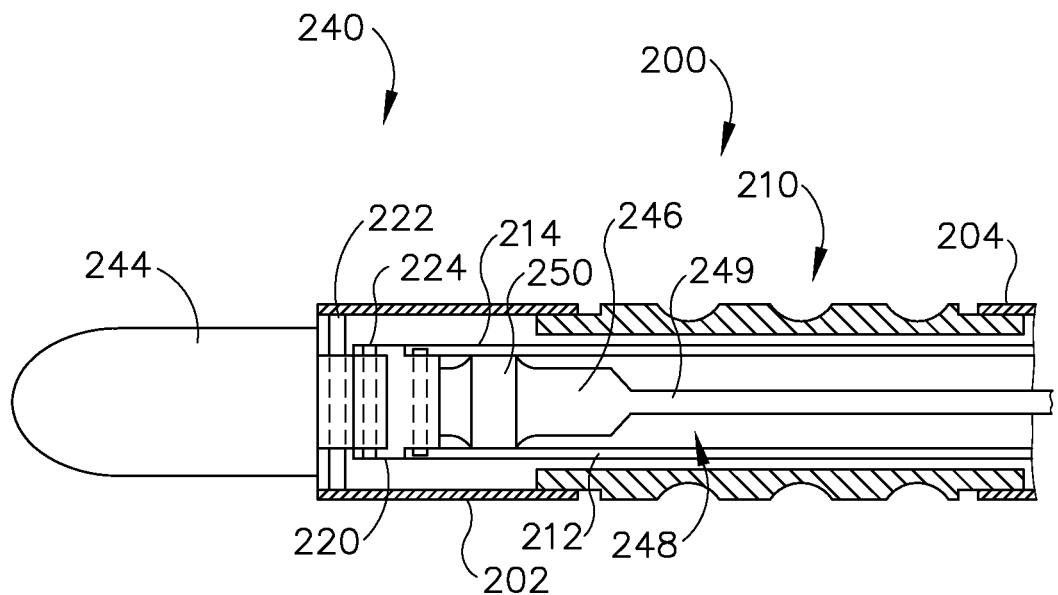
FIG. 12A depicts a top plan view of the shaft assembly and end effector of FIG. 11A in a substantially straight configuration, with the shaft assembly shown in top cross-section.
Figure 12B:
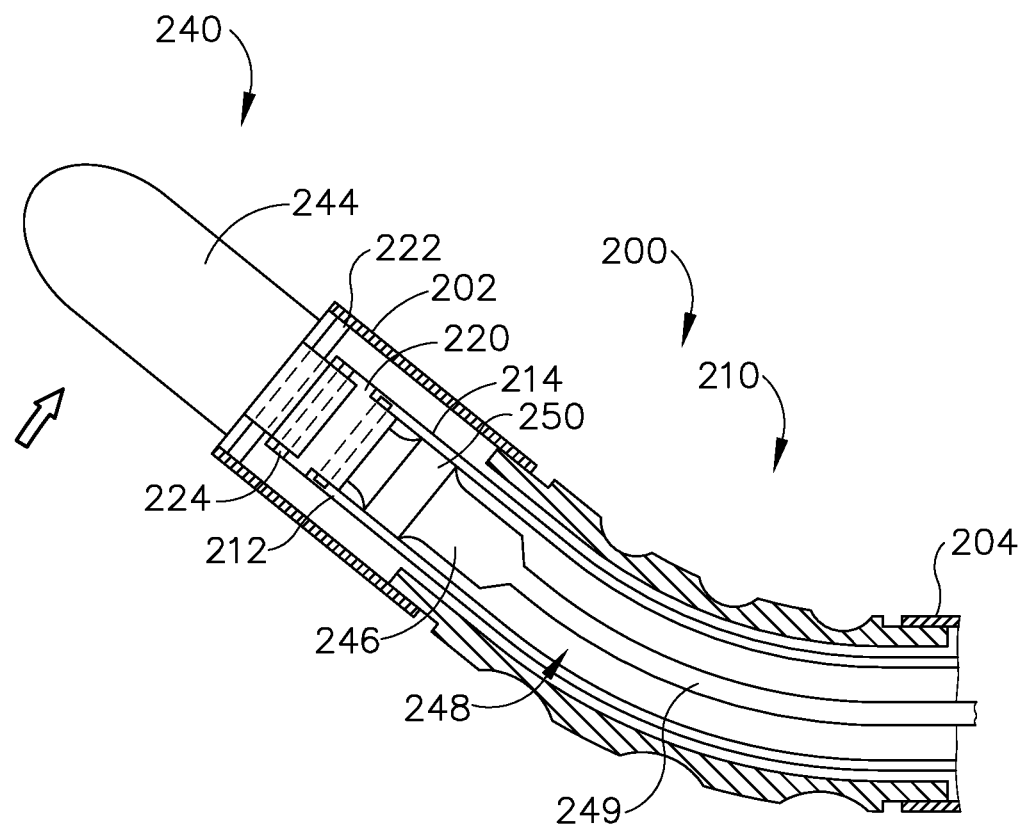
FIG. 12B depicts a top plan view of the shaft assembly and end effector of FIG. 11A in an articulated configuration, with the shaft assembly shown in top cross-section.

Shaft assembly (200) further comprises a pair of articulation bands (212, 214). Distal ends of articulation bands (212, 214) are secured to collar (220). Articulation bands (212, 214) are configured to operate substantially similar to articulation bands (140, 142) discussed above except for the differences discussed below. In particular, as shown in FIGS. 12A-12B, opposing longitudinal motion of articulation bands (212, 214) causes articulation of articulation section (210). When articulation bands (212, 214) are translated longitudinally in an opposing fashion, a moment is created and applied to a distal end of distal outer sheath (202) via pin (222), arms (247) of clamp arm (244), pin (224), and collar (220). This causes articulation section (210) and narrowed section (249) of flexible portion (248) of waveguide (246) to articulate, without transferring axial forces in articulation bands (212, 214) to waveguide (246).

As shown in FIGS. 11A-11B, when articulation bands (212, 214) are both translated in the same direction simultaneously, this simultaneous longitudinal movement of articulation bands (212, 214) causes concurrent longitudinal movement of collar (220) relative to distal outer sheath (202) and the other grounded components of shaft assembly (200). Thus, the simultaneous longitudinal motion of articulation bands (212, 214) in the same direction causes pivoting of clamp arm (244) toward and away from ultrasonic blade (242). It should therefore be understood that opposing longitudinal motion of articulation bands (212, 214) will cause articulation of articulation section (210); distal movement of both articulation bands (212, 214) simultaneously will cause clamp arm (244) to pivot away from blade (242); and proximal movement of both articulation bands (212, 214) simultaneously will cause clamp arm (244) to pivot toward blade (242).

Articulation bands (212, 214) may be driven to translate in an opposing fashion by a modified version of articulation control assembly (100). Articulation bands (212, 214) may be driven to translate in the same direction simultaneously by a modified version of trigger (28). For instance, pivoting of trigger (28) toward and away from pistol grip (24) may cause the entire modified articulation control assembly (100) to translate, which may thereby cause both articulation bands (212, 214) to translate simultaneously in the same direction. Various suitable ways in which articulation control assembly (100) and trigger (28) may be modified and coupled together will be apparent to those of ordinary skill in the art in view of the teachings herein. Similarly, other suitable ways in which articulation bands (212, 214) may be driven (in an opposing fashion and/or simultaneously in the same direction) will be apparent to those of ordinary skill in the art in view of the teachings herein.

D. Exemplary Alternative End Effector and Shaft Assembly Configuration with Dual Role Bands and Waveguide as Ground FIGS. 13A-14B show another exemplary alternative shaft assembly (300) and end effector (340) that may be readily incorporated into instrument (10). Shaft assembly (300) of this example comprises a distal outer sheath (302), a proximal outer sheath (304), and an articulation section (310) configured to operate substantially similar to articulation sections (130, 210) discussed above except for the differences discussed below. In particular, articulation section (310) is operable to selectively position end effector (340) at various lateral deflection angles relative to a longitudinal axis defined by proximal outer sheath (304). End effector (340) includes an ultrasonic blade (342) and a pivoting clamp arm (344) having a clamp pad (345). End effector (340) is configured to operate substantially similar to end effectors (40, 240) discussed above except for the differences discussed below. In particular, clamp arm (344) of end effector (340) is operable to compress tissue against blade (342). When blade (342) is activated while clamp arm (344) compresses tissue against blade (342), end effector (340) simultaneously severs the tissue and denatures the proteins in adjacent tissue cells, thereby providing a coagulative effect.

Clamp arm (344) is operable to selectively pivot toward and away from blade (342) to selectively clamp tissue between clamp pad (345) and blade (342). Clamp arm (344) is pivotably secured to an upper distal end of a distal outer sheath (302) via a pin (322). A pair of arms (347) extend transversely from clamp arm (344) and are pivotably secured to a collar (320) via a pin (324). Collar (320) is slidably disposed within distal outer sheath (302). Thus, it should be understood that longitudinal movement of collar (320) within distal outer sheath (302) causes pivoting of clamp arm (344) about pin (322) toward and away from blade (342).

Figure 13A:
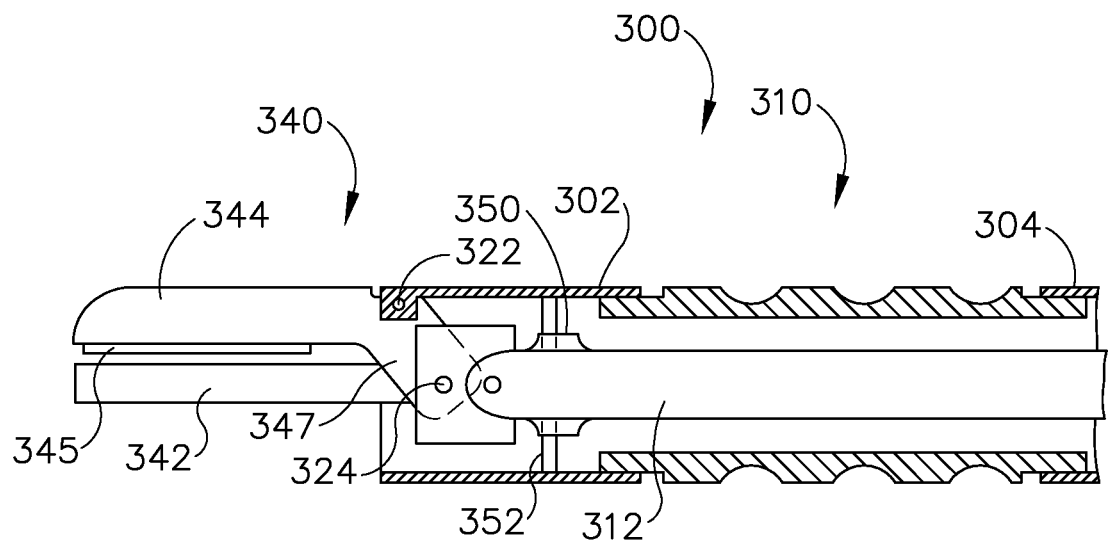
FIG. 13A depicts a side elevational view of yet another exemplary alternative end effector and the distal portion of a shaft assembly and end effector, configured for incorporation in the instrument of FIG. 1, with a clamp arm of the end effector in a closed position, and with the shaft assembly shown in side cross-section.
Figure 13B:
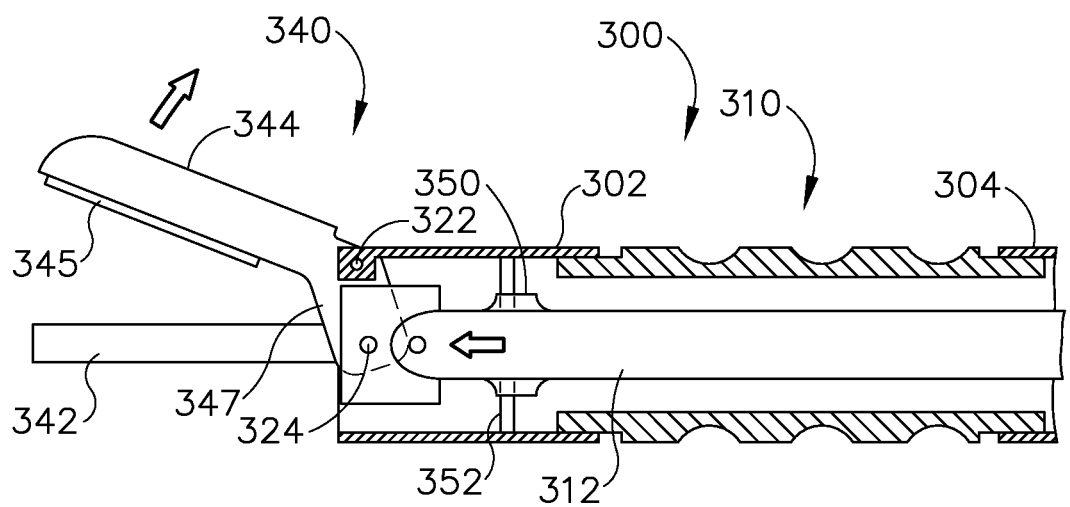
FIG. 13B depicts a side elevational view of the shaft assembly and end effector of FIG. 13A, with the clamp arm moved to an open position, and with the shaft assembly shown in side cross-section.

Blade (342) is positioned at the distal end of an acoustic drivetrain, which passes through an inner bore of collar (320) without contacting collar (320). This acoustic drivetrain includes a transducer assembly (not shown) and an acoustic waveguide (346). Waveguide (346) comprises a flexible portion (348). Flexible portion (348) of waveguide (346) includes a distal flange (350), a proximal flange (not shown), and a narrowed section (349) located between distal flange (350) and the proximal flange. In the present example, distal flange (350) and the proximal flange are located at positions corresponding to nodes associated with resonant ultrasonic vibrations communicated through flexible portion (348) of waveguide (346). Narrowed section (349) is configured to allow flexible portion (348) of waveguide (346) to flex without significantly affecting the ability of flexible portion (348) of waveguide (346) to transmit ultrasonic vibrations. As best seen in FIGS. 13A and 13B, distal flange (350) is secured to distal outer sheath (302) via a pin (352). Distal outer sheath (302) is thereby mechanically grounded to an instrument body (e.g., handle assembly (20), etc.) via waveguide (346).

Figure 14A:
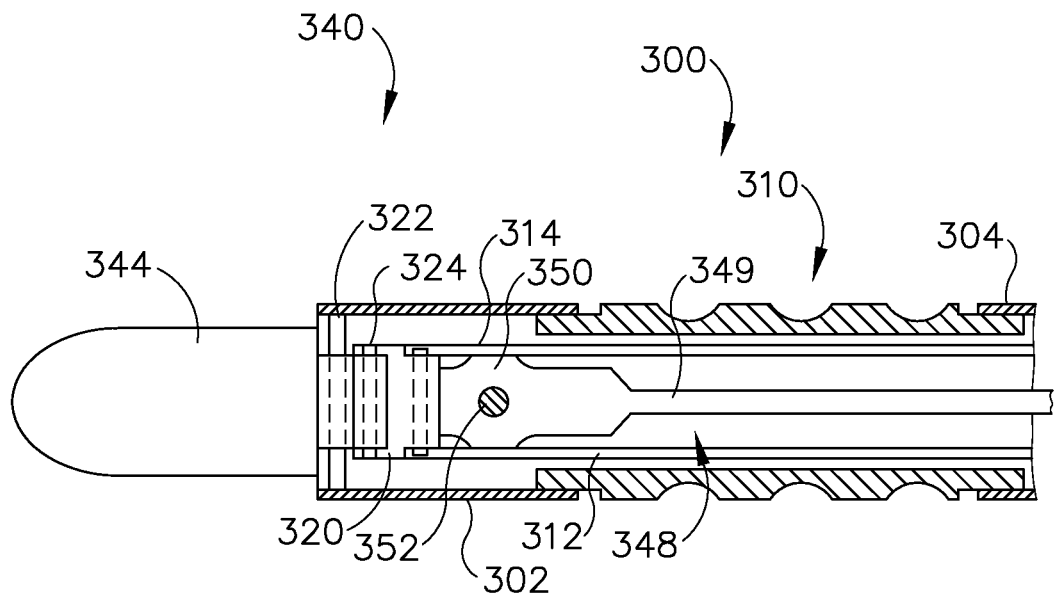
FIG. 14A depicts a top plan view of the shaft assembly and end effector of FIG. 13A in a substantially straight configuration, with the shaft assembly shown in top cross-section.
Figure 14B:
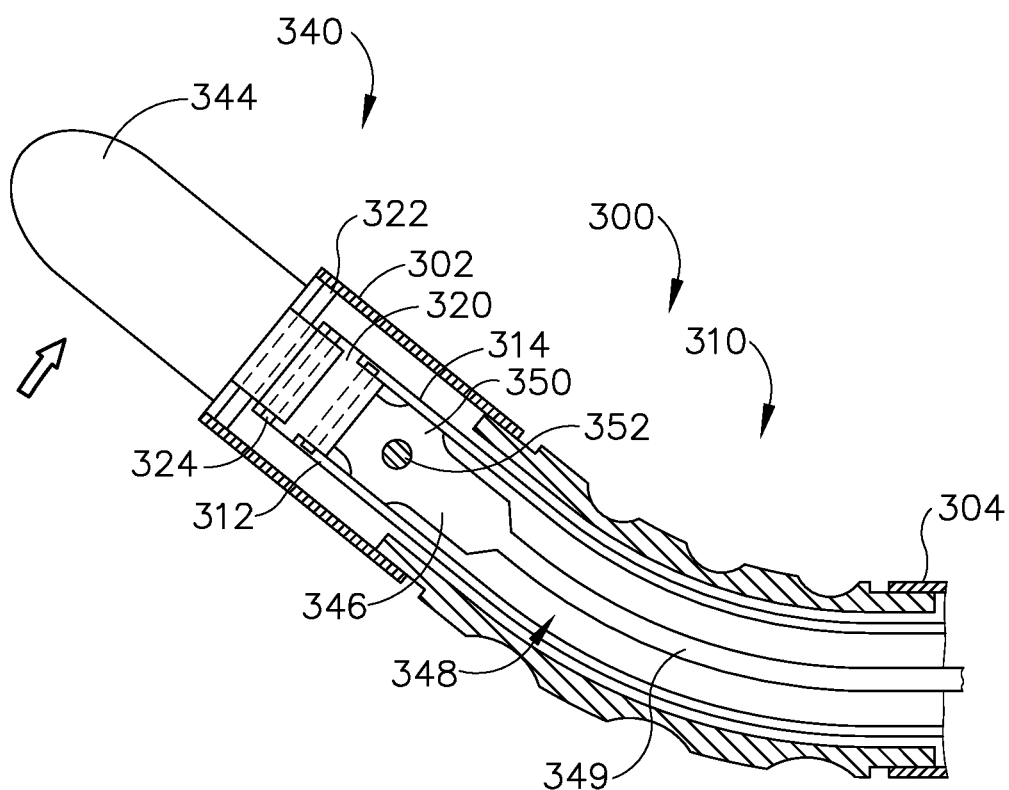
FIG. 14B depicts a top plan view of the shaft assembly and end effector of FIG. 13A in an articulated configuration, with the shaft assembly shown in top cross-section.

Shaft assembly (300) further comprises a pair of articulation bands (312, 314). Distal ends of articulation bands (312, 314) are secured to collar (320). Articulation bands (312, 314) are configured to operate substantially similar to articulation bands (140, 142, 212, 214) discussed above except for the differences discussed below. In particular, as shown in FIGS. 14A-14B, opposing longitudinal motion of articulation bands (312, 314) causes articulation of articulation section (310). Distal ends of articulation bands (312, 314) are secured to collar (320). When articulation bands (312, 314) are translated longitudinally in an opposing fashion, a moment is created and applied to a distal end of distal outer sheath (302) via pin (322), arms (347) of clamp arm (344), pin (324), and collar (320). This causes articulation section (310) and narrowed section (349) of flexible portion (348) of waveguide (346) to articulate, without transferring axial forces in articulation bands (312, 314) to waveguide (346).

As shown in FIGS. 13A-13B, when articulation bands (312, 314) are both translated in the same direction simultaneously, this simultaneous longitudinal movement of articulation bands (312, 314) causes concurrent longitudinal movement of collar (320) relative to distal outer sheath (302) and the other grounded components of shaft assembly (300). Thus, the simultaneous longitudinal motion of articulation bands (312, 314) in the same direction causes pivoting of clamp arm (344) toward and away from ultrasonic blade (342). It should therefore be understood that opposing longitudinal motion of articulation bands (312, 314) will cause articulation of articulation section (310); distal movement of both articulation bands (312, 314) simultaneously will cause clamp arm (344) to pivot away from blade (342); and proximal movement of both articulation bands (312, 314) simultaneously will cause clamp arm (344) to pivot toward blade (342).

Articulation bands (312, 314) may be driven to translate in an opposing fashion by a modified version of articulation control assembly (100). Articulation bands (312, 314) may be driven to translate in the same direction simultaneously by a modified version of trigger (28). For instance, pivoting of trigger (28) toward and away from pistol grip (24) may cause the entire modified articulation control assembly (100) to translate, which may thereby cause both articulation bands (312, 314) to translate simultaneously in the same direction. Various suitable ways in which articulation control assembly (100) and trigger (28) may be modified and coupled together will be apparent to those of ordinary skill in the art in view of the teachings herein. Similarly, other suitable ways in which articulation bands (312, 314) may be driven (in an opposing fashion and/or simultaneously in the same direction) will be apparent to those of ordinary skill in the art in view of the teachings herein.

E. Exemplary Alternative End Effector and Shaft Assembly Configuration with Clamp Arm Ball Joint FIGS. 15A-16B show yet another exemplary alternative shaft assembly (400) and end effector (440) that may be readily incorporated into instrument (10). Shaft assembly (400) comprises a distal outer sheath (402), a proximal outer sheath (404), and an articulation section (410) configured to operate substantially similar to articulation sections (130, 210, 310) discussed above except for the differences discussed below. In particular, articulation section (410) is operable to selectively position end effector (440) at various lateral deflection angles relative to a longitudinal axis defined by proximal outer sheath (404). End effector (440) includes an ultrasonic blade (442) and a pivoting clamp arm (444) having a clamp pad (445). End effector (440) is configured to operate substantially similar to end effectors (40, 240, 340) discussed above except for the differences discussed below. In particular, clamp arm (444) of end effector (440) is operable to compress tissue against blade (442). When blade (442) is activated while clamp arm (444) compresses tissue against blade (442), end effector (440) simultaneously severs the tissue and denatures the proteins in adjacent tissue cells, thereby providing a coagulative effect.

Figure 15A:
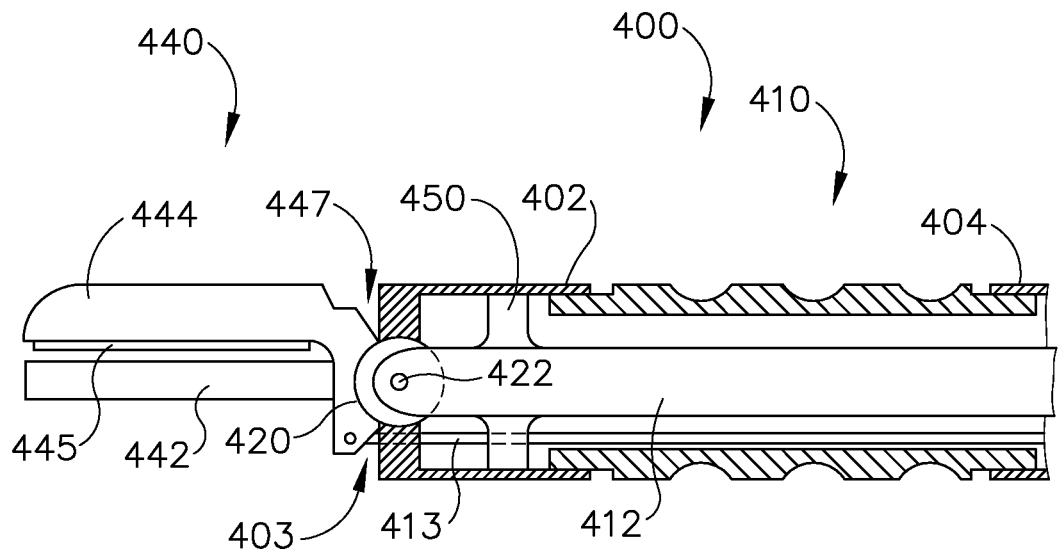
FIG. 15A depicts a side elevational view of yet another exemplary alternative end effector and the distal portion of a shaft assembly and end effector, configured for incorporation in the instrument of FIG. 1, with a clamp arm of the end effector in a closed position, and with the shaft assembly shown in side cross-section.
Figure 15B:
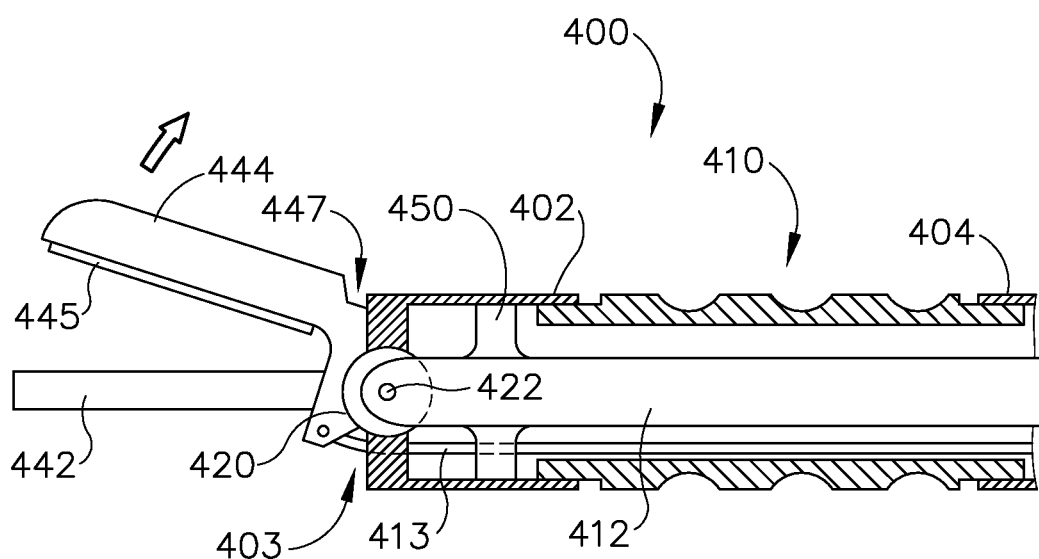
FIG. 15B depicts a side elevational view of the shaft assembly and end effector of FIG. 15A, with the clamp arm moved to an open position, and with the shaft assembly shown in side cross-section.

Clamp arm (444) is operable to selectively pivot toward and away from blade (442) to selectively clamp tissue between clamp pad (445) and blade (442). A proximal end of clamp arm (444) comprises a socket (447) configured to engage a sphere-shaped collar (420). A distal end of distal outer sheath (402) comprises a socket (403) that is also configured to engage sphere-shaped collar (420), such that sphere-shaped collar (420) is captured between sockets (403, 447). In other words, clamp arm (444), sphere-shaped collar (420), and distal outer sheath (402) engage one another in a ball-and-socket-like relationship. The proximal end of clamp arm (444) is pivotably coupled with sphere-shaped collar (420) and distal outer sheath (402) via a pin (422). Thus, it should be understood that clamp arm (444) is operable to rotate about pin (422), along sphere-shaped collar (420), toward and away from blade (442). A bottom portion of clamp arm (444) is pivotably coupled within a distal end of a rod (413). Rod (413) is slidably disposed within shaft assembly (400) such that rod (413) is freely translatable relative to articulation section (410). Thus, it should be understood that longitudinal movement of rod (413) causes pivoting of clamp arm (444) toward and away from blade (442) as shown in FIGS. 15A-15B. Rod (413) is coupled with a trigger (not shown) such that clamp arm (444) is pivotable toward and away from ultrasonic blade (442) in response to pivoting, sliding, or other actuation of the trigger.

Blade (442) is positioned at the distal end of an acoustic drivetrain, which passes through an inner bore of collar (420) without contacting collar (420). This acoustic drivetrain includes a transducer assembly (not shown) and an acoustic waveguide (446). Waveguide (446) comprises a flexible portion (448). Flexible portion (448) of waveguide (446) includes a distal flange (450), a proximal flange (not shown), and a narrowed section (449) located between distal flange (450) and the proximal flange. In the present example, distal flange (450) and the proximal flange are located at positions corresponding to nodes associated with resonant ultrasonic vibrations communicated through flexible portion (448) of waveguide (446). Narrowed section (449) is configured to allow flexible portion (448) of waveguide (446) to flex without significantly affecting the ability of flexible portion (448) of waveguide (446) to transmit ultrasonic vibrations. As best seen in FIG. 15A-15B, distal flange (450) engages an interior surface of distal outer sheath (402). In some versions, a gap is defined between distal flange (450) and the interior surface of distal outer sheath (402). In some other versions, a dampening element such as an o-ring is interposed between distal flange (450) and the interior surface of distal outer sheath (402).

Figure 16A:
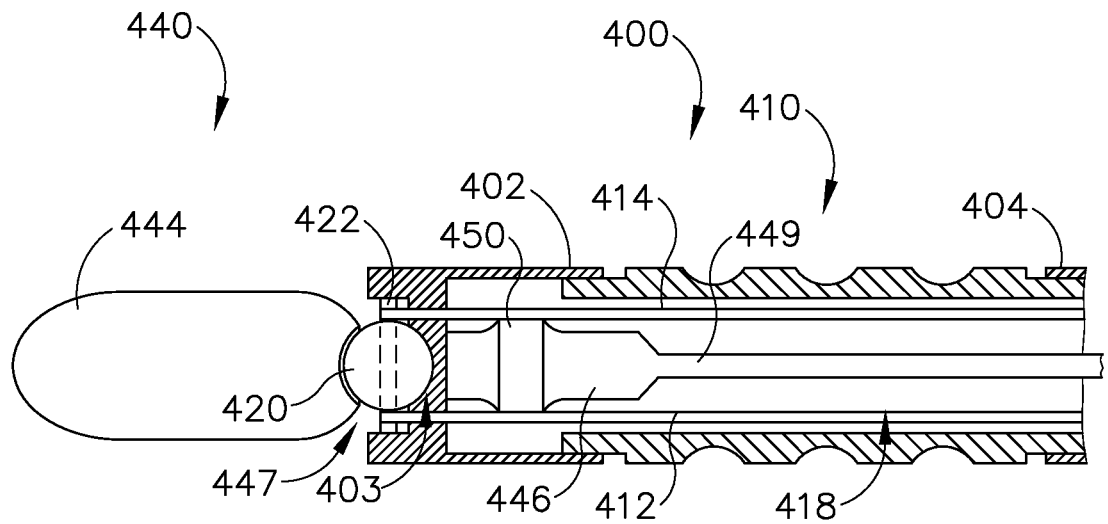
FIG. 16A depicts a top plan view of the shaft assembly and end effector of FIG. 15A in a substantially straight position, with the shaft assembly shown in top cross-section.
Figure 16B:
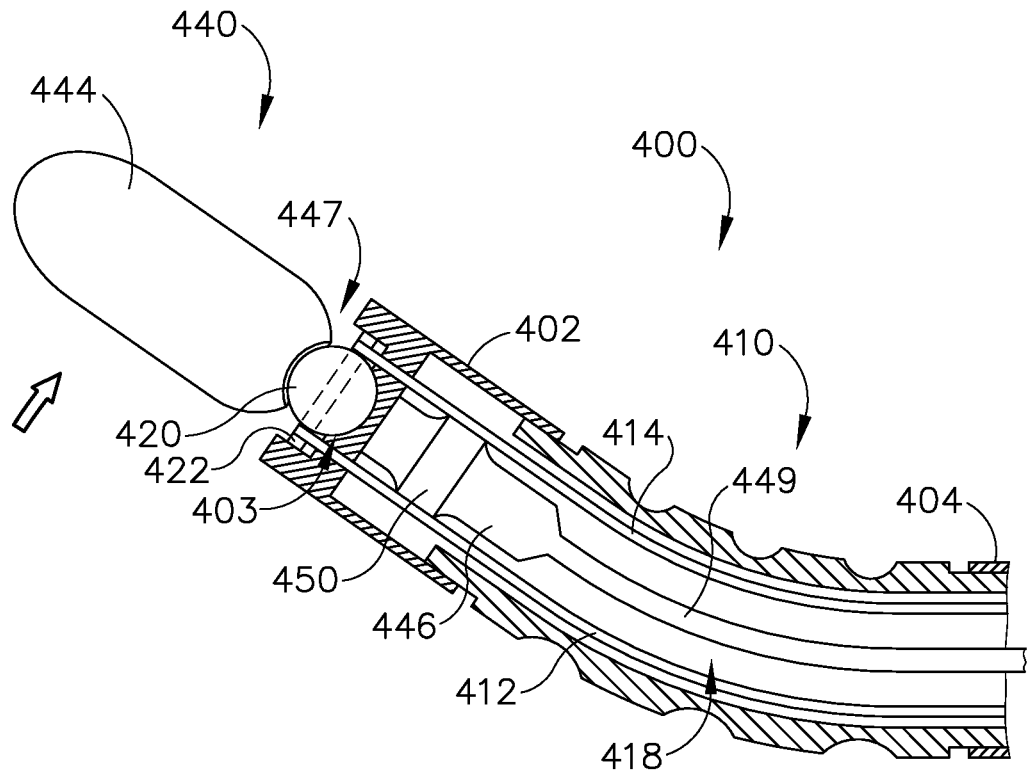
FIG. 16B depicts a top plan view of the shaft assembly and end effector of FIG. 15A moved into a bent configuration, with the shaft assembly shown in top cross-section.

Shaft assembly (400) further comprises a pair of articulation bands (412, 414). Distal ends of articulation bands (412, 414) are secured to distal outer sheath (402) and collar (420) via pin (422). Articulation bands (412, 414) are configured to operate substantially similar to articulation bands (140, 142, 212, 214, 312, 314) discussed above except for the differences discussed below. In particular, as shown in FIGS. 16A and 16B, opposing longitudinal motion of articulation bands (412, 414) is configured to cause articulation of articulation section (410). When articulation bands (412, 414) are translated longitudinally in an opposing fashion, a moment is created and applied to a distal end of distal outer sheath (402) via pin (422). This causes articulation section (410) and narrowed section (449) of flexible portion (448) of waveguide (446) to articulate, without transferring axial forces in articulation bands (412, 414) to waveguide (446). Articulation bands (212, 214) may be driven to translate in an opposing fashion by a version of articulation control assembly (100) or by any other suitable drive mechanism.

F. Fourth Exemplary Alternative End Effector and Shaft Assembly Configuration

Figure 17A:
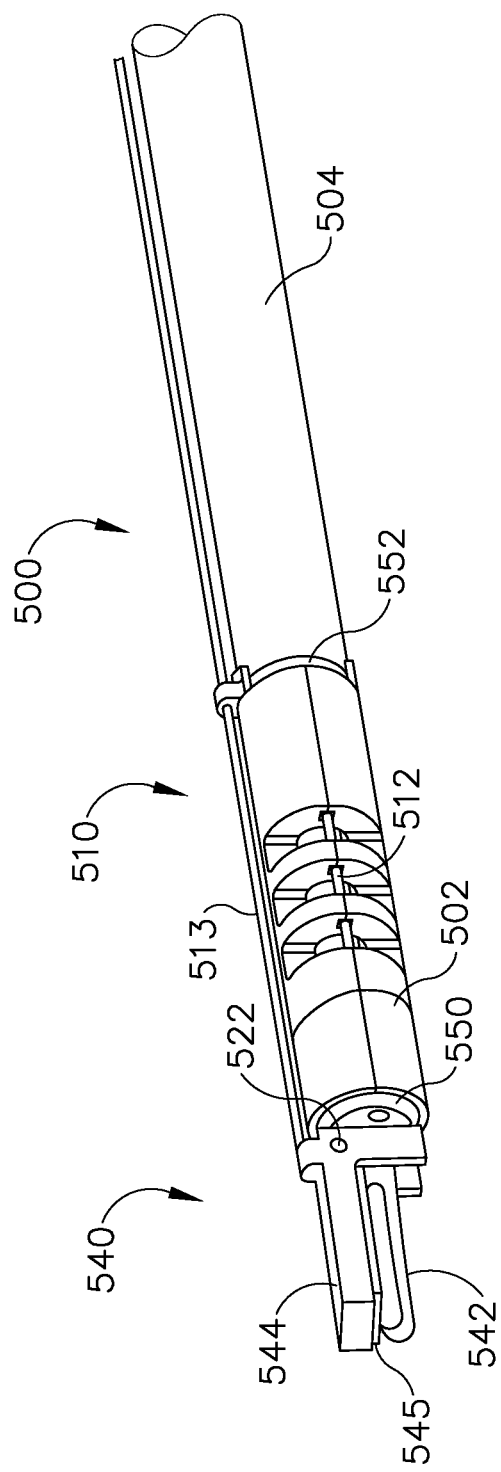
FIG. 17A depicts a perspective view of yet another exemplary alternative end effector and the distal portion of a shaft assembly and end effector, configured for incorporation in the instrument of FIG. 1, with a clamp arm of the end effector in a closed position.
Figure 17B:
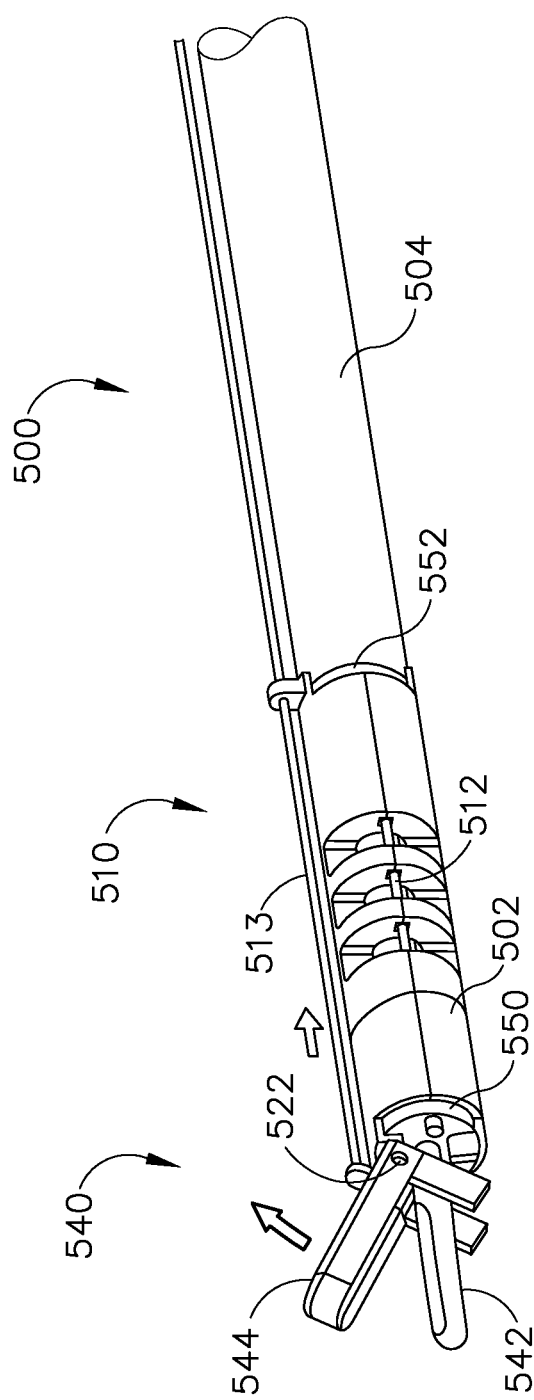
FIG. 17B depicts a perspective view of the shaft assembly and end effector of FIG. 17A, with the clamp arm moved to an open position.
Figure 18:
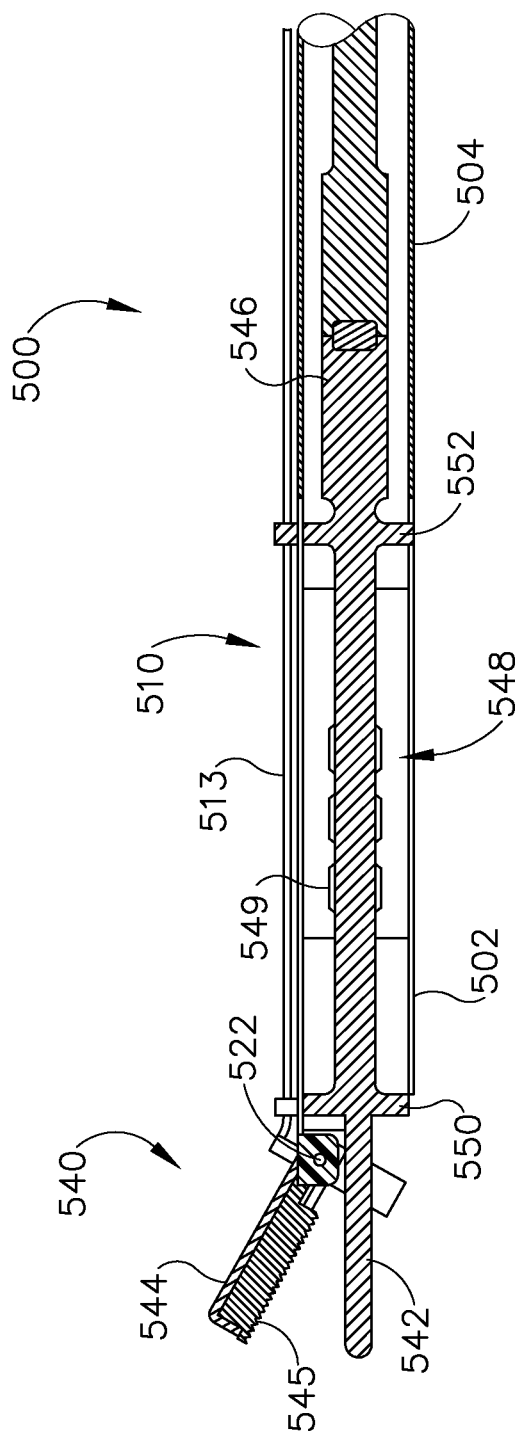
FIG. 18 depicts a side cross-sectional view of the shaft assembly and end effector of FIG. 17A, with the clamp arm in the open position.

FIGS. 17A-18 show yet another exemplary alternative shaft assembly (500) and end effector (540) that may be readily incorporated into instrument (10). Shaft assembly (500) comprises a distal outer sheath (502), a proximal outer sheath (504), and an articulation section (510) configured to operate substantially similar to articulation sections (130, 210, 310, 410) discussed above except for the differences discussed below. In particular, articulation section (510) is operable to selectively position end effector (540) at various lateral deflection angles relative to a longitudinal axis defined by proximal outer sheath (504). End effector (540) includes an ultrasonic blade (542) and a pivoting clamp arm (544) having a clamp pad (545). End effector (540) is configured to operate substantially similar to end effectors (50, 240, 340, 440) discussed above except for the differences discussed below. In particular, clamp arm (544) of end effector (540) is operable to compress tissue against blade (542). When blade (542) is activated while clamp arm (544) compresses tissue against blade (542), end effector (540) simultaneously severs the tissue and denatures the proteins in adjacent tissue cells, thereby providing a coagulative effect.

Clamp arm (544) is operable to selectively pivot toward and away from blade (542) to selectively clamp tissue between clamp pad (545) and blade (542). Clamp arm (544) is pivotably secured to an upper distal end of a distal outer sheath (502) via a pin (522). A top portion of clamp arm (544) is pivotably coupled within a distal end of a rod (513). Rod (513) is slidably secured to a top of shaft assembly (500) such that rod (513) is freely translatable relative to articulation section (510). Thus, it should be understood that longitudinal movement of rod (513) causes rotation of clamp arm (544) toward and away from blade (542). Rod (513) is coupled with a trigger (not shown) such that clamp arm (544) is pivotable toward and away from ultrasonic blade (542) in response to pivoting, sliding, or other actuation of the trigger.

Blade (542) is positioned at the distal end of an acoustic drivetrain. This acoustic drivetrain includes a transducer assembly (not shown) and an acoustic waveguide (546). Waveguide (546) comprises a flexible portion (548). Flexible portion (548) of waveguide (546) includes a distal flange (550), a proximal flange (552), and a narrowed section (549) located between flanges (550, 552). In the present example, flanges (550, 552) are located at positions corresponding to nodes associated with resonant ultrasonic vibrations communicated through flexible portion (548) of waveguide (546). Narrowed section (549) is configured to allow flexible portion (548) of waveguide (546) to flex without significantly affecting the ability of flexible portion (548) of waveguide (546) to transmit ultrasonic vibrations. It should be understood that rod (513) will also flex with flexible portion (548) when articulation section (510) is bent to an articulated state.

Shaft assembly (500) further comprises a pair of articulation cables (512). While only one articulation cable (512) is shown, it should be understood that another articulation cable (512) would be positioned on the other side of shaft assembly (500), 180° from the articulation cable (512) that is shown. The distal ends of articulation cables (512) are secured to distal flange (550) of waveguide (546). Articulation cables (512) are configured to operate substantially similar to articulation bands (140, 142, 212, 214, 312, 314, 412, 414) discussed above except for the differences discussed below. Opposing longitudinal motion of articulation cables (512) is configured to cause articulation of articulation section (510). Articulation cables (512) are secured to distal outer sheath (502) via a collar (520). When articulation cables (512) are translated longitudinally in an opposing fashion, a moment is created and applied to a distal end of distal outer sheath (502) via distal flange (550). This causes articulation section (510) and narrowed section (549) of flexible portion (548) of waveguide (546) to articulate, without transferring axial forces in articulation cables (512) to waveguide (546). Articulation bands (212, 214) may be driven to translate in an opposing fashion by a version of articulation control assembly (100) or by any other suitable drive mechanism.

In some versions of shaft assembly (500), shaft assembly includes an additional outer sheath that is disposed about outer sheaths (502, 504) and articulation section (510). In some such versions, clamp arm (544) is pivotally coupled with this additional outer sheath instead of being pivotally coupled with distal outer sheath (502). Rod (513) may be further coupled with this additional outer sheath such that rod (513) may translate relative to the additional outer sheath to pivot clamp arm (544) toward and away from blade (542). This additional outer sheath may be rotated relative to outer sheaths (502, 504) and articulation section (510). For instance, the additional outer sheath may include a knob to provide such rotation (e.g., in addition to or in lieu of a knob that provides rotation of the entire shaft assembly (500) as a unit). The additional outer sheath may also be configured to flex at articulation section (510), such that the additional outer sheath does not significantly impede the ability of articulation section (510) to achieve an articulated state. By way of example only, the additional outer sheath may be formed of a thin metal tube (e.g., approximately 0.002 inches thick) with laser cut features (e.g., a pattern of slots) that enable flexing at articulation section (510).

In versions where an additional outer sheath is provided as described above, clamp arm (544) and rod (513) may rotate with the additional outer sheath relative to outer sheaths (502, 504) and articulation section (510). Thus, the additional outer sheath may be used to rotate clamp arm (544) about the longitudinal axis of shaft assembly (500) to provide clamp arm (544) at different orbital orientations about blade (542). In versions of blade (542) that have a non-circular cross-sectional profile, this ability to orient clamp arm (544) may enable the operator to select a specific orientation that is particularly suited for the task at hand. For instance, the operator may orient clamp arm (544) to face a relatively broad flat face of blade (542) in order to provide relatively greater hemostasis in tissue compressed between clamp arm (544) and blade (542); or orient clamp arm (544) to face a relatively narrow edge region of blade (542) in order to provide relatively faster cutting of tissue compressed between clamp arm (544) and blade (542). Other suitable configurations and relationships will be apparent to those of ordinary skill in the art in view of the teachings herein. Similarly, other suitable ways in which an additional outer sheath may be formed and incorporated into shaft assembly (500) will be apparent to those of ordinary skill in the art in view of the teachings herein. While this additional outer sheath is described in the context of shaft assembly (500), it should be understood that such an additional outer sheath may also be incorporated into various other shaft assemblies described herein.

II. EXEMPLARY ALTERNATIVE SHAFT ASSEMBLY PROFILES

It may be desirable to change the profiles the components of shaft assembly (30). For instance, among other reasons, it may be desirable to change the profiles of the components of shaft assembly (30) to provide for more clearance within shaft assembly (30) while still enclosing the contents of shaft assembly (30) within an outer sheath. As will be discussed in more detail below, FIGS. 19-27 show various examples of how the profiles of the components of shaft assembly (30) may be changed. While various examples of how the profiles of the components of shaft assembly (30) may be changed will be described in greater detail below, other examples will be apparent to those of ordinary skill in the art according to the teachings herein. It should be understood that the examples of shaft assemblies and/or articulation sections described below may function substantially similar to shaft assembly (30) discussed above.

Figure 19:
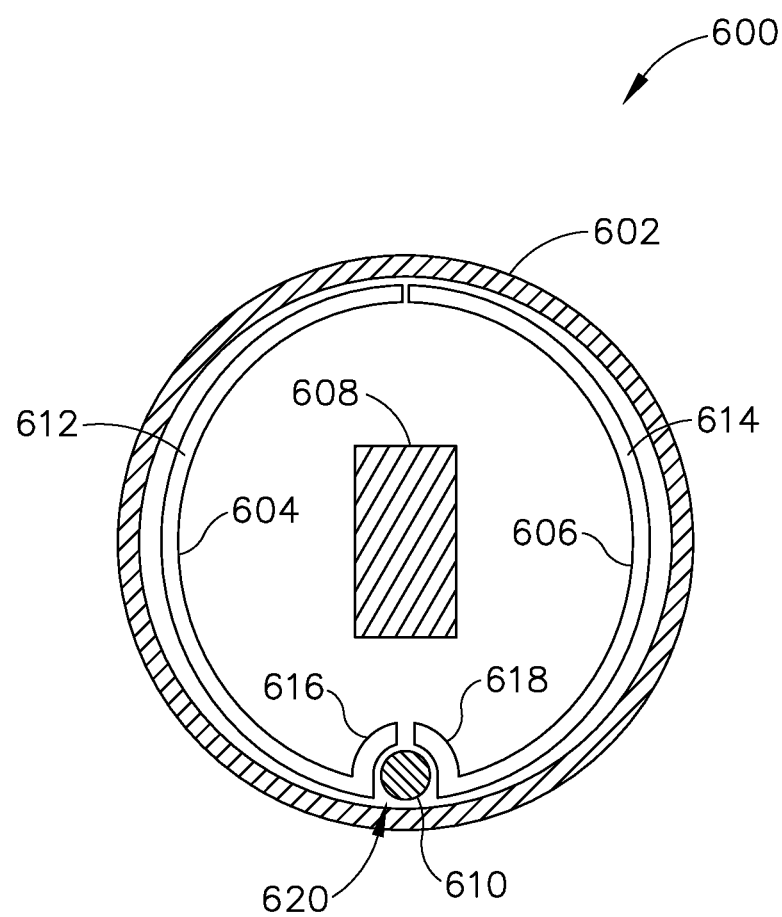
FIG. 19 depicts a front cross-sectional end view of yet another exemplary alternative shaft assembly and end effector, configured for incorporation in the instrument of FIG. 1.

A. Exemplary Alternative Shaft Assembly Profile with Bands Defining Channels FIG. 19 shows an exemplary alternative profile of yet another exemplary alternative shaft assembly (600) that may be used as a substitute for shaft assembly (30) in instrument (10). Shaft assembly (600) of this example comprises an outer sheath (602), a pair of articulation bands (604, 606), a waveguide (608), and a drive rod (610). Articulation bands (604, 606) are configured to operate substantially similar to articulation bands (140, 142), such that opposing longitudinal motion of articulation bands (604, 606) causes articulation of shaft assembly (600). Rod (610) is configured to operate substantially similar to cable (174) discussed above, such that longitudinal translation of rod (610) causes actuation of a clamp arm (not shown).

Outer sheath (602) has a circular cross-sectional profile. Each articulation band (604, 606) comprises a large semi-circular portion (612, 614) and a small semi-circular portion (616, 618). Small semi-circular portions (616, 618) extend inwardly from large semi-circular portions (612, 614). Articulation bands (604, 606) are arranged within outer sheath (602) such that small semi-circular portions (616, 618) are adjacent to one another, and form a channel (620) therebetween. Rod (610) is slidably disposed within channel (620) and is configured to longitudinally translate within channel (620) to thereby actuate the clamp arm. In the cross-sectional region shown in FIG. 19, waveguide (608) has a rectangular profile and passes within outer sheath (602) between articulation bands (604, 606). It should be understood that waveguide (608) may have any other suitable cross-sectional profile that fits within the space defined between articulation bands (604, 606). Moreover, the cross-sectional profile of waveguide (608) may vary along the length of waveguide (608).

Figure 20:
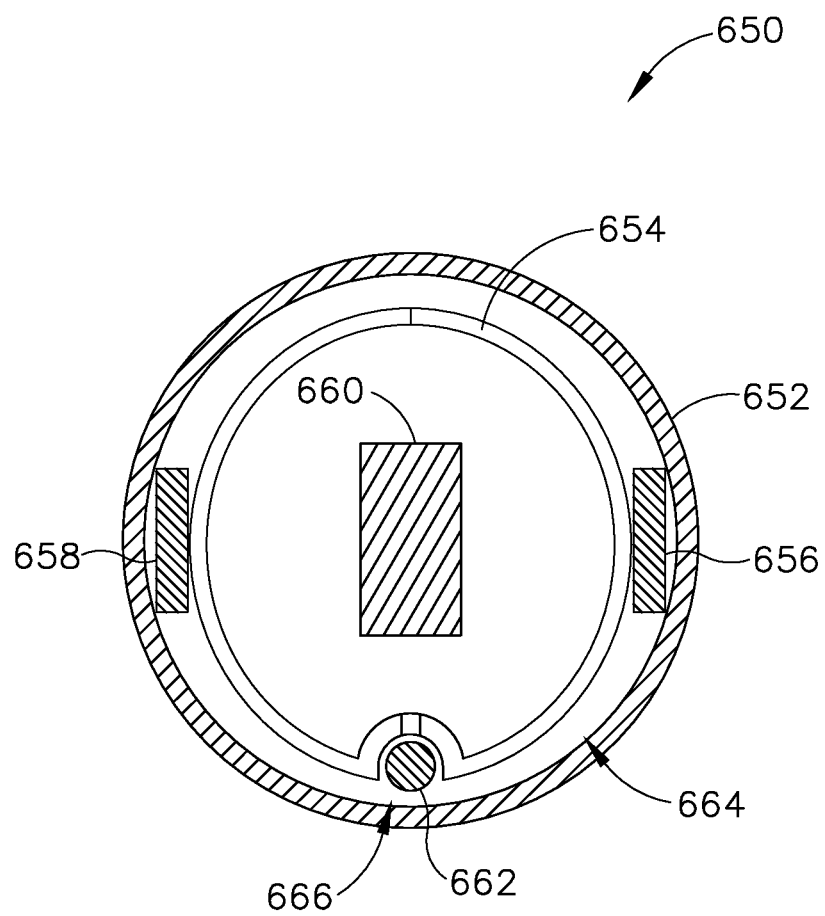
FIG. 20 depicts a front cross-sectional end view of yet another exemplary alternative shaft assembly and end effector, configured for incorporation in the instrument of FIG. 1.

B. Exemplary Alternative Shaft Assembly Profile Drive Features Between Inner Tube and Outer Tube FIG. 20 shows another exemplary alternative profile of yet another exemplary alternative shaft assembly (650) that may be used as a substitute for shaft assembly (30) in instrument (10). Shaft assembly (650) of this example comprises an outer sheath (652), an inner tube (654), a pair of articulation bands (656, 658), a waveguide (660), and a drive rod (662). Articulation bands (656, 658) are configured to operate substantially similar to articulation bands (140, 142), such that opposing longitudinal motion of articulation bands (656, 658) causes articulation of shaft assembly (650). Rod (662) is configured to operate substantially similar to cable (174) discussed above, such longitudinal translation of rod (662) actuates a clamp arm (not shown).

Outer sheath (652) has a circular cross-sectional profile. Inner tube (654) is slidably disposed within outer sheath (652) such that a space (664) is defined between an interior surface of outer sheath (652) and an exterior surface of inner tube (654). Articulation bands (656, 658) are slidably disposed within space (664) between inner tube (654) and outer tube (652). A semi-circular channel (666) is formed in the exterior surface of inner tube (654). Rod (662) is slidably disposed within channel (666) and is configured to longitudinally translate within channel (666) to thereby actuate the clamp arm. In the cross-sectional region shown in FIG. 20, waveguide (660) has a rectangular profile and passes within inner tube (654). It should be understood that waveguide (660) may have any other suitable cross-sectional profile that fits within the space defined within inner tube (654). Moreover, the cross-sectional profile of waveguide (660) may vary along the length of waveguide (660).

Figure 21:
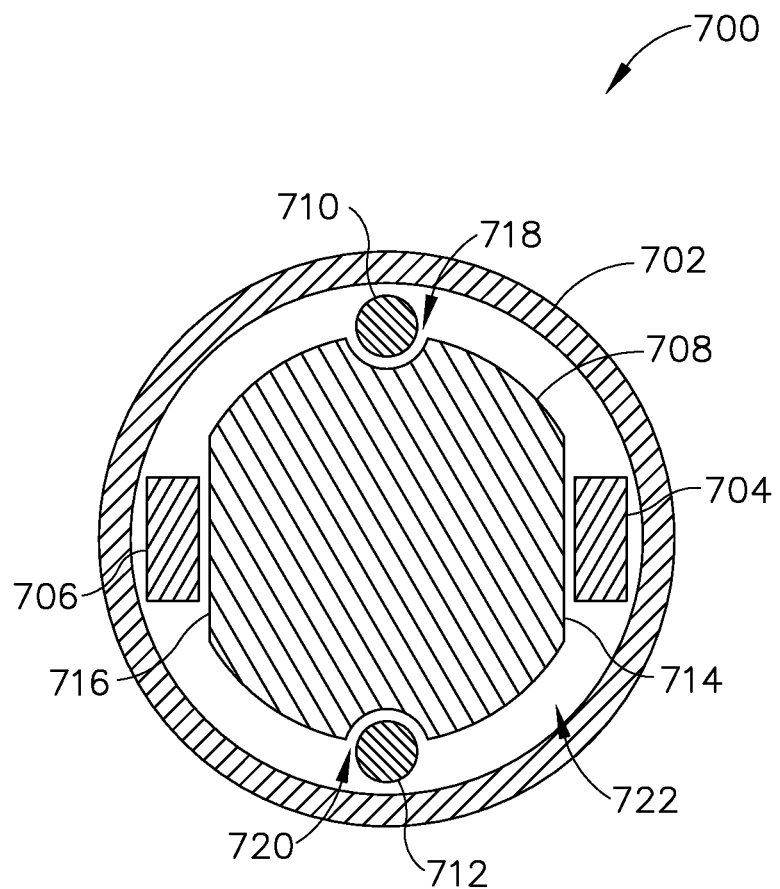
FIG. 21 depicts a front cross-sectional end view of yet another exemplary alternative shaft assembly and end effector, configured for incorporation in the instrument of FIG. 1.

C. Exemplary Alternative Shaft Assembly Profile with Waveguide Defining Channels and Dual Rods FIG. 21 shows yet another exemplary alternative profile of yet another exemplary alternative shaft assembly (700) that may be used as a substitute for shaft assembly (30) in instrument (10). Shaft assembly (700) of this example comprises an outer sheath (702), a pair of articulation bands (704, 706), a waveguide (708), and a pair of rods (710, 712). Articulation bands (704, 706) are configured to operate substantially similar to articulation bands (140, 142) discussed above, such that opposing longitudinal motion of articulation bands (704, 706) causes articulation of shaft assembly (700). Rods (710, 712) are configured to operate substantially similar to cable (174), such that longitudinal translation of rods (710, 712) provides actuation of a clamp arm (not shown). For instance, rod (710) may translate proximally while the other rod (712) translates distally to pivot a clamp arm away from an ultrasonic blade; and rod (710) may translate distally while the other rod (712) translates proximally to pivot the clamp arm toward the ultrasonic blade. Various suitable ways in which rods (710, 712) may be driven in such an opposing fashion will be apparent to those of ordinary skill in the art in view of the teachings herein. In some other versions, one of the rods (710, 712) is substituted with one or more wires that is/are configured to provide RF electrosurgical capabilities at an end effector that is at the distal end of shaft assembly (700).

Outer sheath (702) has a circular cross-sectional profile. Waveguide (708) has a generally circular cross-sectional profile with a pair of flats (714, 716) and a pair of semi-circular channels (718, 720) defined within an exterior surface of waveguide (708). Rods (710, 712) are slidably disposed within respective channels (718, 720) and are configured to longitudinally translate within channels (718, 720) to thereby actuate the clamp arm. Waveguide (708) is disposed within outer sheath (702) such that a space (722) is defined between an interior surface of outer sheath (702) and an exterior surface of waveguide (708). Articulation bands (704, 706) are slidably disposed within space (722) between outer sheath (702) and waveguide (708) adjacent to flats (714, 716) and are configured to longitudinally translate within space (722) to thereby cause articulation of shaft assembly (700).

Figure 22:
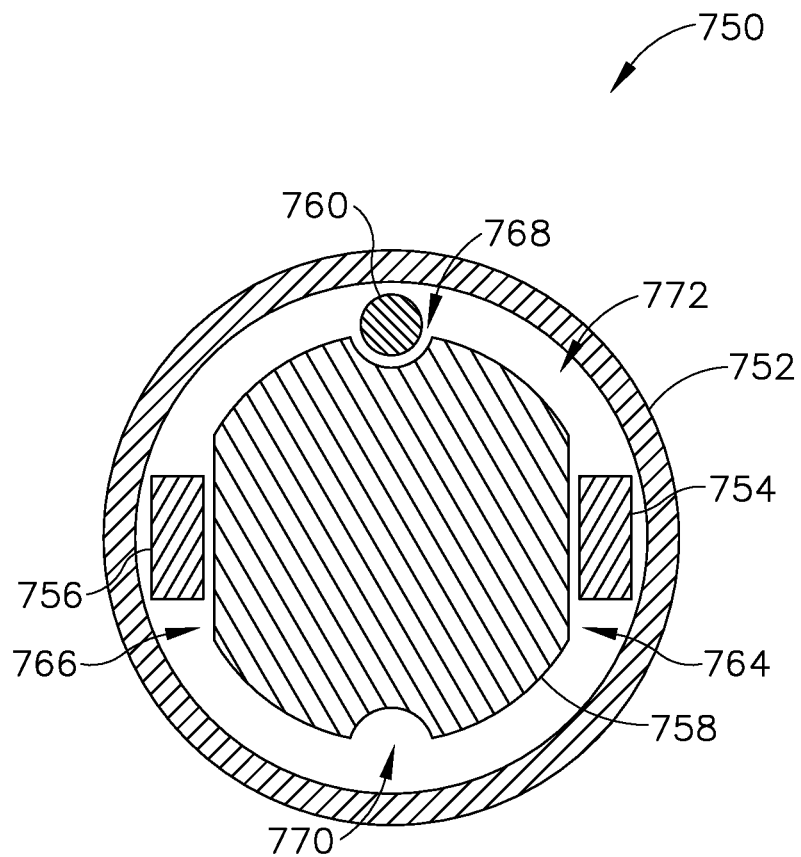
FIG. 22 depicts a front cross-sectional end view of yet another exemplary alternative shaft assembly and end effector, configured for incorporation in the instrument of FIG. 1.

D. Exemplary Alternative Shaft Assembly Profile with Waveguide Defining Channels and Single Upper Rod FIG. 22 shows yet another exemplary alternative profile of yet another exemplary alternative shaft assembly (750) that may be used as a substitute for shaft assembly (30) in instrument (10). Shaft assembly (750) of this example comprises an outer sheath (752), a pair of articulation bands (754, 756), a waveguide (758), and a rod (760). Articulation bands (754, 756) are configured to operate substantially similar to articulation bands (140, 142) discussed above, such that opposing longitudinal motion of articulation bands (754, 756) causes articulation of shaft assembly (750). Rod (760) is configured to operate substantially similar to cable (174), such that longitudinal translation of rod (760) provides actuation of a clamp arm (not shown).

Outer sheath (752) has a circular cross-sectional profile. Waveguide (758) has a generally circular cross-sectional profile with a pair of flats (764, 766) and a pair of semi-circular channels (768, 770) defined within an exterior surface of waveguide (758). Waveguide (758) is disposed within outer sheath (752) such that a space (772) is defined between an interior surface of outer sheath (752) and an exterior surface of waveguide (758). Articulation bands (754, 756) are slidably disposed within space (772) between outer sheath (752) and waveguide (758) adjacent to flats (764, 766) and are configured to longitudinally translate to thereby cause articulation of shaft assembly (750). Rod (760) is slidably disposed within channel (768) and is configured to longitudinally translate within channel (768) to thereby actuate the clamp arm. In this example, no component is disposed in channel (770). Thus, channel (770) may simply be omitted if desired. Alternative, one or more wires and/or other components may be positioned in channel (770).

Figure 23:
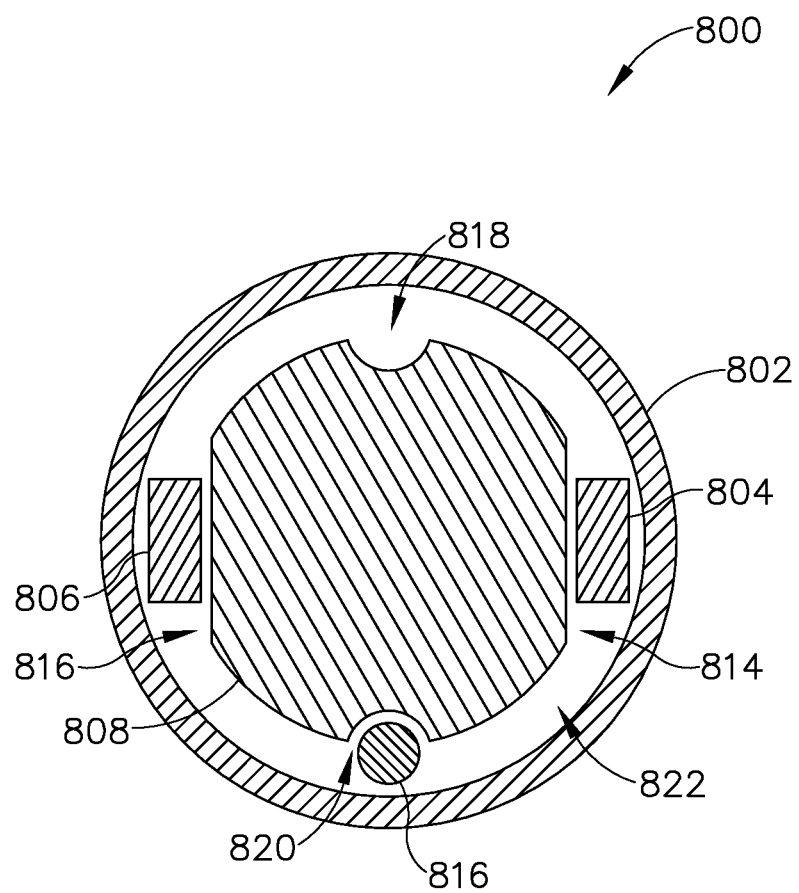
FIG. 23 depicts a front cross-sectional end view of yet another exemplary alternative shaft assembly and end effector, configured for incorporation in the instrument of FIG. 1.

E. Exemplary Alternative Shaft Assembly Profile with Waveguide Defining Channels and Single Lower Rod FIG. 23 shows yet another exemplary alternative profile of yet another exemplary alternative shaft assembly (800) that may be used as a substitute for shaft assembly (30) in instrument (10). Shaft assembly (800) of this example comprises an outer sheath (802), a pair of articulation bands (804, 806), a waveguide (808), and a rod (810). Articulation bands (804, 806) are configured to operate substantially similar to articulation bands (140, 142) discussed above, such that opposing longitudinal motion of articulation bands (804, 806) causes articulation of shaft assembly (800). Rod (810) is configured to operate substantially similar to cable (174) discussed above, such that longitudinal translation of rod (810) provides actuation of a clamp arm (not shown).

Outer sheath (802) has a circular cross-sectional profile. Waveguide (808) has a generally circular cross-sectional profile with a pair of flats (814, 816) and a pair of semi-circular channels (818, 820) defined within an exterior surface of waveguide (808). Waveguide (808) is disposed within outer sheath (802) such that a space (822) is defined between an interior surface of outer sheath (802) and an exterior surface of waveguide (808). Articulation bands (804, 806) are slidably disposed within space (822) between outer sheath (802) and waveguide (808) adjacent to flats (814, 816) and are configured to longitudinally translate to thereby cause articulation of shaft assembly (800). Rod (810) is slidably disposed within channel (820) and is configured to longitudinally translate within channel (820) to thereby actuate the clamp arm. In this example, no component is disposed in channel (818). Thus, channel (818) may simply be omitted if desired. Alternative, one or more wires and/or other components may be positioned in channel (818).

Figure 24:
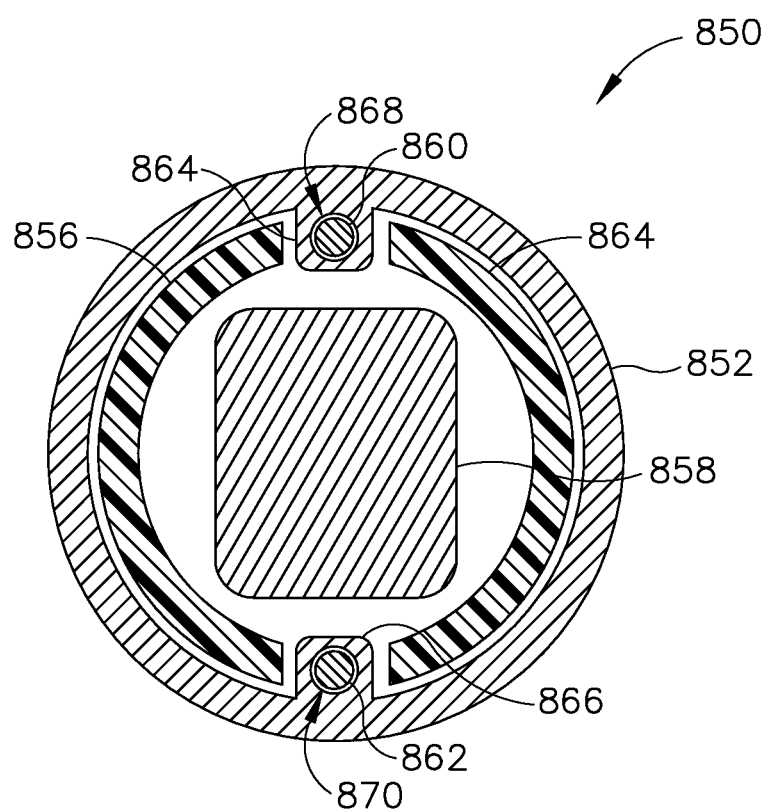
FIG. 24 depicts a front cross-sectional end view of yet another exemplary alternative shaft assembly and end effector, configured for incorporation in the instrument of FIG. 1.

F. Exemplary Alternative Shaft Assembly Profile with Outer Sheath Defining Channels for Upper and Lower Rods FIG. 24 shows yet another exemplary alternative profile of yet another exemplary alternative shaft assembly (850) that may be used as a substitute for shaft assembly (30) in instrument (10). Shaft assembly (850) of this example comprises an outer sheath (852), a pair of articulation bands (854, 856), a waveguide (858), and a pair of rods (860, 862). Articulation bands (854, 856) are configured to operate substantially similar to articulation bands (140, 142) discussed above, such that opposing longitudinal motion of articulation bands (854, 856) causes articulation of shaft assembly (850). Rods (860, 862) are configured to operate substantially similar to rods (710, 712) discussed above, such that longitudinal translation of rods (860, 862) is configured to cause rotation of a clamp arm (not shown). For instance, rod (860) may translate proximally while the other rod (862) translates distally to pivot a clamp arm away from an ultrasonic blade; and rod (860) may translate distally while the other rod (862) translates proximally to pivot the clamp arm toward the ultrasonic blade. Various suitable ways in which rods (860, 862) may be driven in such an opposing fashion will be apparent to those of ordinary skill in the art in view of the teachings herein. In some other versions, one of the rods (860, 862) is substituted with one or more wires that is/are configured to provide RF electrosurgical capabilities at an end effector that is at the distal end of shaft assembly (800).

Outer sheath (852) has a generally circular cross-sectional profile and includes a pair of inwardly extending projections (864, 866). Projections (864, 866) each define a respective through bore (868, 870). In some versions, outer sheath (852) is formed in an extrusion process (e.g., from plastic and/or metal, etc.). Of course, any suitable process may be used to form outer sheath (852). Rods (860, 862) are slidably disposed within through bores (868, 870) and are configured to longitudinally translate within through bores (868, 870) to thereby rotate the clamp arm. Articulation bands (854, 856) each have a semi-circular cross-sectional profile. Articulation bands (854, 856) are slidably disposed within outer sheath (852) between projections (864, 866) and are configured to longitudinally translate to thereby cause articulation of shaft assembly (850).

In the cross-sectional region shown in FIG. 24, waveguide (858) has a rectangular profile and passes within the space defined between articulation bands (854, 856). It should be understood that waveguide (858) may have any other suitable cross-sectional profile that fits within the space defined between articulation bands (854, 856). Moreover, the cross-sectional profile of waveguide (858) may vary along the length of waveguide (858).

Figure 25:
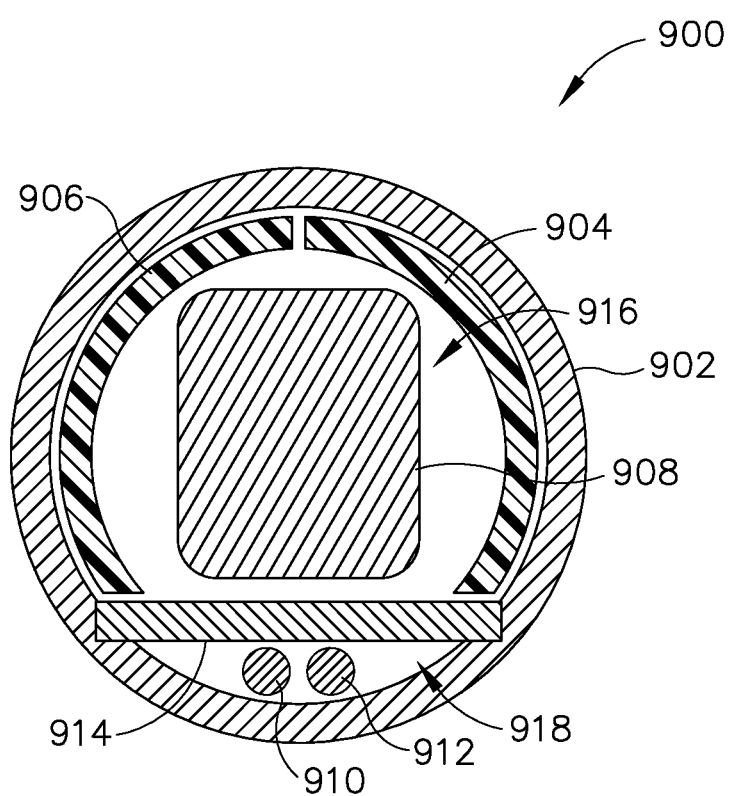
FIG. 25 depicts a front cross-sectional end view of yet another exemplary alternative shaft assembly and end effector, configured for incorporation in the instrument of FIG. 1.

G. Exemplary Alternative Shaft Assembly Profile with Outer Sheath Defining Channels for Dual Lower Rods FIG. 25 shows yet another exemplary alternative profile of yet another exemplary alternative shaft assembly (900) that may be used as a substitute for shaft assembly (30) in instrument (10). Shaft assembly (900) of this example comprises an outer sheath (902), a pair of articulation bands (904, 906), a waveguide (908), and a pair of rods (910, 912). Articulation bands (904, 906) are configured to operate substantially similar to articulation bands (140, 142) discussed above, such that opposing longitudinal motion of articulation bands (904, 906) causes articulation of shaft assembly (900). Rods (910, 912) are configured to operate substantially similar to cable (174) discussed above, such that longitudinal translation of rods (910, 912) actuates a clamp arm (not shown).

Outer sheath (902) has a circular cross-sectional profile. A partitioning member (914) extends between an interior surface of outer sheath (902) along a chord line, and divides the interior of outer sheath (902) into a first lumen (916) and a second lumen (918). Articulation bands (904, 906) each have a semi-circular profile. Articulation bands (904, 906) are slidably disposed within first lumen (916) of outer sheath (902) adjacent to one another and are configured to longitudinally translate to thereby cause articulation of shaft assembly (900). Rods (910, 912) are slidably disposed within second lumen (918) of outer sheath (902) and are configured to longitudinally translate within second lumen (918) to thereby actuate the clamp arm. In some versions, both rods (910, 912) translate longitudinally in the same direction simultaneously to actuate the clamp arm. In some other versions, rods (910, 912) translate longitudinally in an opposing fashion to actuate the clamp arm. In still other versions, one of the rods (910, 912) is substituted with one or more wires that is/are configured to provide RF electrosurgical capabilities at an end effector that is at the distal end of shaft assembly (900).

In the cross-sectional region shown in FIG. 25, waveguide (908) has a rectangular profile and passes within the space defined between articulation bands (904, 906) and partitioning member (914). It should be understood that waveguide (908) may have any other suitable cross-sectional profile that fits within the space defined between articulation bands (904, 906) and partitioning member (914). Moreover, the cross-sectional profile of waveguide (908) may vary along the length of waveguide (908).

Figure 26:
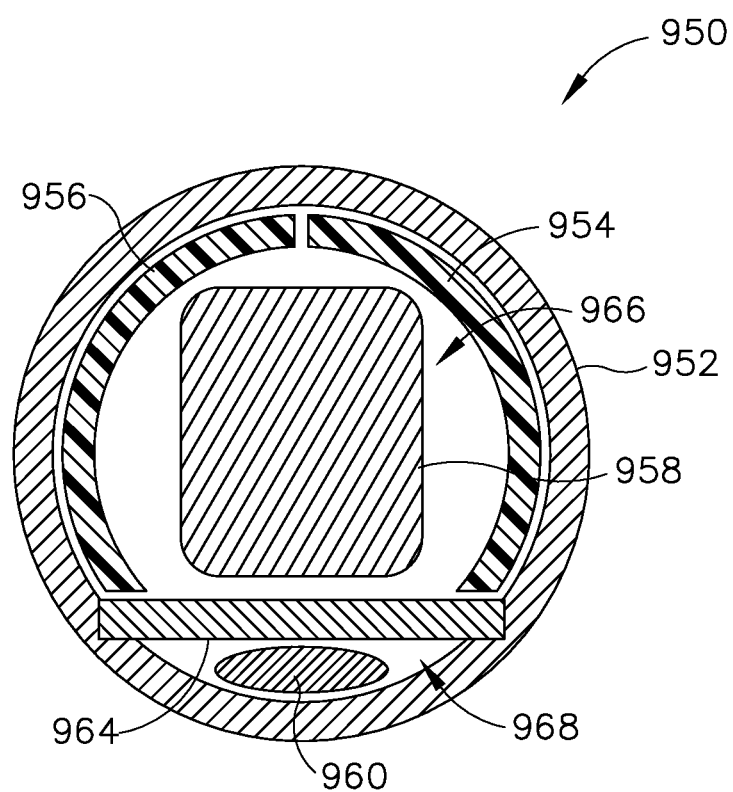
FIG. 26 depicts a front cross-sectional end view of yet another exemplary alternative shaft assembly and end effector, configured for incorporation in the instrument of FIG. 1.

H. Exemplary Alternative Shaft Assembly Profile with Partitioning Member Defining Channel for Single Lower Ribbon FIG. 26 shows yet another exemplary alternative profile of yet another exemplary alternative shaft assembly (950) that may be used as a substitute for shaft assembly (30) in instrument (10). Shaft assembly (950) of this example comprises an outer sheath (952), a pair of articulation bands (954, 956), a waveguide (958), and a ribbon (960). Articulation bands (954, 956) are configured to operate substantially similar to articulation bands (140, 142) discussed above, such that opposing longitudinal motion of articulation bands (954, 956) causes articulation of shaft assembly (950). Ribbon (960) is configured to operate substantially similar to cable (174), such that longitudinal translation of ribbon (960) actuates a clamp arm (not shown).

Outer sheath (952) has a circular cross-sectional profile. A partitioning member (964) extends between an interior surface of outer sheath (952) along a chord line, and divides the interior of outer sheath (952) into a first lumen (966) and a second lumen (968). Articulation bands (954, 956) each have a semi-circular profile. Articulation bands (954, 956) are slidably disposed within first lumen (966) of outer sheath (952) adjacent to one another and are configured to longitudinally translate to thereby cause articulation of shaft assembly (950). Ribbon (960) is slidably disposed within second lumen (968) of outer sheath (952) and is configured to longitudinally translate within second lumen (968) to thereby actuate the clamp arm.

In the cross-sectional region shown in FIG. 26, waveguide (958) has a rectangular profile and passes within the space defined between articulation bands (954, 956) and partitioning member (964). It should be understood that waveguide (908) may have any other suitable cross-sectional profile that fits within the space defined between articulation bands (954, 956) and partitioning member (964). Moreover, the cross-sectional profile of waveguide (958) may vary along the length of waveguide (958).

Figure 27:
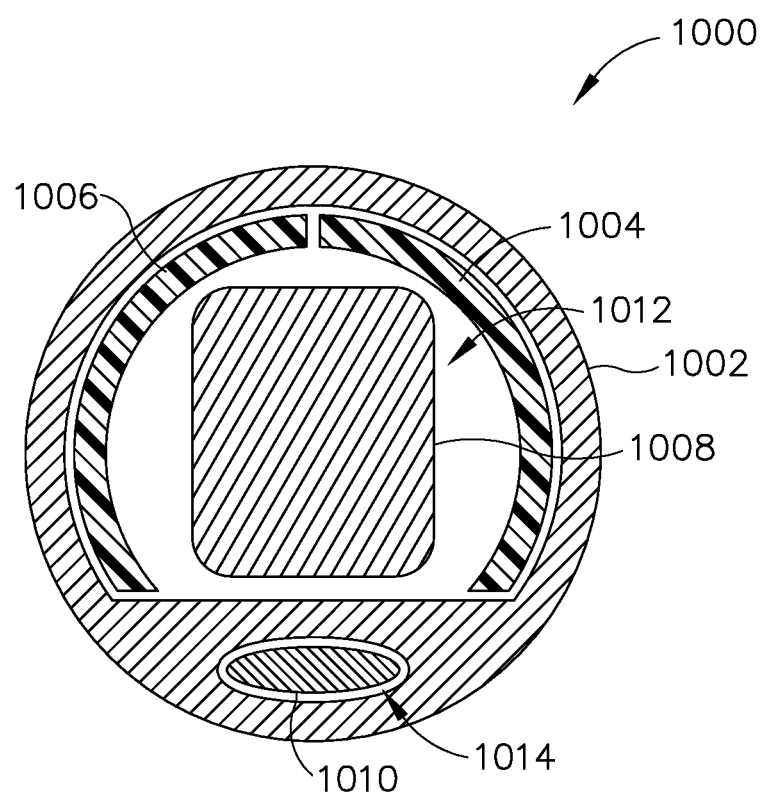
FIG. 27 depicts a front cross-sectional end view of yet another exemplary alternative shaft assembly and end effector, configured for incorporation in the instrument of FIG. 1.

I. Exemplary Alternative Shaft Assembly Profile with Outer Sheath Defining Channel for Single Lower Rod FIG. 27 shows yet another exemplary alternative profile of yet another exemplary alternative shaft assembly (1000) that may be used as a substitute for shaft assembly (30) in instrument (10). Shaft assembly (1000) of this example comprises an outer sheath (1002), a pair of articulation bands (1004, 1006), a waveguide (1008), and a ribbon (1010). Articulation bands (1004, 1006) are configured to operate substantially similar to articulation bands (140, 142) discussed above, such that opposing longitudinal motion of articulation bands (1004, 1006) causes articulation of shaft assembly (1000). Ribbon (1010) is configured to operate substantially similar to cable (174) discussed above, such that longitudinal translation of ribbon (1010) actuates a clamp arm (not shown).

Outer sheath (1002) defines a first lumen (1012) and a second lumen (1014). In some versions, outer sheath (1002) is formed in an extrusion process (e.g., from plastic and/or metal, etc.). Of course, any suitable process may be used to form outer sheath (852). Articulation bands (1004, 1006) each have a semi-circular profile. Articulation bands (1004, 1006) are slidably disposed within first lumen (1012) of outer sheath (1002) adjacent to one another and are configured to longitudinally translate to thereby cause articulation of shaft assembly (1000). Ribbon (1010) is slidably disposed within second lumen (1014) of outer sheath (1002) and is configured to longitudinally translate within second lumen (1018) to thereby actuate the clamp arm.

In the cross-sectional region shown in FIG. 27, waveguide (1008) has a rectangular profile and passes within the space defined between articulation bands (1004, 1006). It should be understood that waveguide (1008) may have any other suitable cross-sectional profile that fits within the space defined between articulation bands (1004, 1006). Moreover, the cross-sectional profile of waveguide (1008) may vary along the length of waveguide (1008).

III. EXEMPLARY ALTERNATIVE ACTUATION OF CLAMP ARM

It may be desirable to alter the operation of clamp arm (44) and/or articulation section (130). As will be discussed in more detail below, FIGS. 28-33B show various examples of how the operation of clamp arm (44) may be altered. While various examples of how the operation of clamp arm (44) may be altered will be described in greater detail below, other examples will be apparent to those of ordinary skill in the art according to the teachings herein. It should be understood that the examples of clamp arms described below may function substantially similar to clamp arm (44) discussed above. In particular, the examples of clamp arms described below are operable to compress tissue against an ultrasonic blade to thereby simultaneously sever the tissue and denature the proteins in adjacent tissue cells, thereby providing a coagulative effect.

A. Exemplary Alternative Clamp Arm Drive Assembly with Rod and Arcuate Arms

Figure 29:
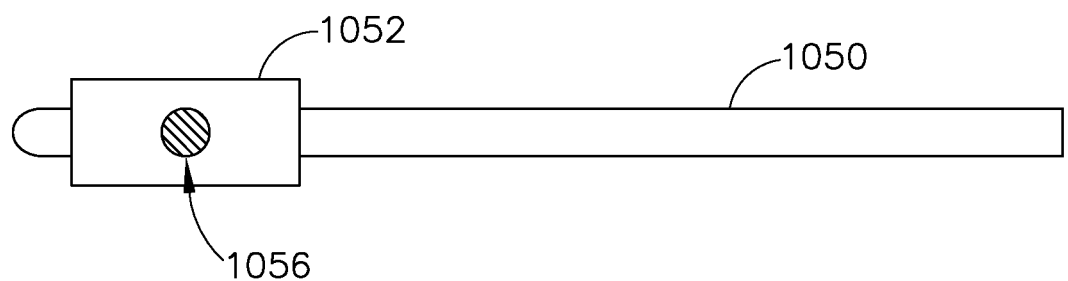
FIG. 29 depicts a side elevational view of the push/pull cable assembly of FIG. 28.
Figure 28:
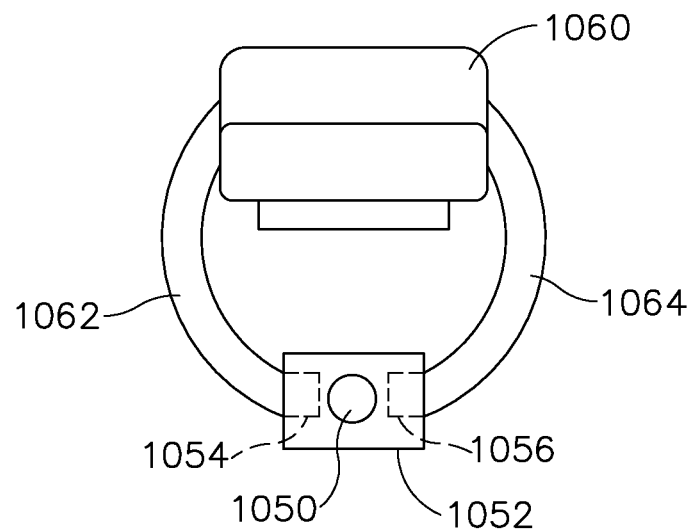
FIG. 28 depicts a front end view of a clamp arm coupled with an exemplary push/pull cable assembly configured for incorporation in any of the shaft assemblies and end effectors described herein.

FIGS. 28 and 29 show an exemplary rod (1050) and clamp arm (1060) that may be readily incorporated into instrument (10). Clamp arm (1060) is configured to operate substantially similar to clamp arm (44) discussed above, such that clamp arm (1060) is operable to selectively pivot toward and away from a blade (not shown) to selectively clamp tissue between clamp arm (1060) and the blade. Rod (1050) is configured to operate substantially similar to cable (174), such that longitudinal translation of rod (1050) causes actuation of clamp arm (1060) toward and away from the blade.

In the present example, a coupler (1052) is disposed at a distal end of rod (1050). Coupler (1052) comprises a pair of circular recesses (1054, 1056) formed in opposite sides of coupler (1052). A pair of arcuate arms (1062, 1064) extend transversely from clamp arm (1060). A circular projection (1066, 1068) extends inwardly from an interior surface of each arcuate arm (1062, 1064). Circular projections (1066, 1068) are rotatably disposed with respective circular recesses (1054, 1056) of coupler (1052). As discussed above with reference to instrument (10), clamp arm (1060) would be rotatably secured to a distal end of a longitudinally grounded shaft assembly (not shown), such that longitudinal movement of rod (1050) and coupler (1052) would pivotally actuate clamp arm (1060) toward and away from the blade.

B. Exemplary Alternative Clamp Arm Drive Assembly with Bent Rods

Figure 30:
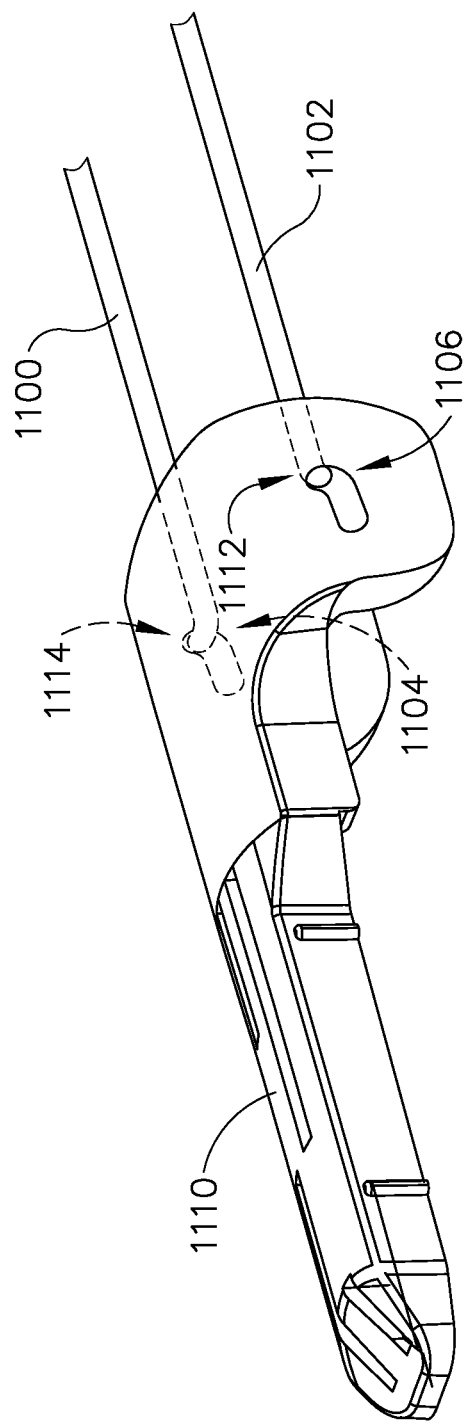
FIG. 30 depicts a perspective view of an exemplary alternative push/pull cable assembly configured for incorporation in any of the shaft assemblies and end effectors described herein.
Figure 31:
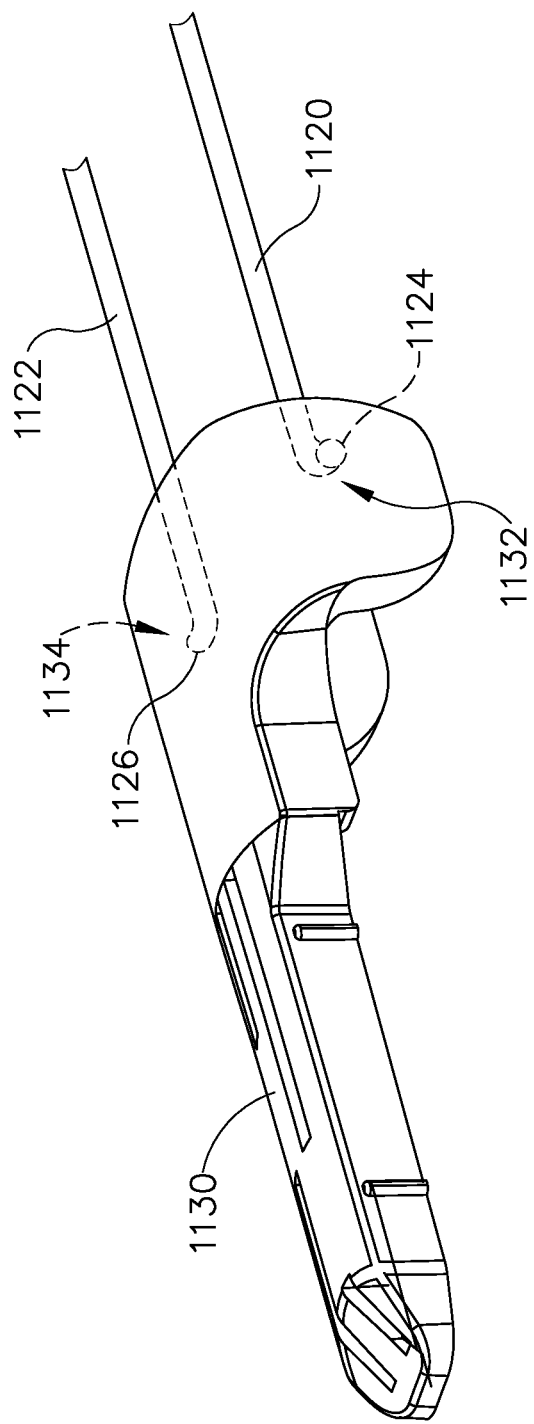
FIG. 31 depicts a perspective view of another exemplary alternative push/pull cable configured for incorporation in any of the shaft assemblies and end effectors described herein.

FIGS. 30 and 31 show additional examples of configurations that may be used to couple a pair of rods with a clamp arm to actuate the clamp arm. In the example shown in FIG. 30, a pair of rods (1100, 1102) each comprise a dog-leg feature (1104, 1106) at a distal end of rods (1100, 1102). A clamp arm (1110) comprises a pair of openings (1112, 1114). Dog-leg features (1104, 1106) of rods (1100, 1102) are pivotably disposed in openings (1112, 1114) of clamp arm (1110). As discussed above with reference to instrument (10), clamp arm (1110) would be rotatably secured to a distal end of a longitudinally grounded shaft assembly (not shown), such that longitudinal movement of rods (1100, 1102) would pivotally actuate clamp arm (1110) toward and away from a blade (not shown). In the present example, rods (1100, 1102) are directly coupled with clamp arm (1110). In some other versions, rods (1100, 1102) are coupled with clamp arm (1110) via some intermediary component. For instance, rods (1100, 1102) may instead be directly coupled with a collar or inner tube section, which may in turn be pivotally coupled with clamp arm (1110). Other suitable relationships will be apparent to those of ordinary skill in the art in view of the teachings herein.

In the example shown in FIG. 31, a pair of rods (1120, 1122) each comprise an outwardly projecting tab (1124, 1126) at a distal end of rods (1120, 1122). A clamp arm (1130) comprises a pair of openings (1132, 1134). Outwardly projecting tabs (1124, 1126) of rods (1120, 1122) are pivotably disposed in openings (1132, 1134) of clamp arm (1130). As discussed above with reference to instrument (10), clamp arm (1130) would be rotatably secured to a distal end of a longitudinally grounded shaft assembly (not shown), such that longitudinal movement of rods (1120, 1122) would pivotally actuate clamp arm (1130) toward and away from a blade (not shown). In the present example, rods (1120, 1122) are directly coupled with clamp arm (1130). In some other versions, rods (1120, 1122) are coupled with clamp arm (1130) via some intermediary component. For instance, rods (1120, 1122) may instead be directly coupled with a collar or inner tube section, which may in turn be pivotally coupled with clamp arm (1130). Other suitable relationships will be apparent to those of ordinary skill in the art in view of the teachings herein.

C. Exemplary Alternative Clamp Arm with Oblique Coupling Projection

Figure 32:
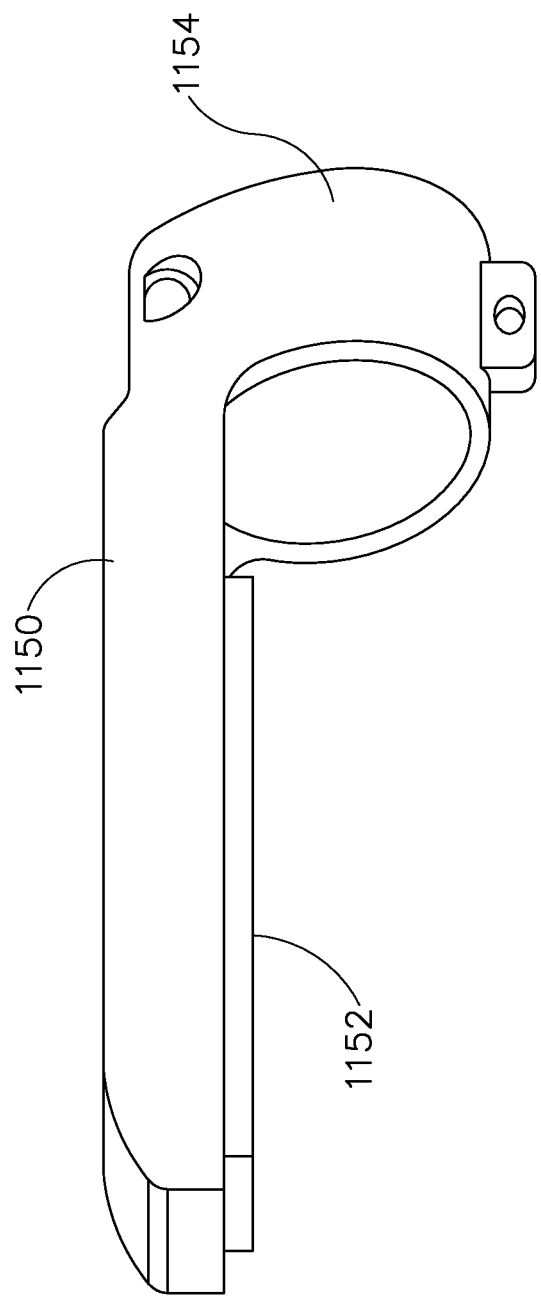
FIG. 32 depicts a perspective view of an exemplary clamp configured for incorporation in any of the end effectors described herein.
Figure 33A:
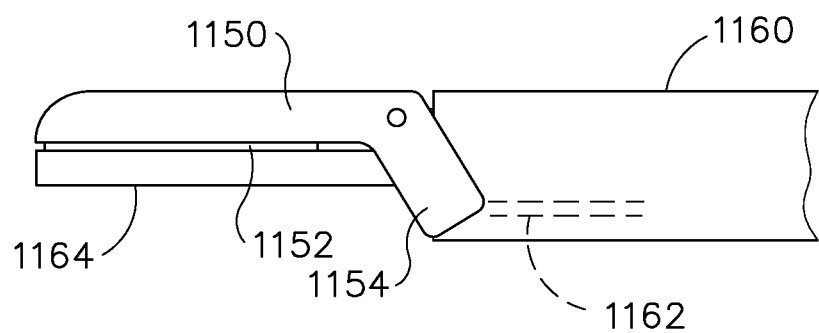
FIG. 33A depicts a side elevational view of an end effector having the clamp arm of FIG. 32, with the clamp arm in a closed position.
Figure 33B:
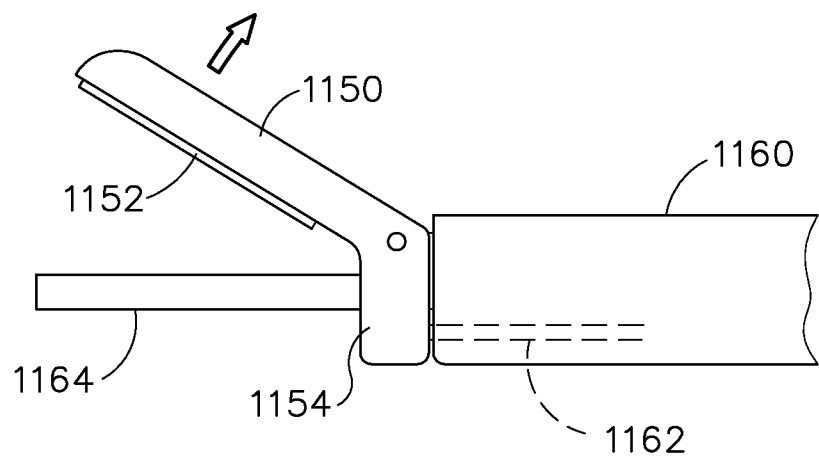
FIG. 33B depicts a side elevational view of the end effector of FIG. 33A, with the clamp arm moved to an open position.

FIGS. 32-33B show yet another exemplary alternative clamp arm (1150) that may be readily incorporated into instrument (10). Clamp arm (1150) of this example includes a clamp pad (1152) that is secured to the underside of clamp arm (1150). As shown in FIGS. 33A-33B, clamp arm (1150) is pivotably secured to a distal end of an exemplary alternative shaft assembly (1160). A tubular projection (1154) extends obliquely from clamp arm (1150) and is pivotably secured to a rod (1162). Rod (1162) is operable to translate longitudinally to thereby selectively pivot clamp arm (1150) toward and away from a blade (1164). As shown in FIG. 33A, tubular projection (1154) extends from clamp arm (1150) at an oblique angle relative to the longitudinal axis of shaft assembly (1160) when clamp arm (1150) is in a closed position. As shown in FIG. 33B, tubular projection (1154) extends from clamp arm (1150) perpendicularly to the longitudinal axis of shaft assembly (1160) when clamp arm (1150) is in an open position. It should be appreciated that, with tubular projection (1154) extending from clamp arm (1150) at an oblique angle relative to shaft assembly (1160), tubular projection (1154) will not contact blade (1164) when clamp arm (1150) is opened to a substantially wide open position.

D. Exemplary Alternative Articulation Section Drivers with Racks and Idler

FIGS. 34A-37 show yet another exemplary alternative shaft assembly (1200) and end effector (1210) that may be readily incorporated into instrument (10). Shaft assembly (1200) comprises a pair of articulation drive bands (1202, 1204) and a pair of jaw closure bands (1206, 1208). A distal end of each a articulation drive band (1202, 1204) is secured to a distal end of shaft assembly (1200) via a distal flange (1203) of a flexible waveguide (1230). When articulation drive bands (1202, 1204) are translated longitudinally in an opposing fashion, a moment is created and applied to the distal end of shaft assembly (1200) via distal flange (1203). Thus, opposing longitudinal motion of articulation drive bands (1202, 1204) causes articulation of shaft assembly (1200). Articulation drive bands (1202, 1204) may be driven using a version of articulation control assembly (100) described above or any other suitable mechanism.

Jaw closure bands (1206, 1208) pass slidably through flange (1203). A distal end of each jaw closure band (1206, 1208) is pivotably secured to a clamp arm (1212). It should be understood that FIGS. 34A-34B only show transverse coupling arms (1213) of clamp arm (1212). As discussed above with reference to instrument (10), clamp arm (1212) would be rotatably secured to a distal end of a longitudinally grounded shaft assembly (1200), such that simultaneous longitudinal translation of jaw closure bands (1206, 1208) pivotally actuates clamp arm (1212) toward and away from an ultrasonic blade (1214).

Figure 36:
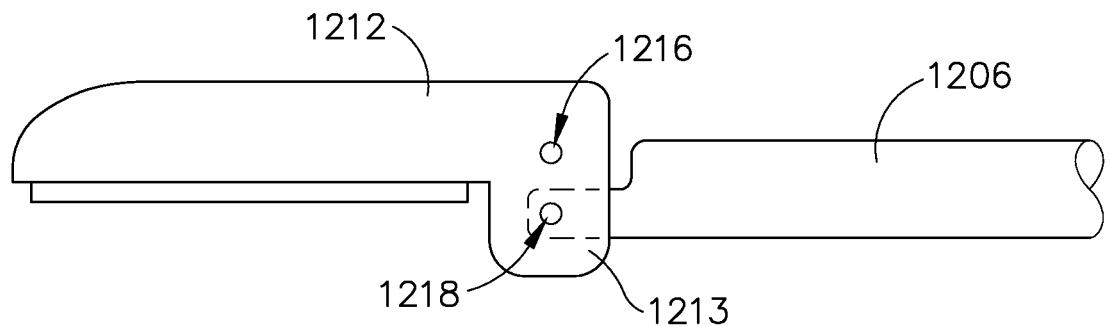
FIG. 36 depicts a side elevational view of an exemplary relationship between articulation bands and the clamp arm of the shaft assembly and end effector of FIG. 34A.
Figure 37:
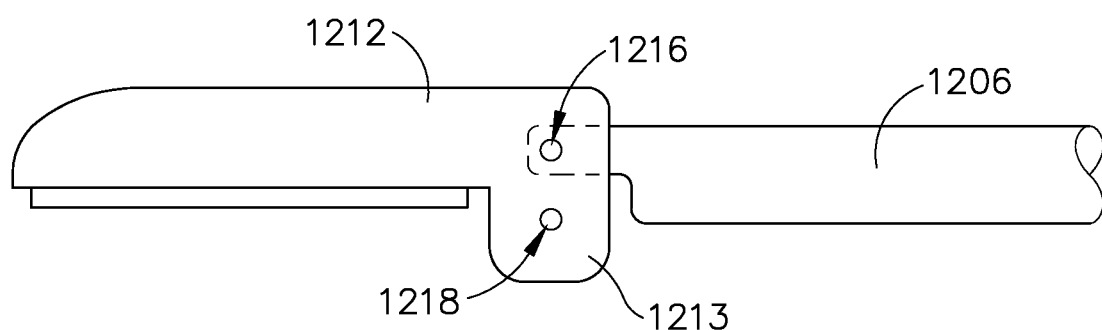
FIG. 37 depicts a side elevational view of another exemplary relationship between articulation bands and the clamp arm of the shaft assembly and end effector of FIG. 34A.

As shown in FIG. 36, jaw closure bands (1206, 1208) may be pivotably secured to a bottom pivot opening (1218) in each arm (1213) of clamp arm (1212) in those versions of end effector (1210) where a top portion of clamp arm (1212) is pivotably secured to shaft assembly (1200) via a top pivot opening (1216) in each arm (1213), such that simultaneous longitudinal translation of jaw closure bands (1206, 1208) causes pivoting of clamp arm (1212) toward and away from an ultrasonic blade (1214). As shown in FIG. 37, jaw closure bands (1206, 1208) may be pivotably secured to top pivot opening (1216) in each arm (1213) of clamp arm (1212) in those versions of end effector (1210) where a bottom portion of clamp arm (1212) is pivotably secured to shaft assembly (1200) via bottom pivot opening (1218) in each arm (1213), such that simultaneous longitudinal translation of jaw closure bands (1206, 1208) causes pivoting of clamp arm (1212) toward and away from an ultrasonic blade (1214).

Figure 34A:
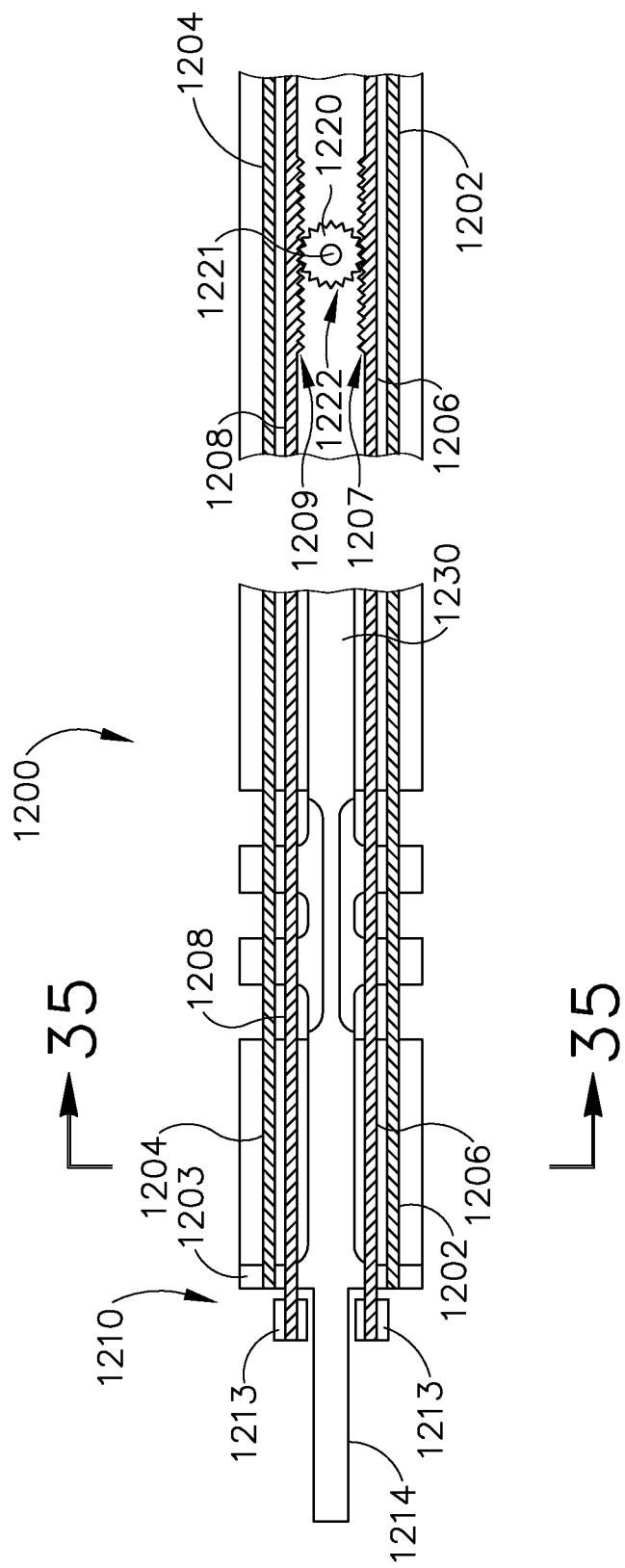
FIG. 34A depicts a cross-sectional top view of a distal portion of yet another exemplary alternative shaft assembly and end effector configured for incorporation in the instrument of FIG. 1, with the shaft assembly and end effector in a substantially straight configuration.
Figure 34B:
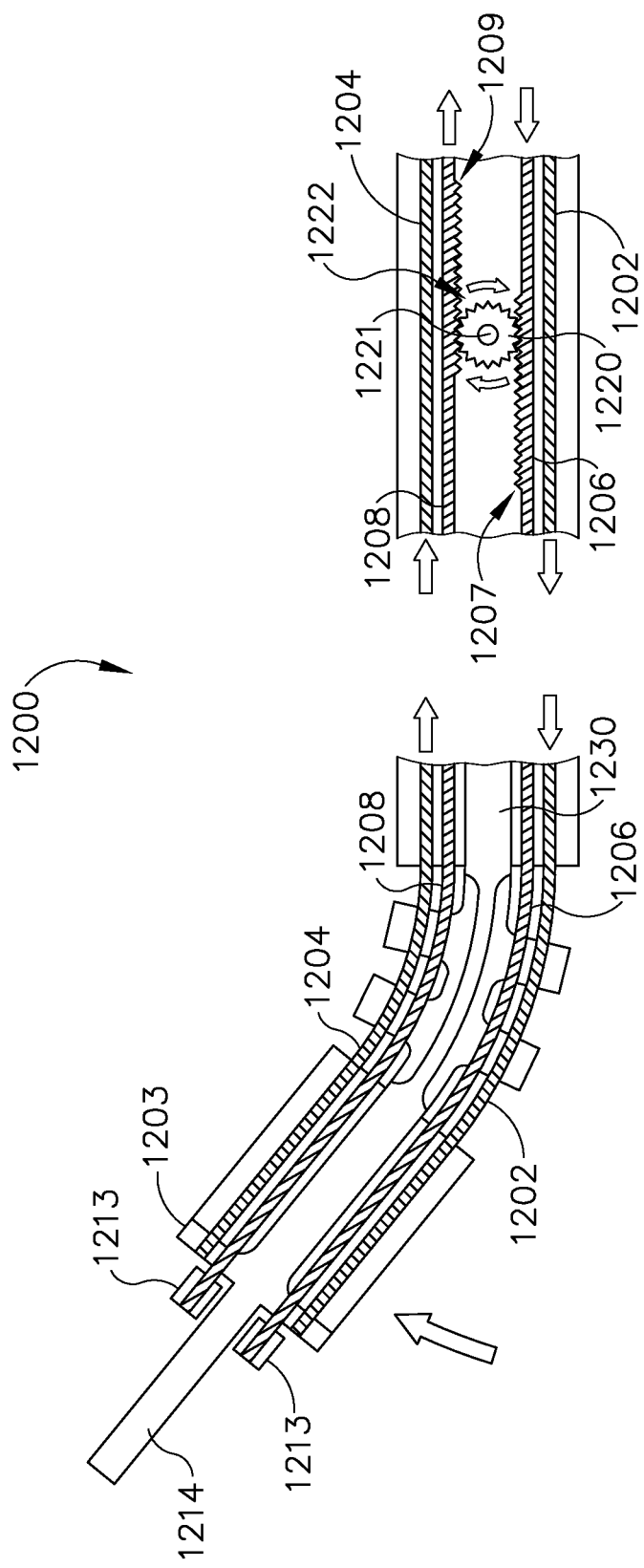
FIG. 34B depicts a cross-sectional top view of the shaft assembly and end effector of FIG. 34A moved into an articulated configuration.

Referring back to FIGS. 34A-34B, the proximal region of each jaw closure band (1206, 1208) includes a respective, inwardly directed rack (1207, 1209). Shaft assembly (1200) of the present example further comprises a gear (1220) positioned between racks (1207, 1209) of articulation jaw closure bands (1206, 1208). Gear (1220) comprises a plurality of teeth (1222) that mesh with complementary teeth of racks (1207, 1209). Gear (1220) is configured to rotate freely about a central axle (1221), such that gear (1220) serves as an idler. Thus, as shaft assembly (1200) is articulated by opposing longitudinal translation of articulation bands (1202, 1204), gear (1220) engages second pair of articulation bands (1206, 1208) and provides for guided, opposing longitudinal translation of jaw closure bands (1206, 1208) as shown in FIG. 34B. In other words, gear (1220) allows jaw closure bands (1206, 1208) to move in relation to each other to accommodate articulation of shaft assembly (1200).

Also in the present example, gear (1220) is operable to drive jaw closure bands (1206, 1208) longitudinally in the same direction in order to actuate clamp arm (1212). In particular, axle (1221) is configured to slide longitudinally relative to shaft assembly (1200), thereby providing longitudinal movement of gear (1220) relative to shaft assembly (1200). Due to engagement of teeth (1222) with racks, (1207, 1209), this will provide corresponding and simultaneous longitudinal movement of both jaw closure bands (1206, 1208) relative to shaft assembly (1200). Various suitable features that may be used to drive axle (1221) longitudinally will be apparent to those of ordinary skill in the art in view of the teachings herein.

Figure 35:
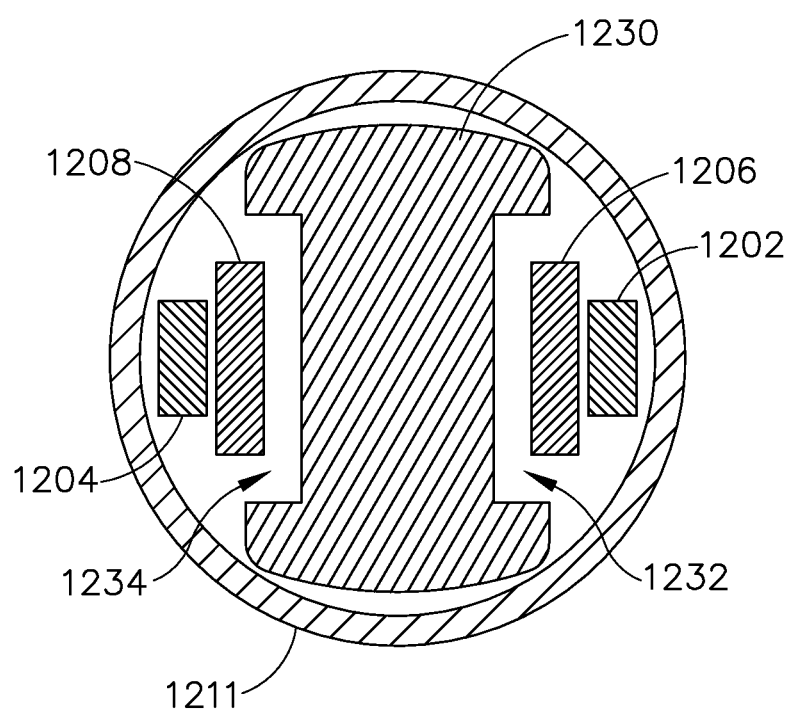
FIG. 35 depicts a cross-sectional view of the shaft assembly of FIG. 34A, taken along line 35-35 of FIG. 34A.

FIG. 35 shows a cross-sectional view of shaft assembly (1200). At this cross-sectional region, waveguide (1230) has an I-shaped cross-sectional profile with a pair of rectangular channels (1232, 1234) defined on opposite sides of waveguide (1230). Articulation bands (1202, 1204) are slidably disposed within channel (1232) between waveguide (1230) and an interior surface of an outer sheath (1211). Articulation bands (1206, 1208) are slidably disposed within channel (1234) between waveguide (1230) and an interior surface of an outer sheath (1211). Of course, any other suitable configurations may be used.

E. Exemplary Shaft Assembly with Clamp Arm Actuation via Flexible Outer Sheath

Figure 38:
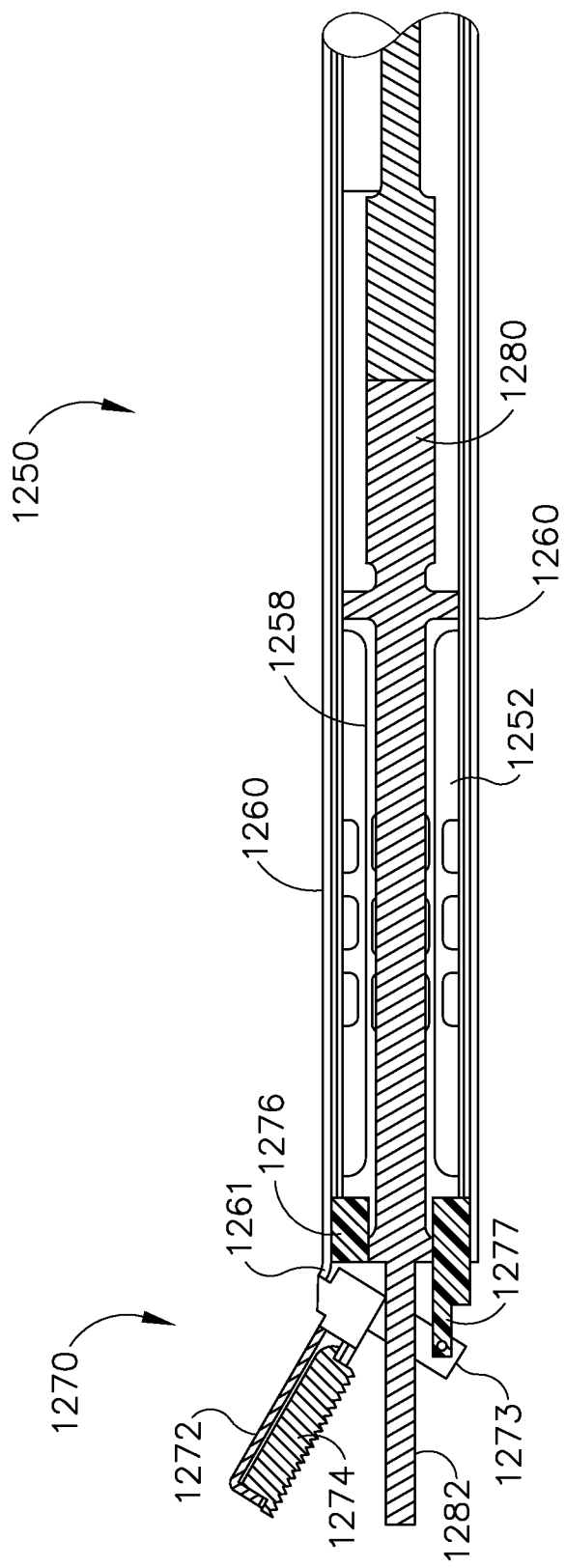
FIG. 38 depicts a cross-sectional side view of yet another exemplary alternative shaft assembly and end effector configured for incorporation in the instrument of FIG. 1.
Figure 39:
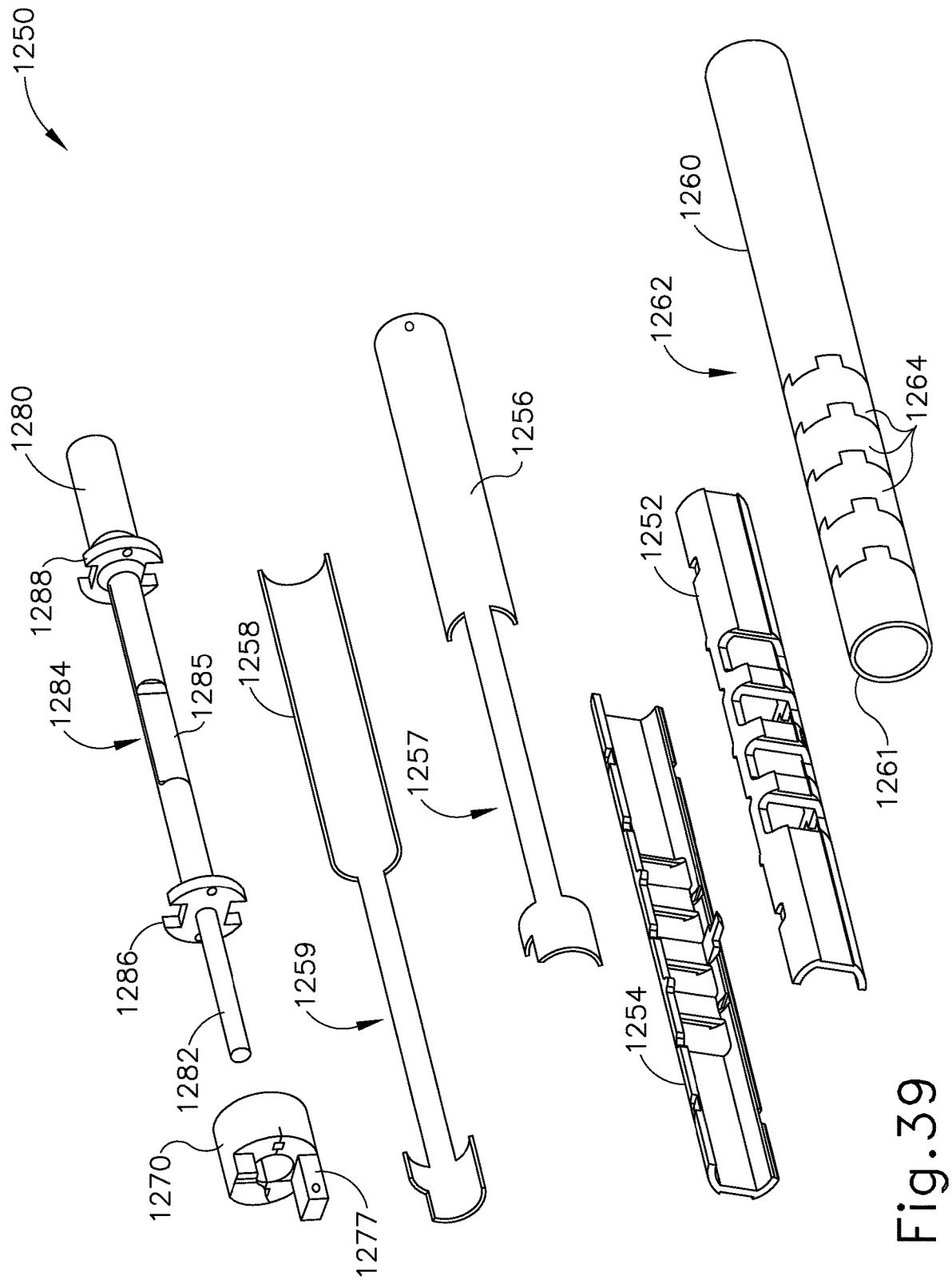
FIG. 39 depicts an exploded perspective view of the shaft assembly of FIG. 38.

FIGS. 38-39 show yet another exemplary alternative shaft assembly (1250) and end effector (1270) that may be readily incorporated into instrument (10). Shaft assembly (1250) comprises an outer sheath (1260), a pair of ribbed body portions (1252, 1254), a pair of articulation bands (1256, 1258), and a waveguide (1280). End effector (1270) includes an ultrasonic blade (1282) and a pivoting clamp arm (1272) having a clamp pad (1274). End effector (1270) is configured to operate substantially similar to end effector (40), such clamp arm (1272) of end effector (1270) is operable to compress tissue against blade (1282). When blade (1282) is activated while clamp arm (1272) compresses tissue against blade (1282), end effector (1270) simultaneously severs the tissue and denatures the proteins in adjacent tissue cells, thereby providing a coagulative effect.

Clamp arm (1272) is operable to selectively pivot toward and away from blade (1282) to selectively clamp tissue between clamp arm (1272) and blade (1282). A pair of arms (1273) extend transversely from clamp arm (1272). Arms (1273) are pivotably secured to a distally projecting tongue (1277) of a collar (1276). Collar (1276) is secured to a distal flange (1286) of waveguide (1280). Waveguide (1280) provides a longitudinal mechanical ground for collar (1276), which in turn provides a longitudinal mechanical ground to clamp arm (1272). Clamp arm (1272) is also pivotably secured with a distally projecting tongue (1261) of outer sheath (1260). Outer sheath (1260) is operable to translate longitudinally relative to waveguide (1280) and the other components of shaft assembly (1250) that are longitudinally mechanically grounded. It should therefore be understood that outer sheath (1260) is operable to actuate clamp arm (1272) toward and away from blade (1282). A trigger such as trigger (28) or any other suitable feature may be operable to translate outer sheath (1260) longitudinally, to thereby actuate clamp arm (1272) toward and away from blade (1282).

Blade (1282) is positioned at the distal end of an acoustic drivetrain. This acoustic drivetrain includes a transducer assembly (not shown) and waveguide (1280). Waveguide (1280) comprises a flexible portion (1284). Flexible portion (1284) of waveguide (1280) includes a distal flange (1286), a proximal flange (1288), and a narrowed section (1285) located between distal flanges (1286, 1288). In the present example, flanges (1286, 1288) are located at positions corresponding to nodes associated with resonant ultrasonic vibrations communicated through flexible portion (1284) of waveguide (1280). Narrowed section (1285) is configured to allow flexible portion (1284) of waveguide (1280) to flex without significantly affecting the ability of flexible portion (1284) of waveguide (1280) to transmit ultrasonic vibrations. As best seen in Outer sheath (1260) further comprises an articulation section (1262) having a series of interlocking rings (1264). Rings (1264) are configured to engage one another in a manner such that articulation section (1262) is operable to selectively flex at various lateral deflection angles relative to a longitudinal axis defined by shaft assembly (1250). Rings (1264) also allow outer sheath (1260) to translate along a bent region of shaft assembly (1250) when shaft assembly (1250) is in an articulated state.

Ribbed body portions (1252, 1254) are configured to selectively flex at various lateral deflection angles relative to the longitudinal axis defined by shaft assembly (1250) and to further provide for guidance of articulation bands (1256, 1258). In particular, ribbed body portions (1252, 1254) prevent articulation bands (1256) from contacting the region of waveguide (1280) between flanges (1286, 1288).

Articulation bands (1256, 1258) are configured to operate substantially similar to articulation bands (140, 142), such opposing longitudinal motion of articulation bands (1256, 1258) causes articulation of shaft assembly (1250). Articulation bands (1256, 1258) each comprise a flexible portion (1257, 1259) that is configured to align with the articulation section of shaft assembly (1250). Distal ends of articulation bands (1256, 1258) are secured to collar (1276). When articulation bands (1256, 1258) are translated longitudinally in an opposing fashion, a moment is created and applied to distal flange (1286) via collar (1276). This causes the articulation section of shaft assembly (1250), in particular articulation section (1262), ribbed body portions (1252, 1254), flexible portion (1257, 1259) of articulation bands (1256, 1258), and narrowed section (1285) of flexible portion (1284) of waveguide (1280), to articulate, without transferring axial forces in articulation bands (1256, 1258) to waveguide (1280).

Figure 40:
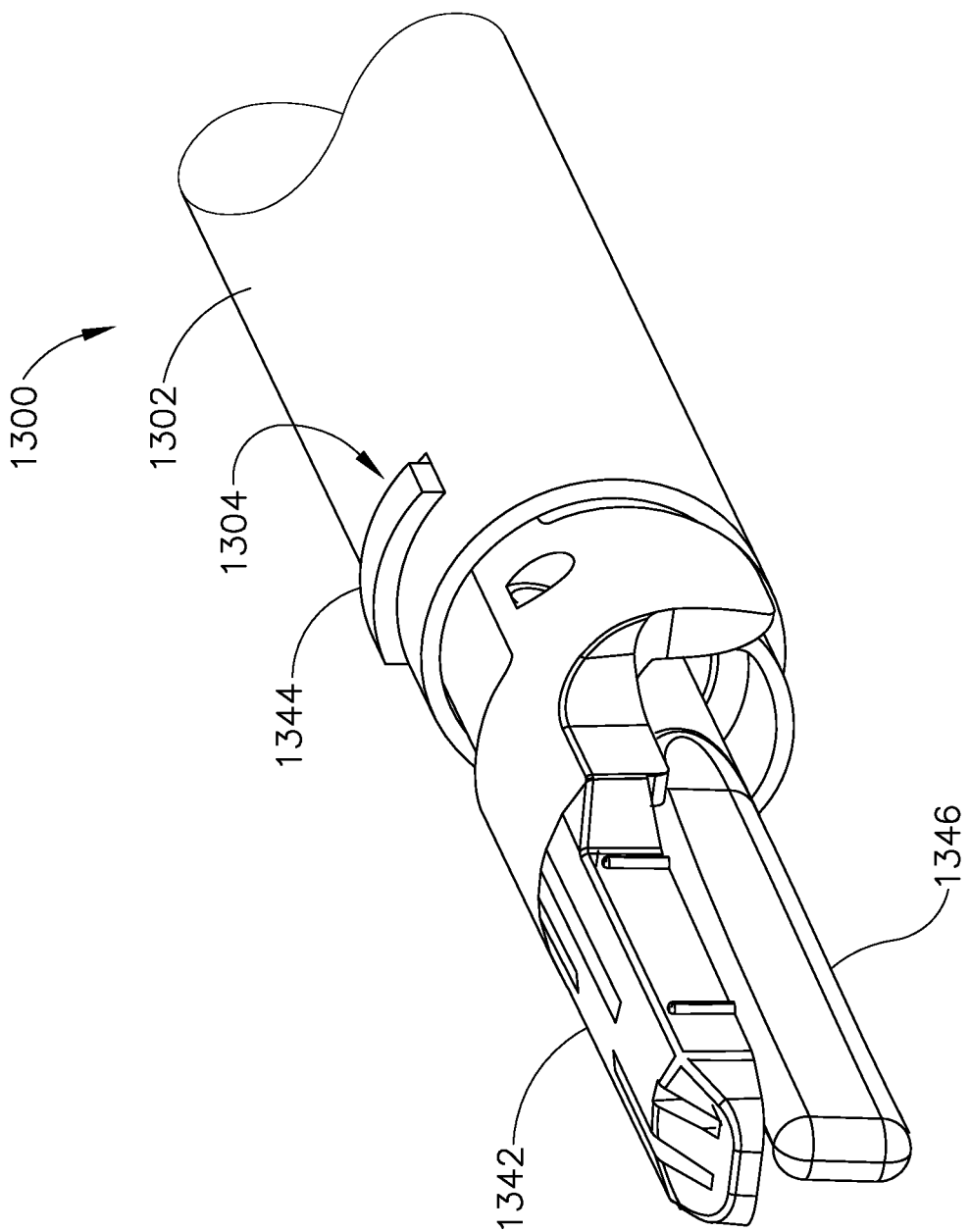
FIG. 40 depicts a detailed perspective view of yet another exemplary alternative shaft and end effector assembly configured for incorporation in the instrument of FIG. 1.

F. Exemplary Alternative Configuration for Outer Closure Tube for Actuation of Clamp Arm FIG. 40 shows yet another exemplary alternative shaft assembly (1300) and end effector (1340) that may be readily incorporated into instrument (10). Shaft assembly (1300) of this example comprises an outer sheath (1302) that is configured to translate longitudinally relative to end effector (1340) to pivotally actuate a clamp arm (1342) toward and away from an ultrasonic blade (1346). Shaft assembly (1300) and end effector (1340) thus operate similar to shaft assembly (1250) and end effector (1270) described above. However, in this example, a distal end of outer sheath (1302) defines a slot (1304). Clamp arm (1342) of end effector (1340) comprises a proximal projection (1344) extending upwardly from clamp arm (1342). Proximal projection (1344) is disposed within slot (1304). As discussed above with reference to instrument (10), clamp arm (1304) is pivotally secured to a longitudinally grounded component of shaft assembly (1300), such that longitudinal translation of outer sheath (1302) causes pivoting of clamp arm (1342) toward and away from blade (1346) via engagement of projection (1344) with slot (1304). Other suitable ways in which clamp arm (1342) may be coupled with a translating outer sheath (1302) will be apparent to those of ordinary skill in the art in view of the teachings herein.

G. Exemplary Alternative Actuation of Articulation Section

Figure 41:
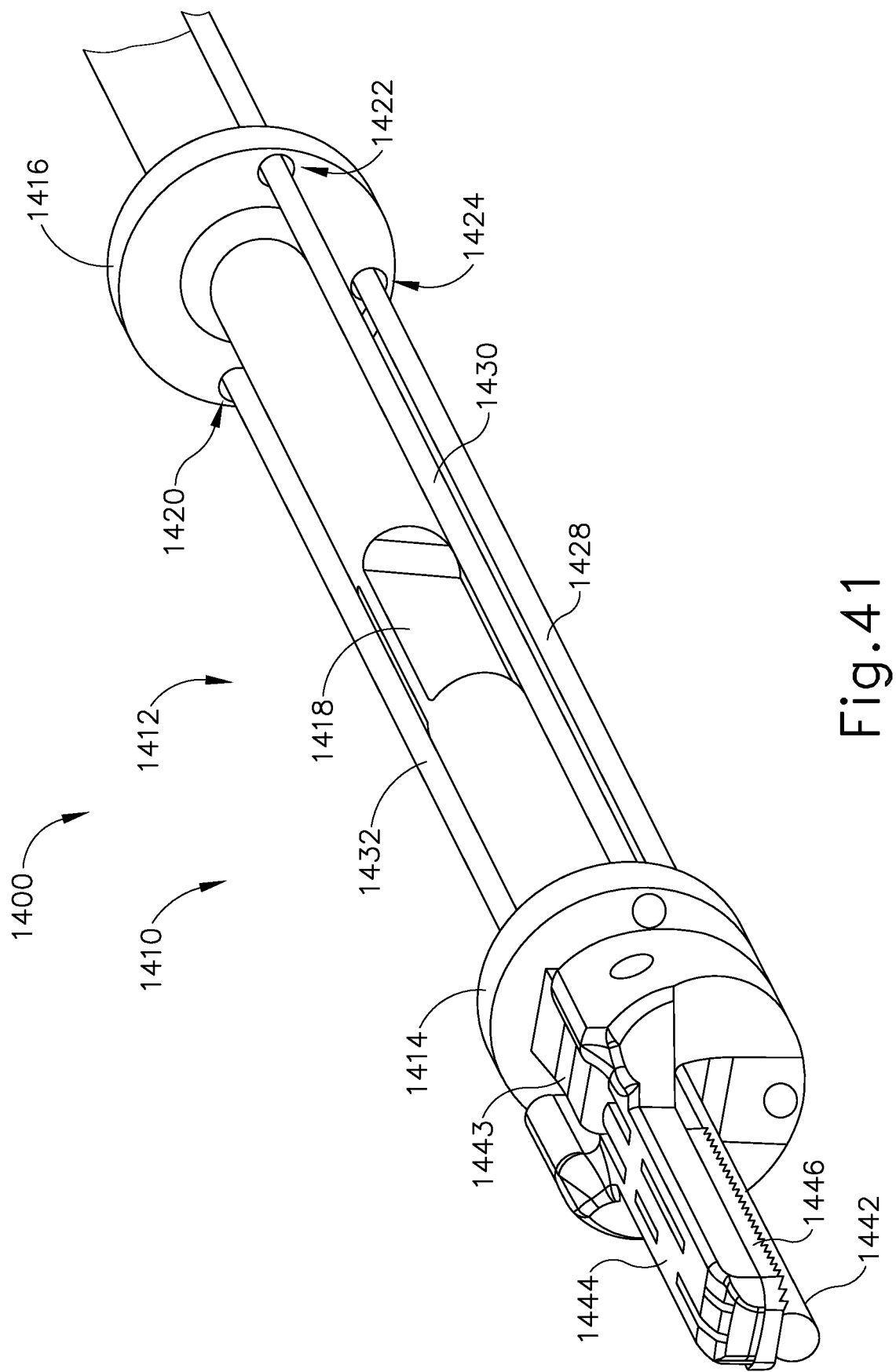
FIG. 41 depicts a perspective view of components of yet another exemplary alternative shaft assembly configured for incorporation in the instrument of FIG. 1.
Figure 42A:
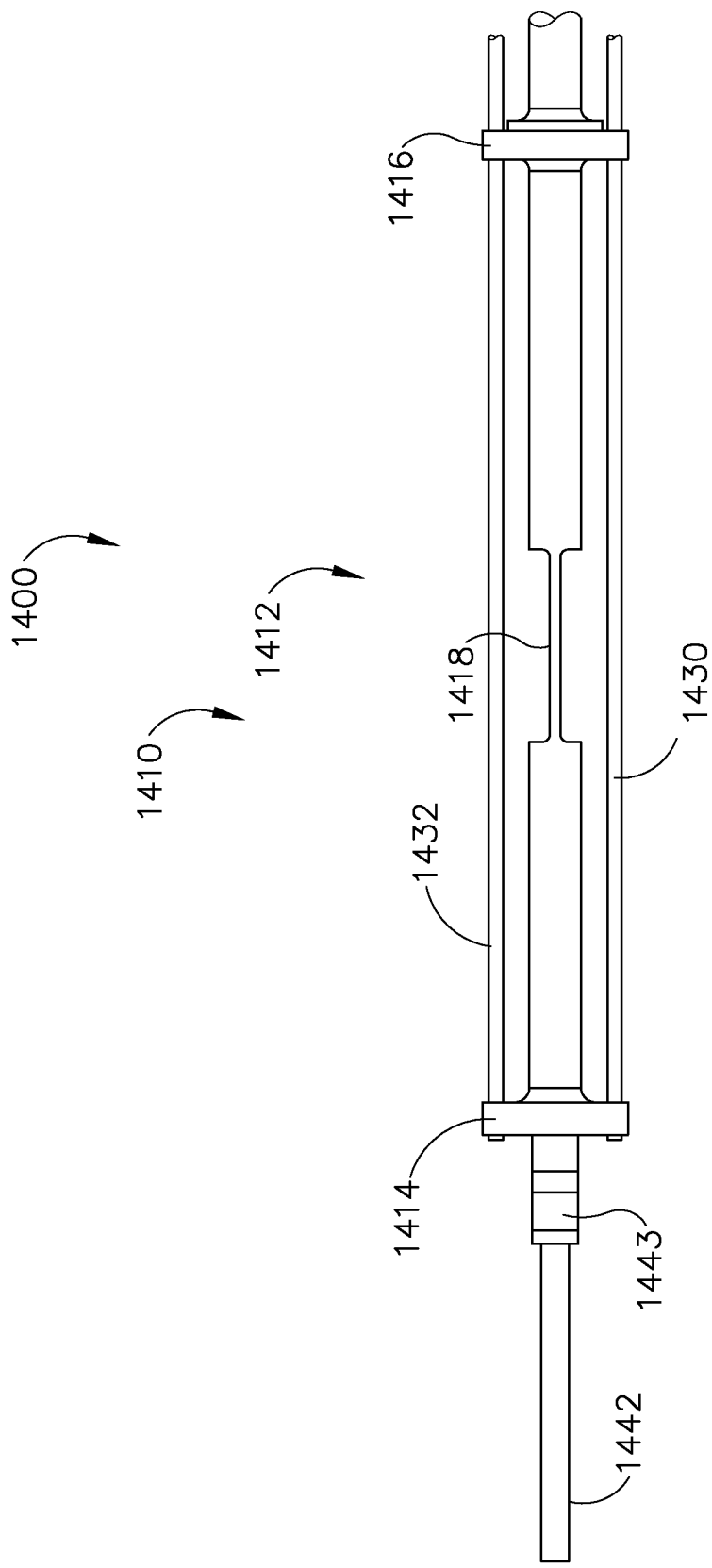
FIG. 42A depicts a top plan view of the shaft assembly of FIG. 41 in a straight configuration.
Figure 42B:
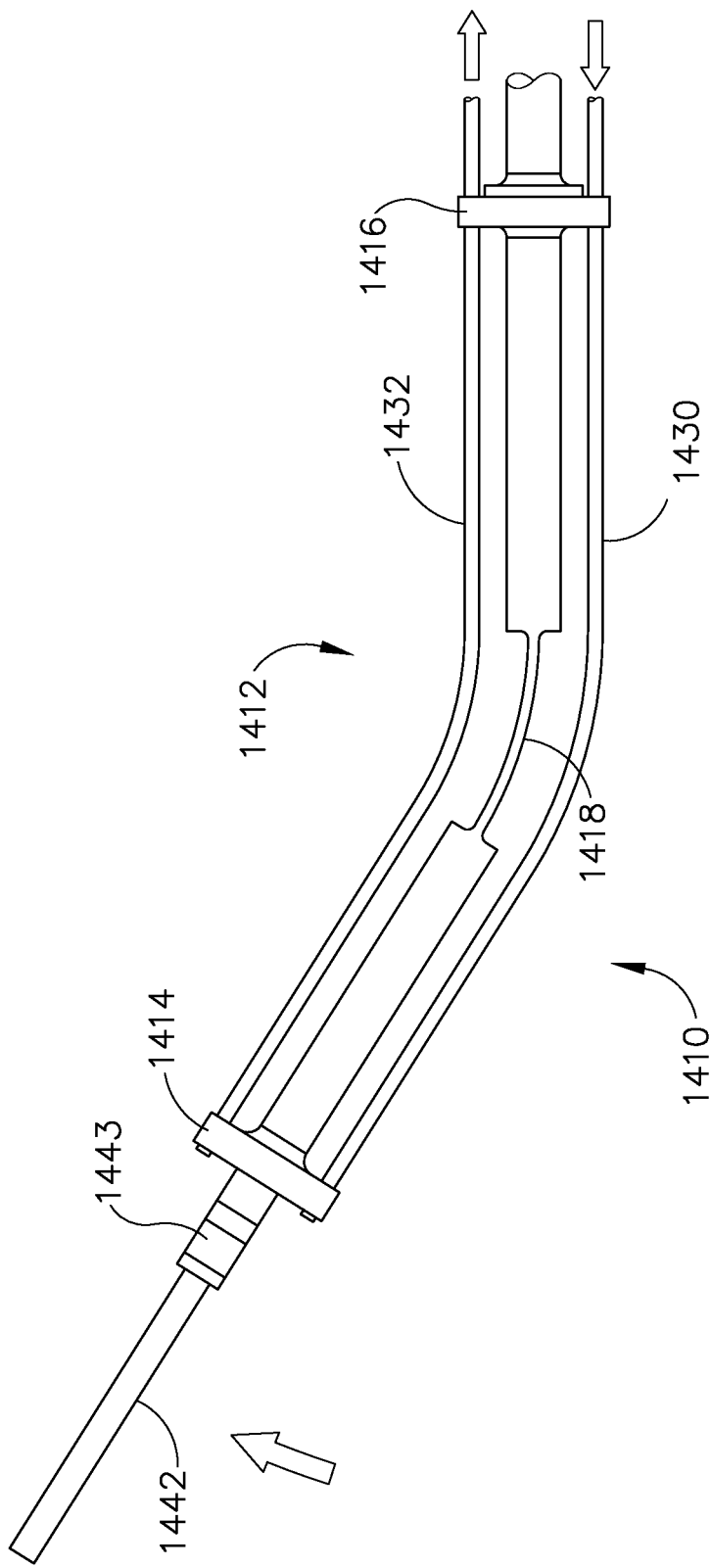
FIG. 42B depicts a top plan view of the shaft assembly of FIG. 41 in an articulated configuration.

FIGS. 41-42B show exemplary alternative internal components of yet another exemplary alternative shaft assembly (1400) and end effector (1440) that may be readily incorporated into instrument (10). End effector (1440) of this example comprises an ultrasonic blade (1442) and a clamp arm (1444). Clamp arm (1444) includes a clamp pad (1446) that is secured to the underside of clamp arm (1444), facing blade (1442). Blade (1442) of the present example is configured to operate substantially similar to blade (160) discussed above, such that blade (1442) is operable to vibrate at ultrasonic frequencies in order to effectively cut through and seal tissue, particularly when the tissue is being compressed between clamp pad (1446) and blade (1442). Blade (1442) is positioned at the distal end of an acoustic drivetrain. This acoustic drivetrain includes transducer assembly (12) and an acoustic waveguide (1410). The transducer assembly is operable to convert electrical power into ultrasonic vibrations, which are then transmitted along waveguide (1410), including flexible portion (1412) of waveguide (1410), to blade (1442) in accordance with known configurations and techniques. By way of example only, this portion of the acoustic drivetrain may be configured in accordance with various teachings of various references that are cited herein.

Waveguide (1410) comprises a flexible portion (1412), a distal flange (1414), and a proximal flange (1416). As best seen in FIGS. 42A and 42B, flexible portion (1412) of waveguide (1410) includes a narrowed section (1418) located between flanges (1414, 1416). In the present example, flanges (1414, 1416) are located at positions corresponding to nodes associated with resonant ultrasonic vibrations communicated through flexible portion (1412) of waveguide (1410). Narrowed section (1418) is configured to allow flexible portion (1412) of waveguide (1410) to flex without significantly affecting the ability of flexible portion (1412) of waveguide (1410) to transmit ultrasonic vibrations. By way of example only, narrowed section (1418) may be configured in accordance with one or more teachings of U.S. Pub. No. 2014/0005701, issued as U.S. Pat. No. 9,393,037 on Jul. 19, 2016 and/or U.S. Pub. No. 2014/0114334, issued as U.S. Pat. No. 9,095,367 on Aug. 4, 2015, the disclosures of which are incorporated by reference herein. It should be understood that waveguide (1410) may be configured to amplify mechanical vibrations transmitted through waveguide (1410). Furthermore, waveguide (1410) may include features operable to control the gain of the longitudinal vibrations along waveguide (1410) and/or features to tune waveguide (1410) to the resonant frequency of the system.

In the present example, the distal end of blade (1442) is located at a position corresponding to an anti-node associated with resonant ultrasonic vibrations communicated through flexible portion (1412) of waveguide (1410), in order to tune the acoustic assembly to a preferred resonant frequency $f_o$ when the acoustic assembly is not loaded by tissue. When transducer assembly (12) is energized, the distal end of blade (1442) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (12) of the present example is activated, these mechanical oscillations are transmitted through waveguide (1410) to reach blade (1442), thereby providing oscillation of blade (1442) at the resonant ultrasonic frequency. Thus, when tissue is compressed between blade (1442) and clamp pad (1446), the ultrasonic oscillation of blade (1442) may simultaneously sever the tissue and denature the proteins in adjacent tissue cells, thereby providing a coagulative effect with relatively little thermal spread. In some versions, an electrical current may also be provided through blade (1442) and clamp arm (1444) to also cauterize the tissue. Other suitable configurations for an acoustic transmission assembly and transducer assembly will be apparent to one or ordinary skill in the art in view of the teachings herein. Similarly, other suitable configurations for end effector (1440) will be apparent to those of ordinary skill in the art in view of the teachings herein.

The internal components of shaft assembly (1400) further comprise a pair of articulation cables (1430, 1432). Proximal flange (1416) of flexible portion (1412) of waveguide (1410) comprises a plurality of through bores (1420, 1422, 1424). The distal ends of articulation cables (1430, 1432) are unitarily secured to distal flange (1414) of flexible portion (1412) of waveguide (1410). Articulation cables (1430, 1432) extend proximally from distal flange (1414) and pass freely through through bores (1420, 1422) within shaft assembly (1400). As one articulation cable (1430, 1432) is pulled proximally, this will cause an articulation section of shaft assembly (1400) to bend, thereby laterally deflecting end effector (1440) away from a longitudinal axis of shaft assembly (1400) at an articulation angle as shown in FIG. 42B. In particular, end effector (1440) will be articulated toward the articulation cable (1430, 1432) that is being pulled proximally. During such articulation, the other articulation cable (1430, 1432) will be pulled distally by distal flange (1414) of flexible portion (1412) of waveguide (1410). Flexible portion (1412) is configured to effectively communicate ultrasonic vibrations from waveguide (1410) to blade (1442) even when the articulation section of shaft assembly (1440) is in an articulated state as shown in FIG. 42B.

Distal flange (1414) of flexible portion (1412) of waveguide (1410) is fixedly secured to a distal end of shaft assembly (1400). When articulation cables (1430, 1432) are translated longitudinally in an opposing fashion, a moment is created and applied to the distal end shaft assembly (1400) via distal flange (1414). This causes the articulation section of shaft assembly (1400) and narrowed section (1418) of flexible portion (1412) of waveguide (1410) to articulate, without transferring axial forces in articulation cables (1430, 1432) to waveguide (1410). It should be understood that one articulation cable (1430, 1432) may be actively driven distally while the other articulation cable (1430, 1432) is passively permitted to retract proximally. As another merely illustrative example, one articulation cable (1430, 1432) may be actively driven proximally while the other articulation cable (1430, 1432) is passively permitted to advance distally. As yet another merely illustrative example, one articulation cable (1430, 1432) may be actively driven distally while the other articulation cable (1430, 1432) is actively driven proximally. Various suitable ways in which articulation cables (1430, 1432) may be driven will be apparent to those of ordinary skill in the art in view of the teachings herein. It should also be understood that one or more spacers may be used to prevent articulation cables (1430, 1432) from contacting waveguide (1410) between flanges (1414, 1416).

An upper portion of clamp arm (44) is pivotally secured to a distally projecting tongue (1443) of distal flange (1414) of waveguide (1410). Clamp arm (1444) is operable to selectively pivot toward and away from blade (1442) to selectively clamp tissue between clamp pad (1446) and blade (1442). A cable (1428) is secured to a lower portion of clamp arm (1444). Cable (1428) extends proximally from clamp arm (1444) and passes freely through distal flange (1414) and freely through through bore (1424) of proximal flange (1416) within shaft assembly (1400). Cable (1428) is operable to translate longitudinally relative to the articulation section of shaft assembly (1400) to selectively pivot clamp arm (1444) toward and away from blade (1442). Cable (1428) may be coupled with a trigger such that clamp arm (1444) pivots toward and away from blade (1442) in response to pivoting of the trigger. Clamp arm (1444) may be biased toward the open position, such that (at least in some instances) the operator may effectively open clamp arm (1444) by releasing a grip on the trigger.

IV. EXEMPLARY ALTERNATIVE WAVEGUIDE CONFIGURATIONS

It may be desirable to provide for alternative engagement between waveguide (180) and shaft assembly (30). As will be discussed in more detail below, FIGS. 43-50 show various examples of how waveguide (180) may engage shaft assembly (30). While various examples of how waveguide (180) may engage shaft assembly (30) will be described in greater detail below, other examples will be apparent to those of ordinary skill in the art according to the teachings herein. It should be understood that the examples of waveguides described below may function substantially similar to clamp waveguide (180) discussed above. In particular, the examples of waveguides described below are operable to transmit ultrasonic vibrations from transducer (12) to an ultrasonic blade.

FIGS. 43-46 show an exemplary alternative waveguide (1500) that may be readily incorporated into instrument (10). Waveguide (1500) of this example comprises an ultrasonic blade (1502) and a flexible portion (1504). Blade (1502) of the present example is configured to operate substantially similar to blade (160) discussed above except for the differences discussed below. In particular, blade (1502) of the present example is operable to vibrate at ultrasonic frequencies in order to effectively cut through and seal tissue. As discussed above, transducer assembly (12) is operable to convert electrical power into ultrasonic vibrations, which are then transmitted along waveguide (1502), including flexible portion (1504) of waveguide (1502) to blade (1502) in accordance with known configurations and techniques. By way of example only, this portion of the acoustic drivetrain may be configured in accordance with various teachings of various references that are cited herein.

Figure 43:
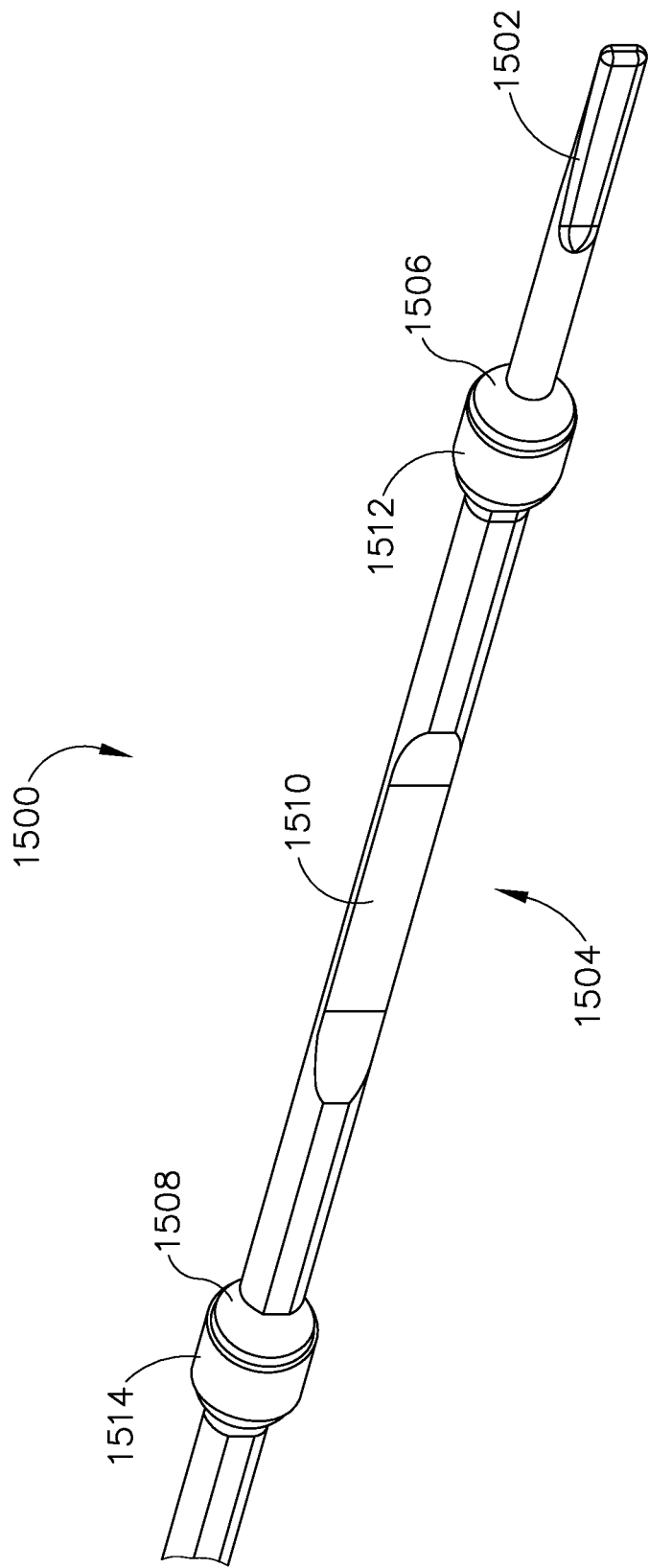
FIG. 43 depicts a perspective view of an exemplary alternative waveguide configured for incorporation in the instrument of FIG. 1.

As best seen in FIG. 43, flexible portion (1504) of waveguide (1500) includes a distal flange (1506), a proximal flange (1508), and a narrowed section (1510) located between flanges (1506, 1508). In the present example, flanges (1506, 1508) are located at positions corresponding to nodes associated with resonant ultrasonic vibrations communicated through flexible portion (1504) of waveguide (1500). Narrowed section (1510) is configured to allow flexible portion (1504) of waveguide (1500) to flex without significantly affecting the ability of flexible portion (1504) of waveguide (1500) to transmit ultrasonic vibrations. By way of example only, narrowed section (1510) may be configured in accordance with one or more teachings of U.S. Pub. No. 2014/0005701, issued as U.S. Pat. No. 9,393,037 on Jul. 19, 2016 and/or U.S. Pub. No. 2014/0114334, issued as U.S. Pat. No. 9,095,367 on Aug. 4, 2015, the disclosures of which are incorporated by reference herein. It should be understood that waveguide (1500) may be configured to amplify mechanical vibrations transmitted through waveguide (1500). Furthermore, waveguide (1500) may include features operable to control the gain of the longitudinal vibrations along waveguide (1500) and/or features to tune waveguide (1500) to the resonant frequency of the system.

In the present example, the distal end of blade (1502) is located at a position corresponding to an anti-node associated with resonant ultrasonic vibrations communicated through flexible portion (1504) of waveguide (1500), in order to tune the acoustic assembly to a preferred resonant frequency $f_o$ when the acoustic assembly is not loaded by tissue. When transducer assembly (12) is energized, the distal end of blade (1502) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (12) of the present example is activated, these mechanical oscillations are transmitted through waveguide (1500) to reach blade (1502), thereby providing oscillation of blade (1502) at the resonant ultrasonic frequency. Thus, the ultrasonic oscillation of blade (1502) may simultaneously sever the tissue and denature the proteins in adjacent tissue cells, thereby providing a coagulative effect with relatively little thermal spread. In some versions, an electrical current may also be provided through blade (1502) to also cauterize the tissue. While some configurations for an acoustic transmission assembly and transducer assembly (12) have been described, still other suitable configurations for an acoustic transmission assembly and transducer assembly (12) will be apparent to one or ordinary skill in the art in view of the teachings herein.

Figure 44:
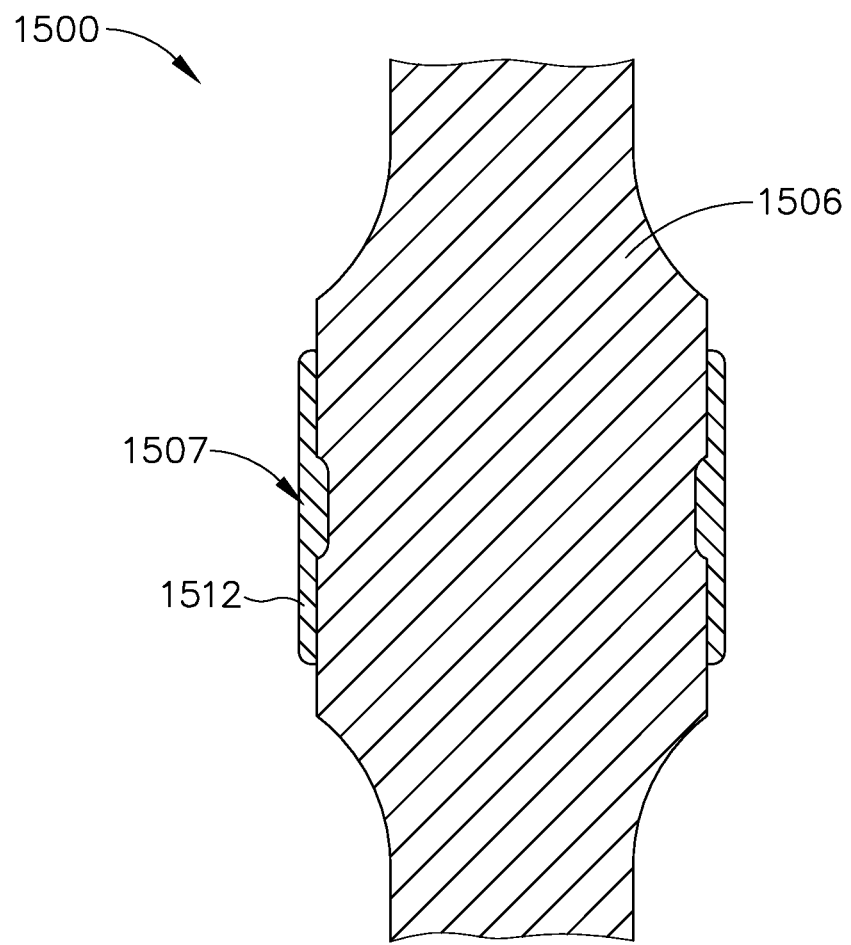
FIG. 44 depicts a cross-sectional top view of a flange of the waveguide of FIG. 43.

Waveguide (1500) further comprises a pair of overmolds (1512, 1514) secured about an exterior of flanges (1506, 1508). Overmolds (1512, 1514) of flanges (1506, 1508) are configured to engage an interior surface of shaft assembly (30). Overmolds (1512, 1514) provide an acoustic barrier between waveguide (1500) and shaft assembly (30) to thereby lessen the effect that engagement between waveguide (1500) and shaft assembly (30) may have upon transmission of ultrasonic vibrations within waveguide (1500). As shown in FIG. 44, flanges (1506, 1508) of the present example comprise an annular groove (1507) formed in an exterior surface of flanges (1506, 1508). Overmolds (1512, 1514) may be disposed within groove (1507) to thereby improve engagement between overmolds (1512, 1514) and flanges (1506, 1508). Overmolds (1512, 1514) may comprise polytetrafluoroethylene (PTFE), rubber, silicone, plastic, and/or any other suitable material(s).

As best seen in FIG. 46, flanges (1506, 1508) of the present example have a circular cross-sectional profile. It should be understood, however, that any other suitable shapes may be used. For instance, FIGS. 47-48 show an exemplary alternative waveguide (1550) with a flange (1556) having an oblong shape. In particular, flange (1556) includes a pair of flats (1557). A blade (1552) is located distal to flange (1556). An overmold (1562) is positioned about flange (1556) and has a cross-sectional profile complementing the cross-sectional profile of flange (1556). FIGS. 49-50 show another exemplary alternative waveguide (1600) with a flange (1606) having an oblong shape. In particular, flange (1606) includes a pair of flats (1607) and a pair of longitudinally extending grooves (1609). A blade (1602) is located distal to flange (1606). An overmold (1612) is positioned about flange (1606) and has a cross-sectional profile complementing the cross-sectional profile of flange (1606). Other suitable configurations that may be used for flanges will be apparent to those of ordinary skill in the art in view of the teachings herein.

V. EXEMPLARY ALTERNATIVE INSTRUMENT WITH DUAL ROLE BANDS AND DUAL ACTUATORS

Figure 51:
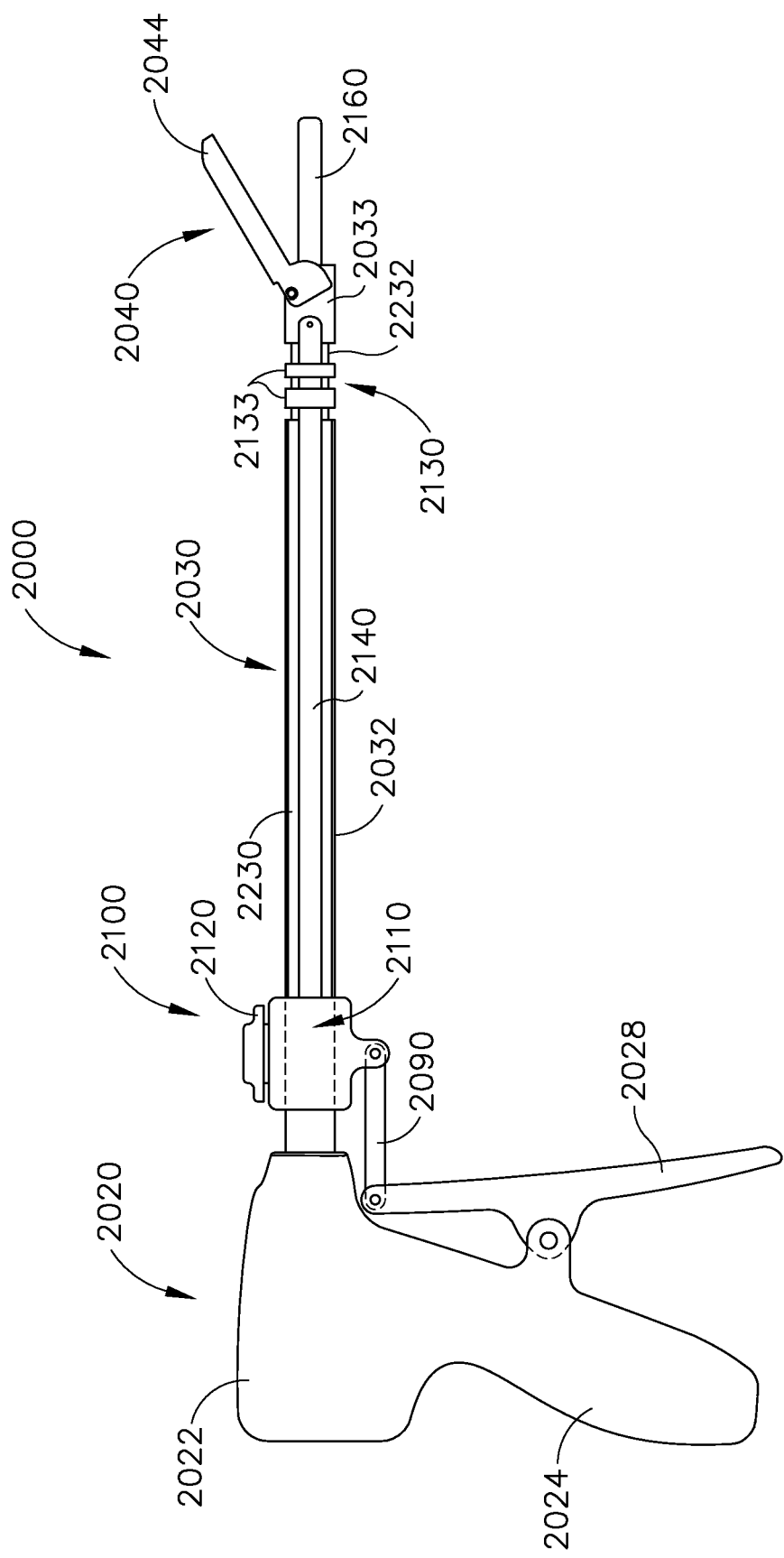
FIG. 51 depicts a side elevational view of an exemplary alternative ultrasonic surgical instrument.
Figure 52:
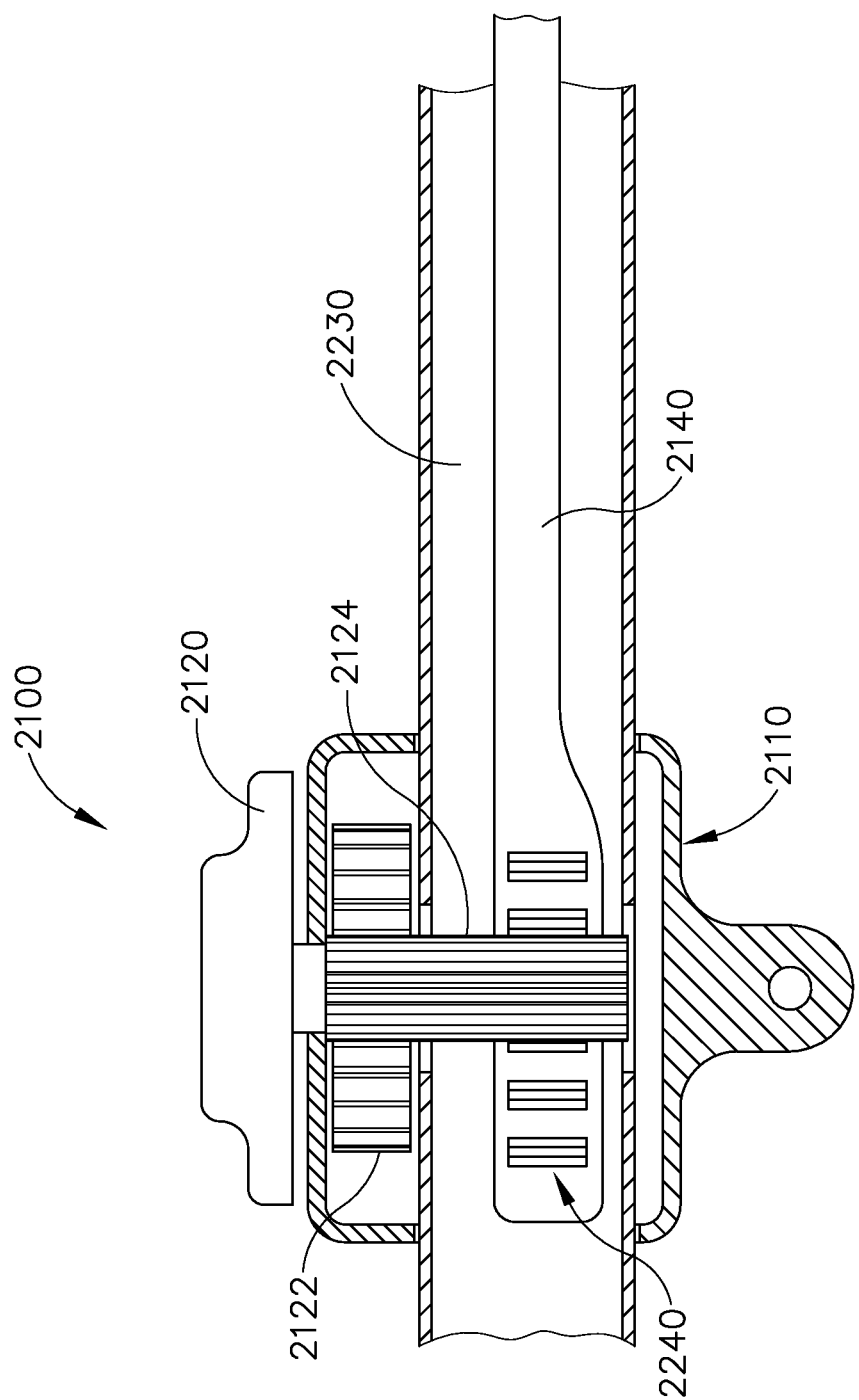
FIG. 52 depicts an enlarged side elevational view of an exemplary articulation control assembly of the instrument of FIG. 51, with a housing of the assembly shown in cross-section.
Figure 53:
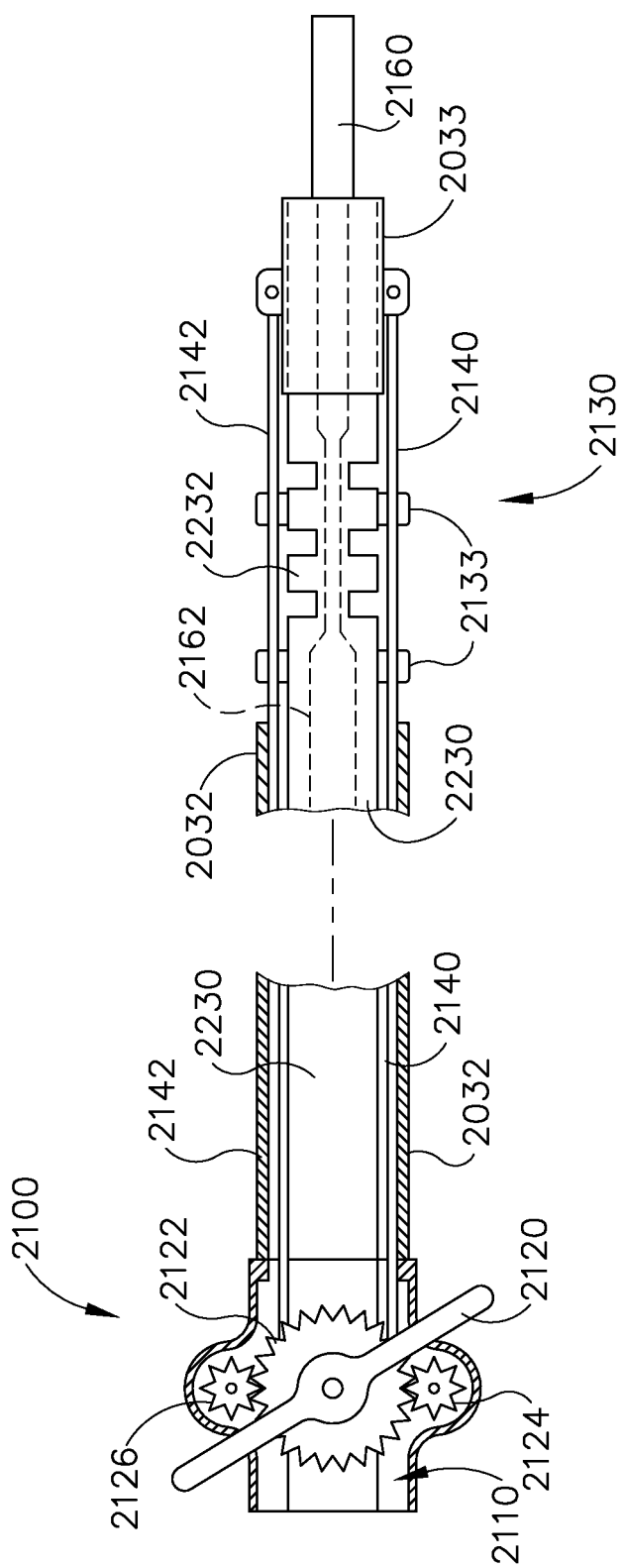
FIG. 53 depicts a top plan view of the articulation control assembly of FIG. 52, with the housing of the assembly shown in cross-section, and the end effector of the instrument of FIG. 51.

FIGS. 51-53 show another exemplary ultrasonic surgical instrument (2000) that is configured and operable substantially similar to instrument (10) except for the differences discussed below. Instrument (2000) of this example comprises a handle assembly (2020), a shaft assembly (2030), and an end effector (2040). Handle assembly (2020) includes a body (2022) that defines a pistol grip (2024). A trigger (2028) is pivotally coupled with body (2022) such that trigger (2028) is pivotable toward and away from pistol grip (2024). An articulation and closure actuation assembly (2100) is slidably coupled with handle assembly (2020) as will be described in greater detail below. It should be understood that handle assembly (2020) may also include a transducer assembly like transducer assembly (12), buttons like buttons (26), and/or various other features as described above with respect to handle assembly (20).

Shaft assembly (2030) of the present example comprises a proximal outer sheath (2032), a distal outer sheath (2033), an inner tubular body (2230), and a flex housing (2232). It should be understood that proximal outer sheath (2032) is shown in cross-section in FIGS. 51 and 53 to reveal internal components of shaft assembly (2030). Shaft assembly (2030) further includes an articulation section (2130), which enables end effector (2040) to be deflected laterally away from the longitudinal axis of the proximal portion of shaft assembly (2030). Proximal outer sheath (2032) distally terminates at the proximal end of articulation section (2130). Distal outer sheath (2033) proximally terminates at the distal end of articulation section (2130). Articulation section (2130) is thus longitudinally interposed between outer sheaths (2032, 2033) Inner tubular body (2230) also distally terminates at the proximal end of articulation section (2130). Flex housing (2232) extends along the length of articulation section (2130). Flex housing (2232) is longitudinally secured relative to inner tubular body (2230), which is further longitudinally secured relative to handle assembly (2020). Flex housing (2232) is thus longitudinally grounded relative to handle assembly (2020), though flex housing (2232) is still configured to bend in lateral deflection during articulation. In some versions, flex housing (2232) is configured similar to the combination of ribbed body portions (132, 134) described above.

Shaft assembly (2030) of the present example further includes a pair of articulation bands (2140, 2142). The distal ends of articulation bands (2140, 2142) are secured to distal outer sheath (2033). The proximal ends of articulation bands (2140, 2142) are coupled with articulation and closure actuation assembly (2100), as will be described in greater detail below. Articulation bands (2140, 2142) pass through a space defined between inner tubular body (2230) and proximal outer sheath (2032). A set of retention collars (133) are positioned about articulation bands (2140, 2142) in articulation section (2130). Articulation bands (2140, 2142) are operable to actuate articulation section (2130), to thereby deflect end effector (2040) laterally to an articulated position. In particular, articulation bands (2140, 2142) translate in an opposing fashion to create and apply a moment to distal outer sheath (2033), thereby providing articulation of articulation section (2130) and end effector (2040), similar to bands (140, 142) described above. It should therefore be understood that end effector (2040) will deflect laterally in the direction of whichever articulation band (2140, 2142) is moving proximally; while the other articulation band (2140, 2142) moves distally.

End effector (2040) of the present example comprises a clamp arm (2044) and an ultrasonic blade (2160). Ultrasonic blade (2160) is formed at the distal end of a waveguide (2162). In the present example, waveguide (2162) is configured and operable identically to waveguide (180) described above, such that waveguide (2162) is configured to bend with articulation section (2130) to achieve an articulated state. Clamp arm (2044) is operable to pivot toward and away from ultrasonic blade (2160), to thereby capture and compress tissue against ultrasonic blade (2160). In particular, one portion of clamp arm (2044) is pivotally coupled with the distal end of flex housing (2232) (or some component that is longitudinally grounded to flex housing (2232)). Another portion of clamp arm (2044) is pivotally coupled with distal outer sheath (2033). Distal outer sheath (2033) is operable to translate longitudinally relative to flex housing (2232) and the other components of shaft assembly (2030) that are longitudinally grounded relative to handle assembly (2022). It should therefore be understood that clamp arm (2044) will pivot relative to blade (2160) in response to longitudinal translation of distal outer sheath (2033) relative to flex housing (2232) and the other components of shaft assembly (2030) that are longitudinally grounded relative to handle assembly (2022).

Articulation and closure actuation assembly (2100) of the present example comprises a housing (2110) and a control knob (2126), which is rotatable relative to housing (2110). As best seen in FIGS. 52-53, where housing (2110) is shown in cross-section, a pinion gear (2122) is unitarily secured to control knob (2126), such that pinion gear (2122) rotates unitarily with control knob (2126) relative to housing (2110). Intermediate gears (2124, 2126) are positioned on opposite sides of pinion gear (2122) and mesh with pinion gear (2122), such that intermediate gears (2124) rotate in response to rotation of control knob (2126) and pinion gear (2122). As shown in FIG. 52, intermediate gear (2124) extends vertically to mesh with a rack (2240) of articulation band (2140), providing a rack and pinion relationship between intermediate gear (2124) and articulation band (2140). Thus, when intermediate gear (2124) rotates, articulation band (2140) translates longitudinally. Articulation band (2140) will therefore translate longitudinally in response to rotation of control knob (2126). While not shown, intermediate gear (2126) meshes with a rack of articulation band (2142) in a similar fashion. Articulation bands (2140, 2142) will thus translate longitudinally in an opposing fashion in response to rotation of control knob (2126). It should therefore be understood that articulation section (2130) will bend to deflect end effector (2040) in a first direction when control knob (2126) is rotated in a first direction; and will bend to deflect end effector (2040) in a second direction when control knob (2126) is rotated in a second direction. In some versions, knob (2126) is oriented to extend along a plane that is parallel with the longitudinal axis of shaft assembly (2030) when articulation section (213) is straight; and obliquely relative to the longitudinal axis of shaft assembly (2030) when articulation section (213) is bent, such that control knob (2126) provides visual feedback indicating the state of articulation.

As noted above, articulation and closure actuation assembly (2100) is configured to slide longitudinally relative to handle assembly (2020). Articulation and closure actuation assembly (2100) is pivotally coupled with trigger (2028) via a link (2090). In particular, one end of link (2090) is pivotally coupled with the underside of housing (2110) and another end of link (2090) is pivotally coupled with the upper end of trigger (2028). Thus, as trigger (2028) is pivoted toward pistol grip (2024), link (2090) drives articulation and closure actuation assembly (2100) distally relative to handle assembly (2020). As trigger (2028) is pivoted back away from pistol grip (2024), link (2090) drives articulation and closure actuation assembly (2100) proximally relative to handle assembly (2020). When articulation and closure actuation assembly (2100) translates relative to handle assembly (2020), intermediate gears (2124, 2126) drive articulation bands (2140, 2142) longitudinally together in the same direction simultaneously. When articulation bands (2140, 2142) translate longitudinally together in the same direction simultaneously, articulation bands (2140, 2142) drive distal outer sheath (2033) longitudinally. Such longitudinal motion of distal outer sheath (2033) actuates clamp arm (2044) as described above. It should therefore be understood that, as trigger (2028) is pivoted toward pistol grip (2024), clamp arm (2044) is driven toward blade (2160) via link (2090), articulation and closure actuation assembly (2100), articulation bands (2140, 2142), and distal outer sheath (2033). Likewise, as trigger (2028) is pivoted away from pistol grip (2024), clamp arm (2044) is driven away from blade (2160) via link (2090), articulation and closure actuation assembly (2100), articulation bands (2140, 2142), and distal outer sheath (2033).

It should be understood that articulation and closure actuation assembly (2100) may include one or more features that are operable to selectively lock the straight/articulation state of articulation section (2130) or at least resist a change in the straight/articulation state of articulation section (2130). By way of example only, such resistance may be provided through friction, detent features, etc. Other suitable ways in which articulation and closure actuation assembly (2100) may selectively lock the straight/articulation state of articulation section (2130) or at least resist a change in the straight/articulation state of articulation section (2130) will be apparent to those of ordinary skill in the art in view of the teachings herein.

VI. EXEMPLARY ULTRASONIC SURGICAL INSTRUMENT WITH MOTORIZED ARTICULATION

Figure 54:
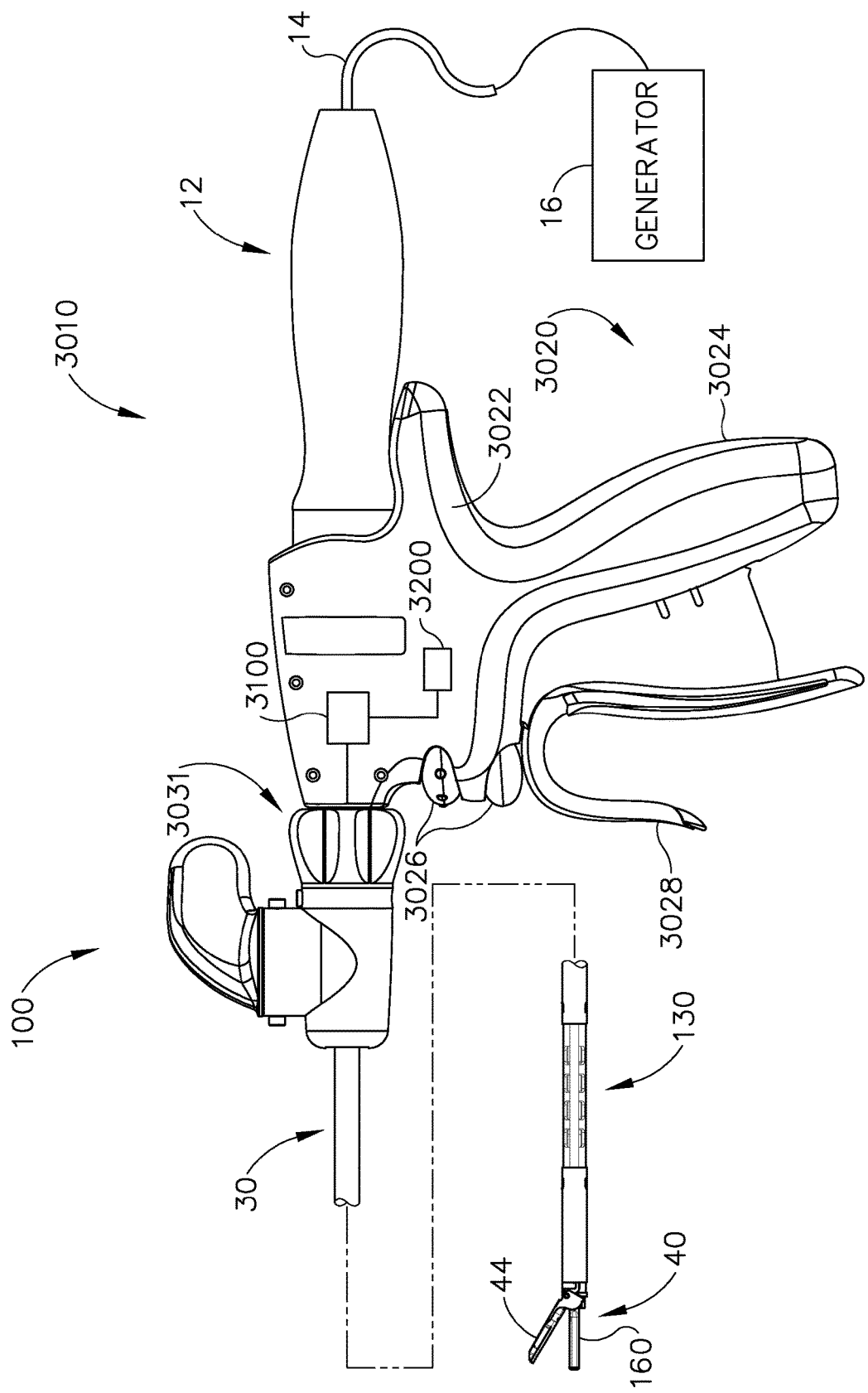
FIG. 54 depicts a side elevational view of an exemplary alternative ultrasonic surgical instrument.

The above examples are discussed in the context of manual control of articulation in a shaft assembly. However, it should also be understood that articulation may be motorized. For instance, FIG. 54 shows an exemplary instrument (3010) that is in many ways similar to instrument (10) described above. Instrument (3010) of this example includes a handle assembly (3020), a shaft assembly (30), and an end effector (40). Handle assembly (3020) comprises a body (3022) including a pistol grip (3028) and a pair of buttons (3026). Handle assembly (3020) also includes a trigger (3028) that is pivotable toward and away from pistol grip (3024). End effector (40) includes an ultrasonic blade (160) and a pivoting clamp arm (44). Clamp arm (44) is coupled with trigger (3028) such that clamp arm (44) is pivotable toward ultrasonic blade (160) in response to pivoting of trigger (3028) toward pistol grip (3024); and such that clamp arm (44) is pivotable away from ultrasonic blade (160) in response to pivoting of trigger (3028) away from pistol grip (3024).

An ultrasonic transducer assembly (12) extends proximally from body (3022) of handle assembly (3020). Transducer assembly (12) is coupled with a generator (16) via a cable (14), such that transducer assembly (12) receives electrical power from generator (16). Piezoelectric elements in transducer assembly (12) convert that electrical power into ultrasonic vibrations. Generator (16) may include a power source and control module that is configured to provide a power profile to transducer assembly (12) that is particularly suited for the generation of ultrasonic vibrations through transducer assembly (12).

Shaft assembly (30) of the present example extends distally from handle assembly (3020). Shaft assembly (30) includes an articulation section (130), which is located at a distal portion of shaft assembly (30), with end effector (40) being located distal to articulation section (130). A knob (3031) is secured to a proximal portion of proximal outer sheath (32). Knob (3031) is rotatable relative to body (3022), such that shaft assembly (30) is rotatable about a longitudinal axis relative to handle assembly (3020). Such rotation may provide rotation of end effector (40), articulation section (130), and shaft assembly (30) unitarily. Of course, rotatable features may simply be omitted if desired. Articulation section (130) is operable to selectively position end effector (40) at various lateral deflection angles relative to a longitudinal axis defined by outer sheath (32). Articulation section (130) may take a variety of forms, including but not limited to any of the forms described herein.

It should be understood that all of the above described features of instrument (3010) are substantially identical to the same features of instrument (10), except for the differences described below. In particular, instrument (3010) of this example lacks manually operated articulation control assembly (100). Instead, instrument (3010) includes a motor (3100) that is coupled with articulation section (130) to drive articulation section (130) in a motorized fashion. Various suitable ways in which motor (3100) may be coupled with articulation section (130) to drive articulation section (130) in a motorized fashion will be apparent to those of ordinary skill in the art in view of the teachings herein. A user input feature (3200) is in communication with motor (3100) and is operable to selectively activate motor (3100) in response to user input. Various suitable forms that user input feature (3200) may take will be apparent to those of ordinary skill in the art in view of the teachings herein. It should also be understood that more than one user input feature (3200) may be provided (e.g., one user input feature (3200) for each direction of articulation, etc.).

In some versions, motor (3100) receives power from an external source (e.g., generator (16), etc.) via cable (14). In some other versions, motor (3100) receives power from an internal source (e.g., one or more batteries or other portable power sources in body (3022) of handle assembly (3020), etc.). It should also be understood that motor (3100) may be located at any suitable position within body (3022) of handle assembly (3020). Alternatively, motor (3100) may be located external to body (3022). Other suitable ways in which motor (3100) may be incorporated in instrument (3010) to drive articulation section (130) will be apparent to those of ordinary skill in the art in view of the teachings herein.

While instrument (3010) is described above as providing motorized driving of articulation section (130), it should be understood that instrument (3010) may instead incorporate any of the other articulation sections described herein. In other words, any of the articulation sections described herein may be driven in a motorized fashion.

VII. EXEMPLARY ULTRASONIC SURGICAL INSTRUMENT WITH RESTRICTED ARTICULATION

In some instances, it may be desirable to restrict the articulation angle of waveguide (180). For instance, if waveguide (180) is articulated from the longitudinal axis defined by proximal outer sheath (32) at too steep an angle, waveguide (180) could permanently deform leading to undesirable effects. Restricting the maximum articulation of waveguide (180) may therefore help maintain the structural integrity of waveguide (180). A merely illustrative example of how the articulation angle may be restricted will be described in greater detail below.

A. Exemplary End Effector and Acoustic Drivetrain

Figure 55A:
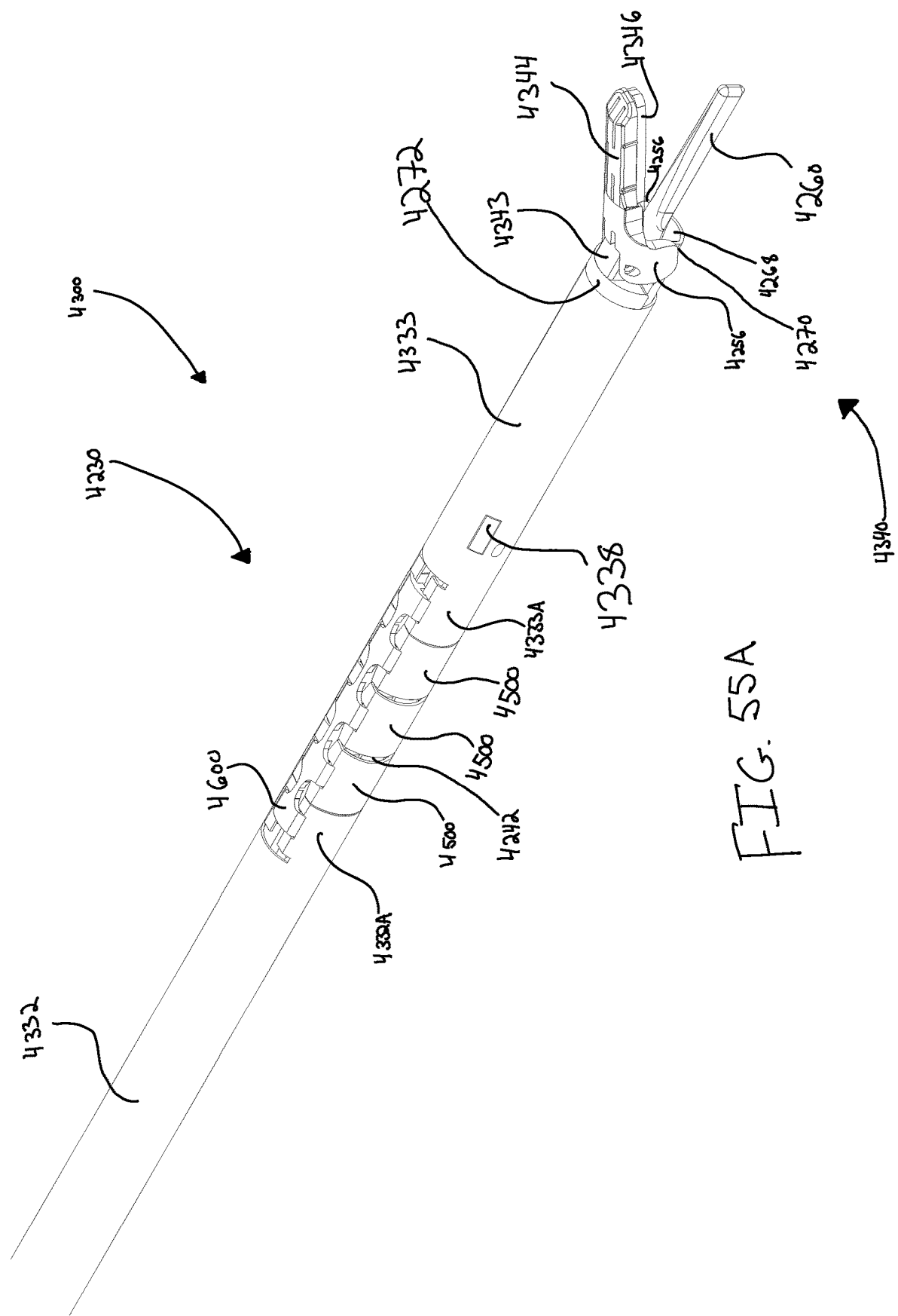
FIG. 55A depicts a perspective view of an articulation section of an exemplary alternative shaft assembly and an end effector that may be incorporated into the instrument of FIG. 1.

FIG. 55A illustrates an exemplary shaft assembly (4300) and an exemplary end effector (4340). Shaft assembly (4300) and end effector (4340) can be utilized in instrument (10), substituting for shaft assembly (30) and end effector (40). End effector (4340) is substantially similar to end effector (40). End effector (4340) includes an ultrasonic blade (4260) and a pivoting clamp arm (4344). Claim arm (4344) includes a clamp pad (4346) that is secured to the underside of clamp arm (4344), facing ultrasonic blade (4260). Clamp pad (4346) may comprise polytetrafluoroethylene (PTFE) and/or any other suitable material(s).

Clamp arm (4344) is pivotally secured to a distally projecting tongue (4343) of an upper distal shaft element (4272), which is fixedly secured within a distal portion of a distal outer sheath (4333). Lower distal shaft element (4270) is slidably disposed within the distal portion of distal outer sheath (4333). Trigger (28) is operable to translate lower distal shaft element (4270) along a path that is parallel to the longitudinal axis defined by distal outer sheath (4333). Specifically, trigger (28) can translate lower distal shaft element (4272) proximally when trigger (28) is pivoted toward pistol grip (24) and distally when trigger (28) is pivoted away from pistol grip (24). A pair or arms (4256) extend transversely from clamp arm (4344) and are pivotally secured to lower distal shaft element (4270). Therefore, clamp arm (4344) is coupled with trigger (28) such that clamp arm (4344) is pivotable toward ultrasonic blade (4260) in response to pivoting of trigger (28) toward pistol grip (24); and such that clamp arm (4344) is pivotable away from ultrasonic blade (4260) in response to pivoting of trigger (28) away from pistol grip (24). Various suitable ways in which clamp arm (4344) may be coupled with trigger (28) will be apparent to those of ordinary skill in the art in view of the teachings herein. In some versions, one or more resilient members are used to bias clamp arm (4344) and/or trigger (28) to the open position shown in FIG. 55A. Drive features enabling trigger (28) to close clamp arm (4344) are the same for the drive features described above enabling trigger (28) to close clamp arm (44).

Blade (4260) of the present example is operable to vibrate at ultrasonic frequencies in order to effectively cut through and seal tissue, particularly when the tissue is being compressed between clamp pad (4346) and blade (4260). Blade (4260) is positioned at the distal end of an acoustic drivetrain. This acoustic drivetrain includes transducer assembly (12) and an acoustic waveguide (4280). Acoustic waveguide (4280) comprises a flexible portion (4266). Transducer assembly (12) includes a set of piezoelectric discs (not shown) located proximal to a horn (not shown) of waveguide (4280). The piezoelectric discs are operable to convert electrical power into ultrasonic vibrations, which are then transmitted along waveguide (4280), including flexible portion (4266) of waveguide (4280) to blade (4260) in accordance with known configurations and techniques. By way of example only, this portion of the acoustic drivetrain may be configured in accordance with various teachings of various references that are cited herein.

Figure 56:
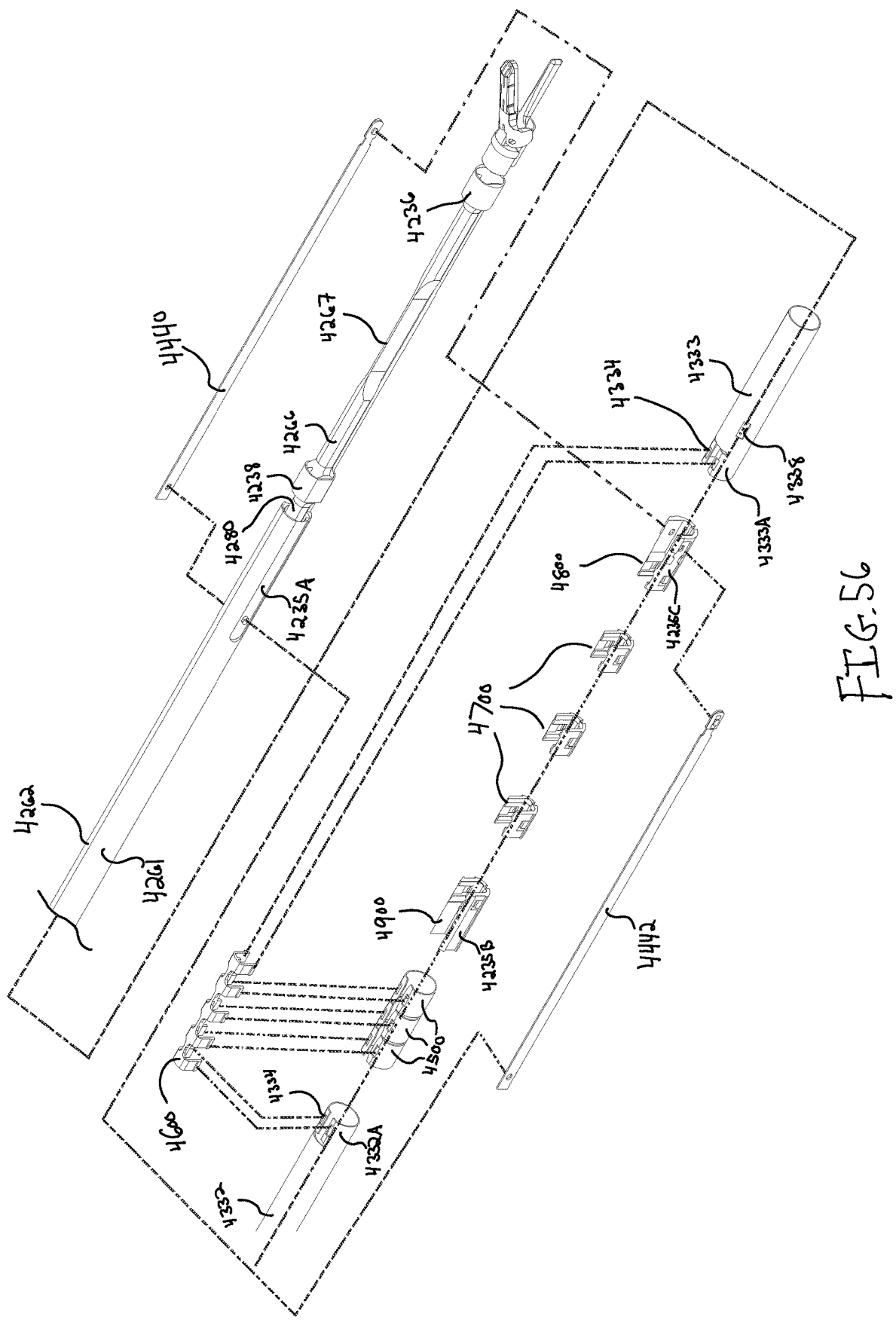
FIG. 56 depicts an exploded perspective view of the articulation section of FIG. 55A.

As best seen in FIG. 56, flexible portion (4266) of waveguide (4280) includes a distal flange (4236), a proximal flange (4238), and a narrowed section (4267) located between flanges (4236, 4238). In the present example, flanges (4236, 4238) are located at positions corresponding to nodes associated with resonant ultrasonic vibrations communicated through flexible portion (4266) of waveguide (4280). Narrowed section (4267) is configured to allow flexible portion (4266) of waveguide (4280) to flex without significantly affecting the ability of flexible portion (4266) of waveguide (4280) to transmit ultrasonic vibrations. By way of example only, narrowed section (4267) may be configured in accordance with one or more teachings of U.S. Pub. No. 2014/0005701, issued as U.S. Pat. No. 9,393,037 Jul. 19, 2016 and/or U.S. Pub. No. 2014/0114334, issued as U.S. Pat. No. 9,095,367 on Aug. 4, 2015, the disclosures of which are incorporated by reference herein. It should be understood that waveguide (4280) may be configured to amplify mechanical vibrations transmitted through waveguide (4280). Furthermore, waveguide (4280) may include features operable to control the gain of the longitudinal vibrations along waveguide (4280) and/or features to tune waveguide (4280) to the resonant frequency of the system. Various suitable ways in which waveguide (4280) may be mechanically and acoustically coupled with transducer assembly (12) will be apparent to those of ordinary skill in the art in view of the teachings herein.

In the present example, the distal end of blade (4260) is located at a position corresponding to an anti-node associated with resonant ultrasonic vibrations communicated through flexible portion (4266) of waveguide (4280), in order to tune the acoustic assembly to a preferred resonant frequency $f_o$ when the acoustic assembly is not loaded by tissue. When transducer assembly (12) is energized, the distal end of blade (4260) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (12) of the present example is activated, these mechanical oscillations are transmitted through waveguide (4280) to reach blade (4260), thereby providing oscillation of blade (4260) at the resonant ultrasonic frequency. Thus, when tissue is secured between blade (4260) and clamp pad (4346), the ultrasonic oscillation of blade (4260) may simultaneously sever the tissue and denature the proteins in adjacent tissue cells, thereby providing a coagulative effect with relatively little thermal spread. In some versions, an electrical current may also be provided through blade (4260) and clamp arm (4344) to also cauterize the tissue. While some configurations for an acoustic transmission assembly and transducer assembly (12) have been described, still other suitable configurations for an acoustic transmission assembly and transducer assembly (12) will be apparent to one or ordinary skill in the art in view of the teachings herein. Similarly, other suitable configurations for end effector (4340) will be apparent to those of ordinary skill in the art in view of the teachings herein.

B. Exemplary Shaft Assembly and Alternative Articulation Section

When incorporated into instrument (10) described above, shaft assembly (4300) of the present example would extend distally from handle assembly (20). As shown in FIGS. 55A-56, shaft assembly (4300) includes distal outer sheath (4333) and a proximal outer sheath (4332) that encloses clamp arm (4344) drive features and the above-described acoustic transmission features. Shaft assembly (4300) further includes an articulation section (4230), which is located at a distal portion of shaft assembly (4300), with end effector (4340) being located distal to articulation section (4230).

Similar to articulation section (130), articulation section (4230) is operable to selectively position end effector (4340) at various lateral deflection angles relative to a longitudinal axis defined by outer sheath (4332). Articulation section (4230) may take a variety of forms. By way of example only, articulation section (4230) may be configured in accordance with one or more teachings of U.S. Pub. No. 2012/0078247, issued as U.S. Pat. No. 9,402,682 on Aug. 2, 2016, the disclosure of which is incorporated by reference herein. As another merely illustrative example, articulation section (4230) may be configured in accordance with one or more teachings of U.S. Pub. No. 2014/0005701, issued as U.S. Pat. No. 9,393,037 on Jul. 19, 2016 and/or U.S. Pub. No. 2014/0114334, issued as U.S. Pat. No. 9,095,367 on Aug. 4, 2015, the disclosures of which are incorporated by reference herein. Various other suitable forms that articulation section (4230) may take will be apparent to those of ordinary skill in the art in view of the teachings herein.

As illustrated in FIGS. 55A-56, articulation section (4230) of this example comprises a set of three retention collars (4500), a distal mating feature (4332A) of proximal outer sheath (4332), a proximal mating feature (4333A) of distal outer sheath (4333), a set of body portions (4700, 4800, 4900), a flexible locking feature (4600), and a pair of articulation bands (4440, 4442) extending along channels (4235A-C) defined by translation members (4261, 4262), proximal body portion (4900) and distal body portion (4800). Distal mating feature (4332A) and proximal mating feature (4333A) both comprise insert holes (4334).

Figure 57:
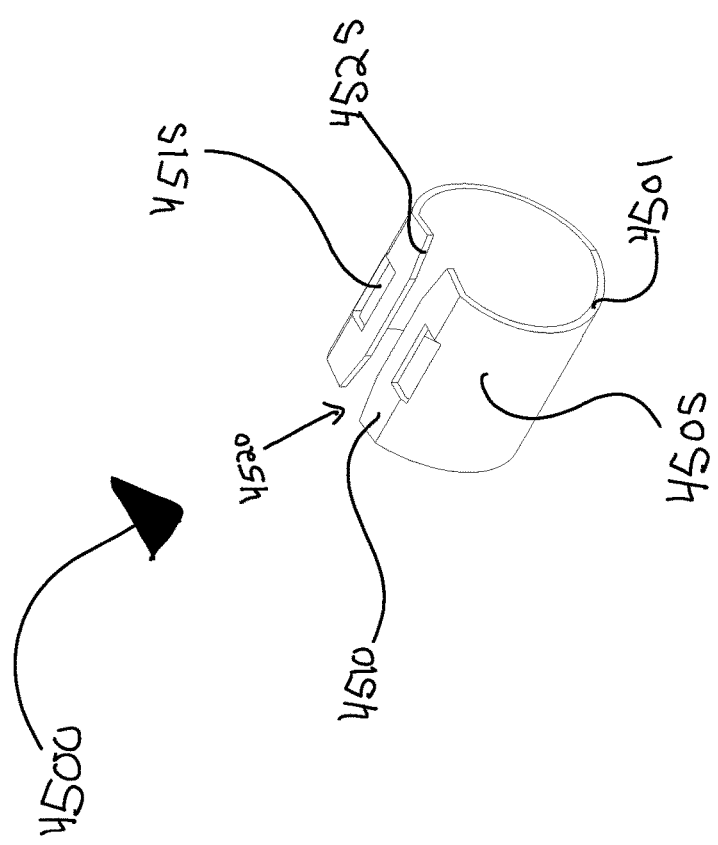
FIG. 57 depicts a perspective view of a retention collar of the articulation section of FIG. 55A.
Figure 58:
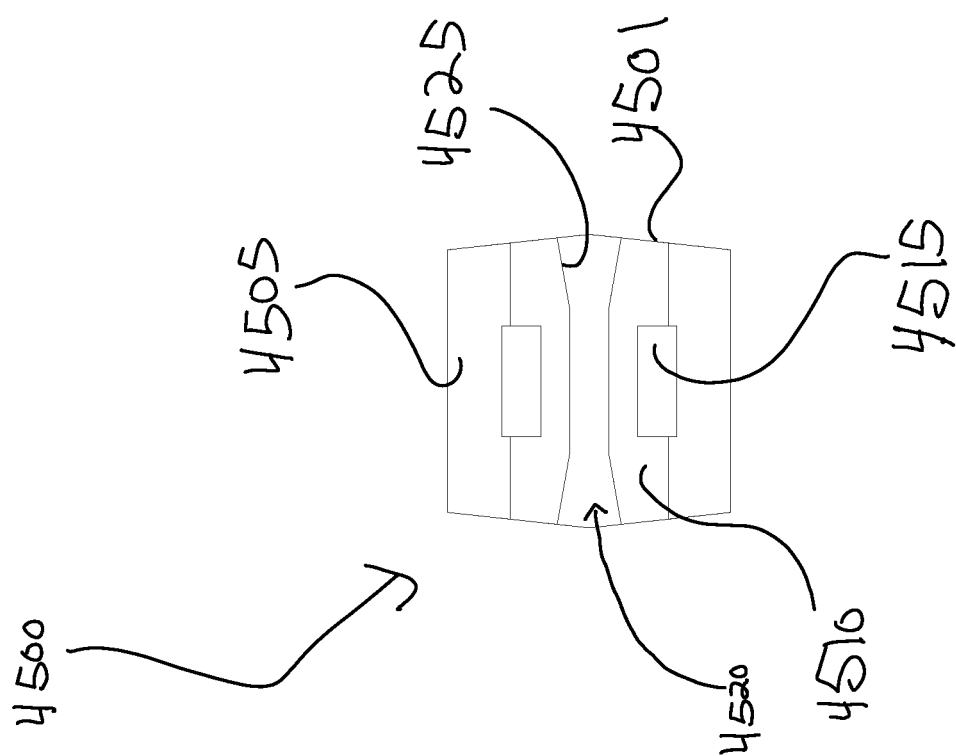
FIG. 58 depicts a top elevational view of the retention collar of FIG. 55A.
Figure 68:
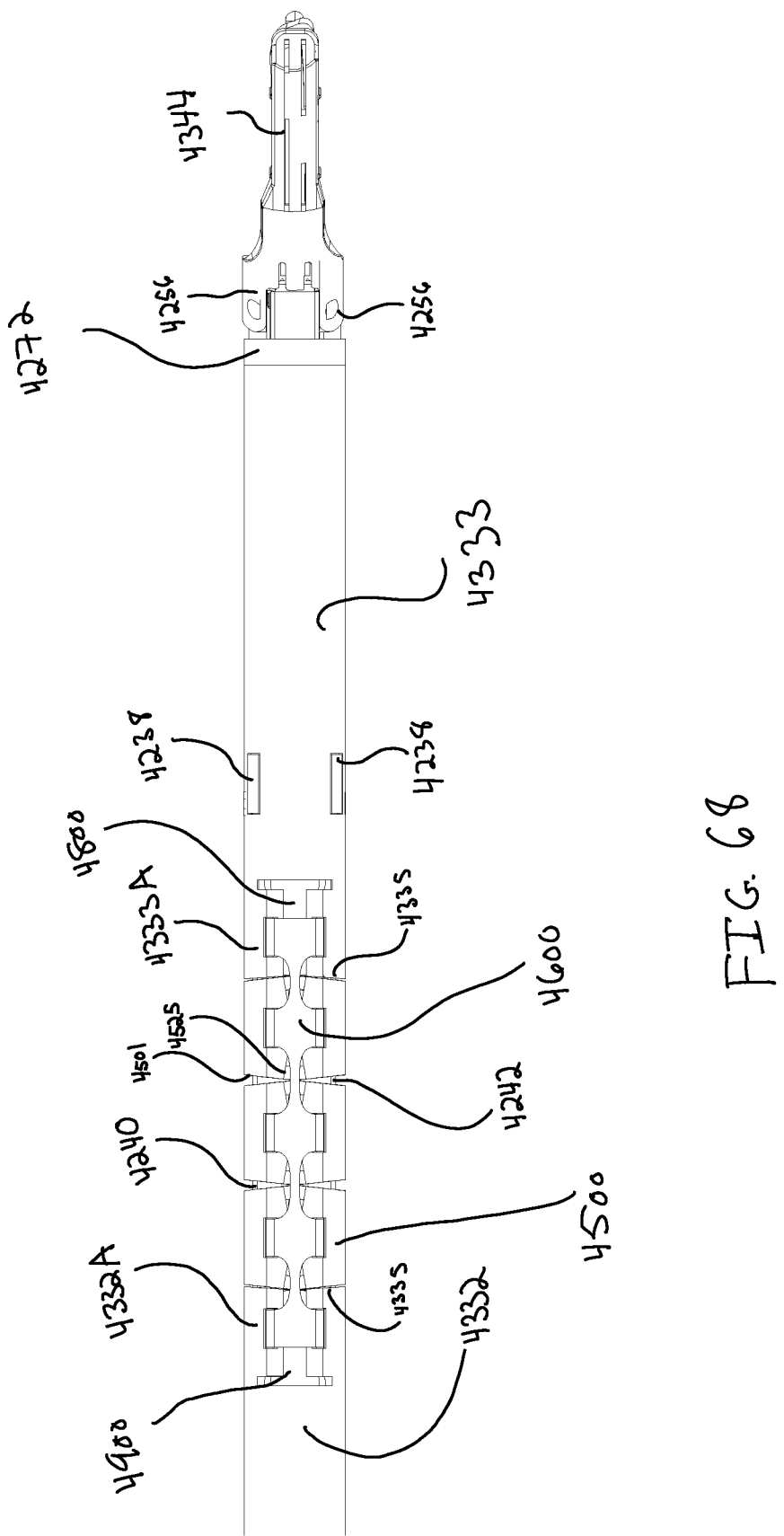
FIG. 68 depicts a top elevational view of the articulation section of the shaft assembly and the end effector of the surgical instrument of FIG. 55A.

As illustrated in FIGS. 57-58, each retention collar (4500) comprises a first angled contact surface (4501), a second angled contact surface (4525), a circular segment surface (4505), and a pair of flattened surfaces (4510) extending inwardly from circular segment surface (4505). Flattened surfaces (4510) define a pathway (4520) and a pair of insert holes (4515). First angled contact surface (4501) is configured to contact a complementary first angled contact surface (4501) of another retention collar (4500). Distal mating feature (4332A) of proximal outer sheath (4332) and proximal mating feature (4333A) of distal outer sheath (4333) are substantially similar to retention collar (4500), but without first angled contact surface (4501) and second angled contact surface (4525). As best seen in FIG. 68, distal mating feature (4332A) and proximal mating feature (4333A) each have a first angled contact surface (4335) that complements first angled contact surfaces (4501) of retention collars (4501).

Figure 59:
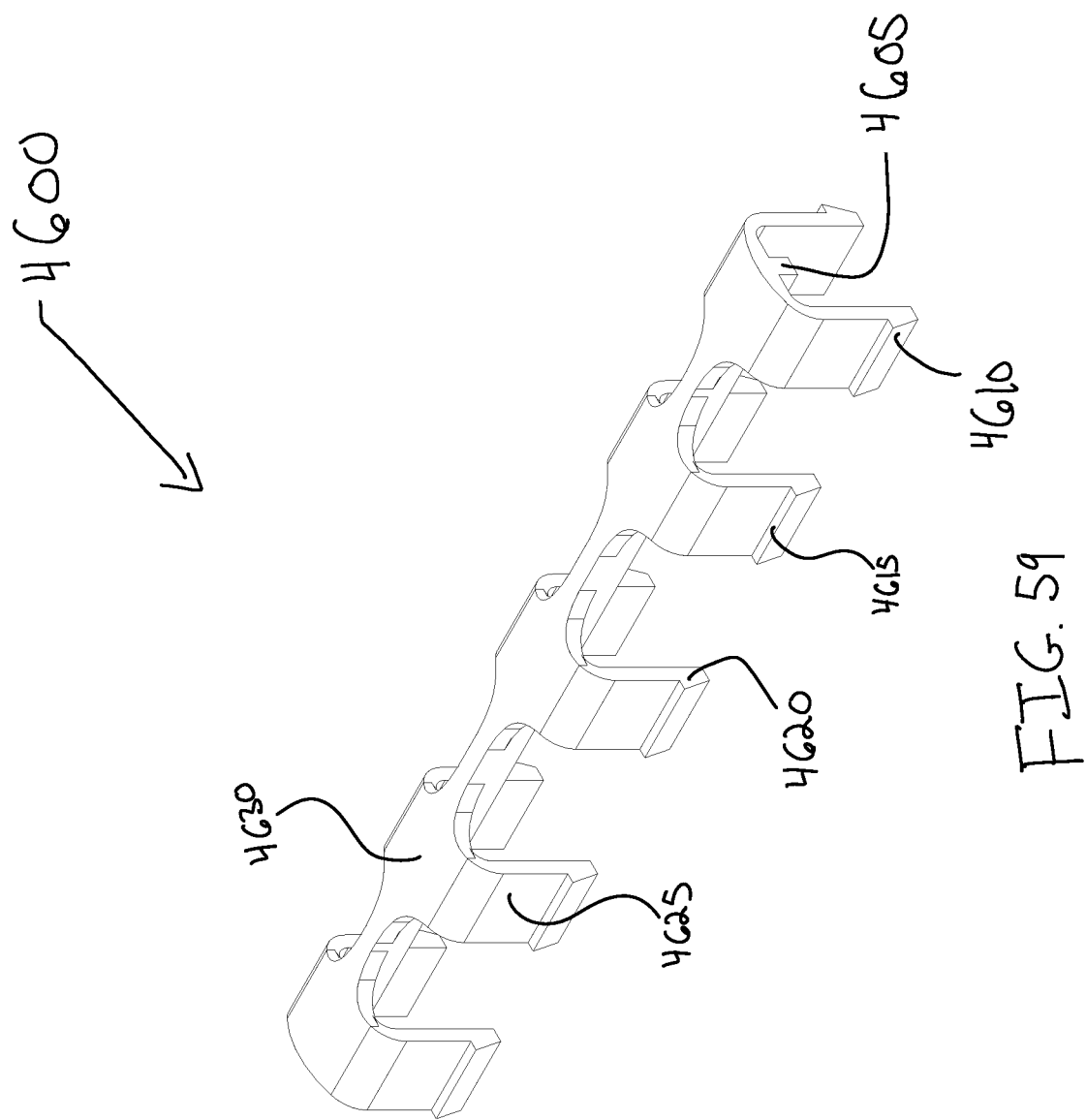
FIG. 59 depicts a perspective view of a flexible locking feature of the articulation section of FIG. 55A.
Figure 60:
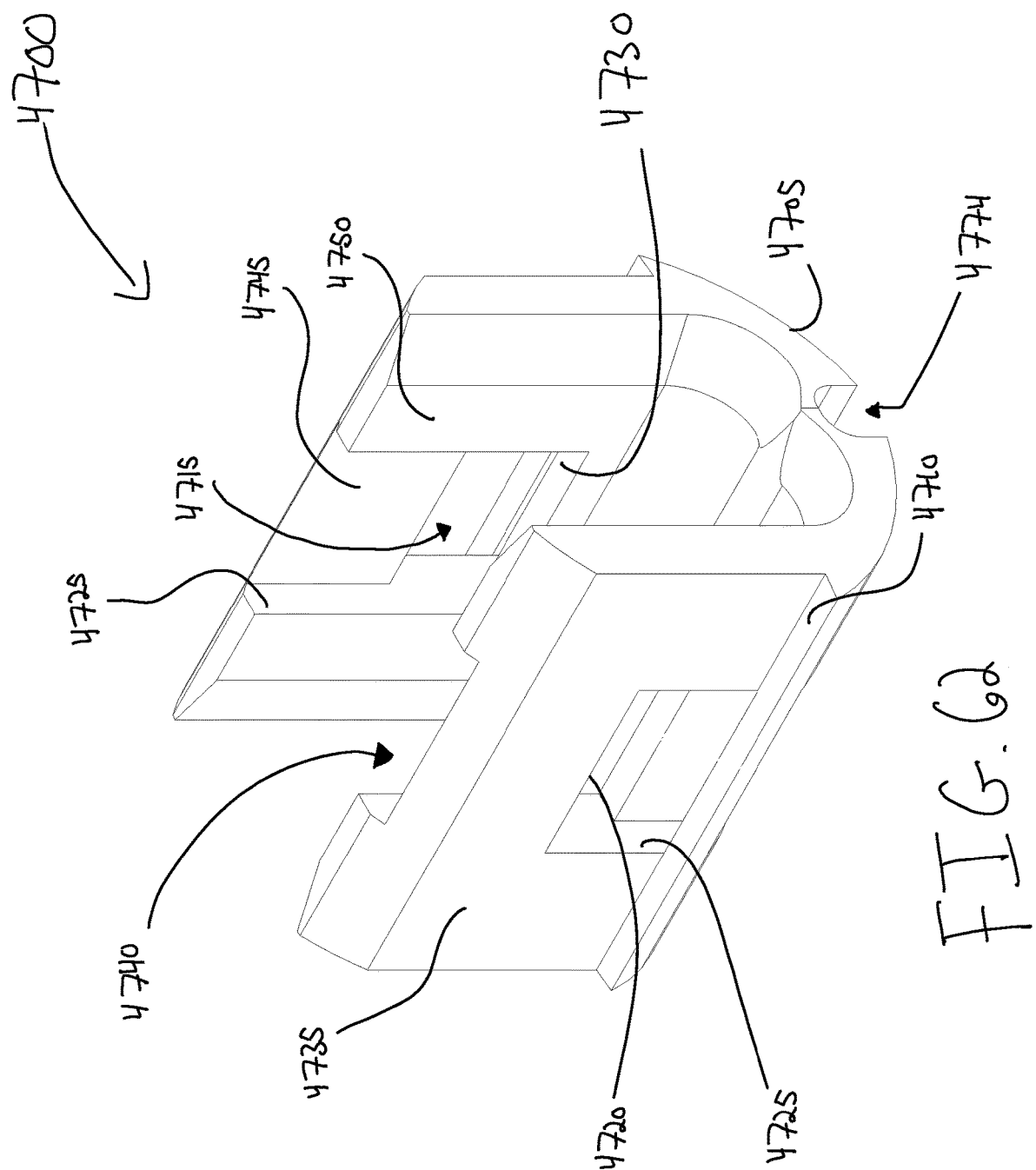
FIG. 60 depicts a front elevational view of the flexible locking feature of FIG. 55A.

As illustrated in FIGS. 59-60, flexible locking feature (4600) comprises a connecting spine (4630), pairs of resilient legs (4625) extending from connecting spine (4630), tabs (4620) located at the termination of each resilient leg (4625), and a rib (4605) running longitudinally along connecting spine (4630) and in between each pair of resilient legs (4625). Each tab (4625) further comprises an angled surface (4610) and a transverse surface (4615).

As illustrated in FIGS. 62-63, each intermediate body portion (4700) comprises an arched base (4705), an articulation band ledge (4710), a tab window (4715), an exterior surface (4735), an interior surface (4750), a leg channel (4740), and a cable channel (4774). Tab window (4715) is defined by transverse walls (4725), tab floor (4730), and tab ceiling (4720). Leg channel (4740) is defined by interior tab contact surface (4745) and transverse walls (4725). Articulation band ledge (4710) extends transversely from exterior surface and terminates at arched base (4705). Each articulation band ledge (4710) is configured to at least partially support or otherwise accommodate a corresponding articulation band (4440, 4442) between second channel for articulation band (4235B) and third channel for articulation band (4235C). Leg channel (4740) is configured and dimensioned to act as a guide for insertion of resilient legs (4625) of flexible locking feature (4600). Cable channel (4774) provides a linear path for a drive feature (e.g., cable (174) as described above) to communicate with trigger (28) in order to move clamp arm (4344).

Figure 64:
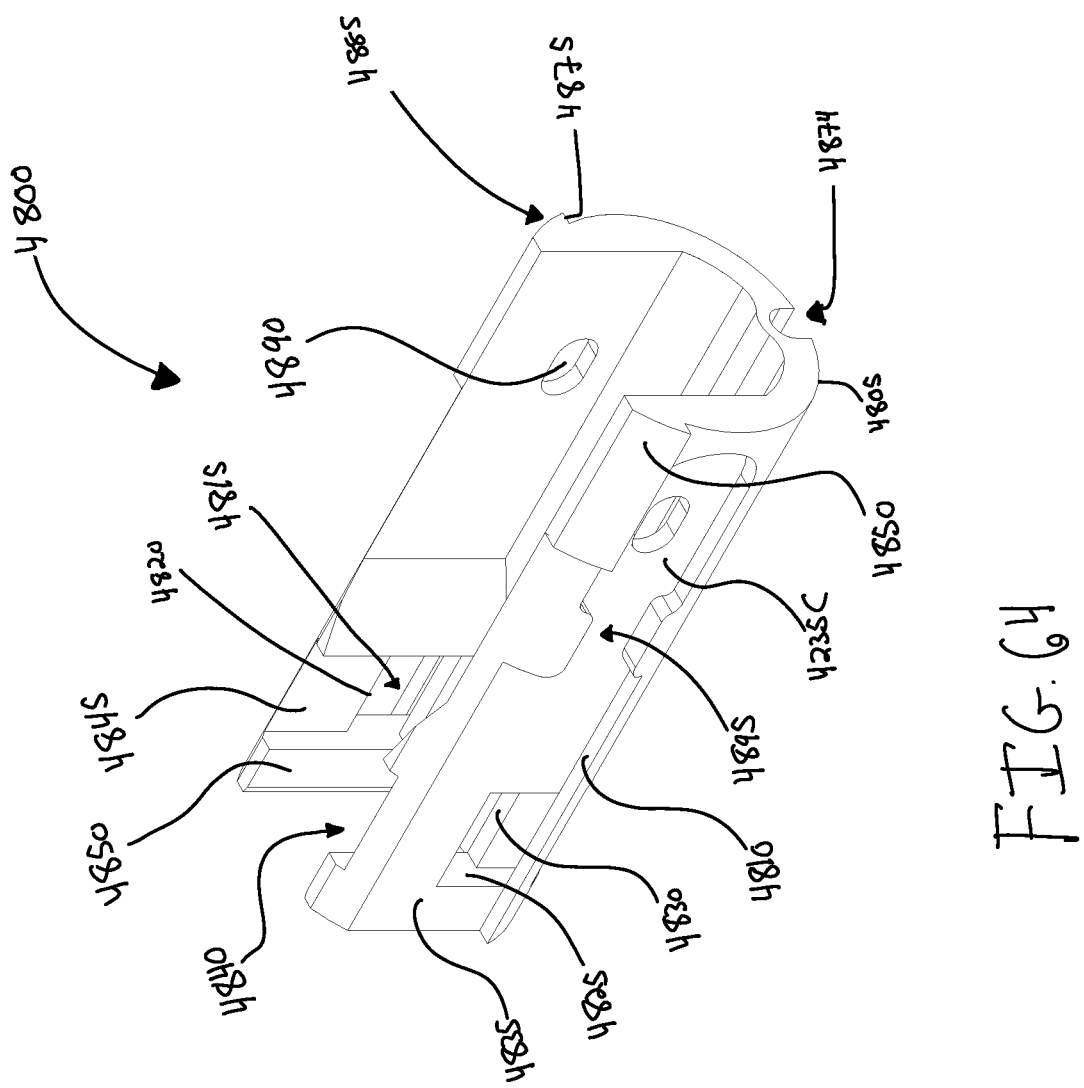
FIG. 64 depicts a perspective view of the distal body portion of FIG. 55A.
Figure 65:
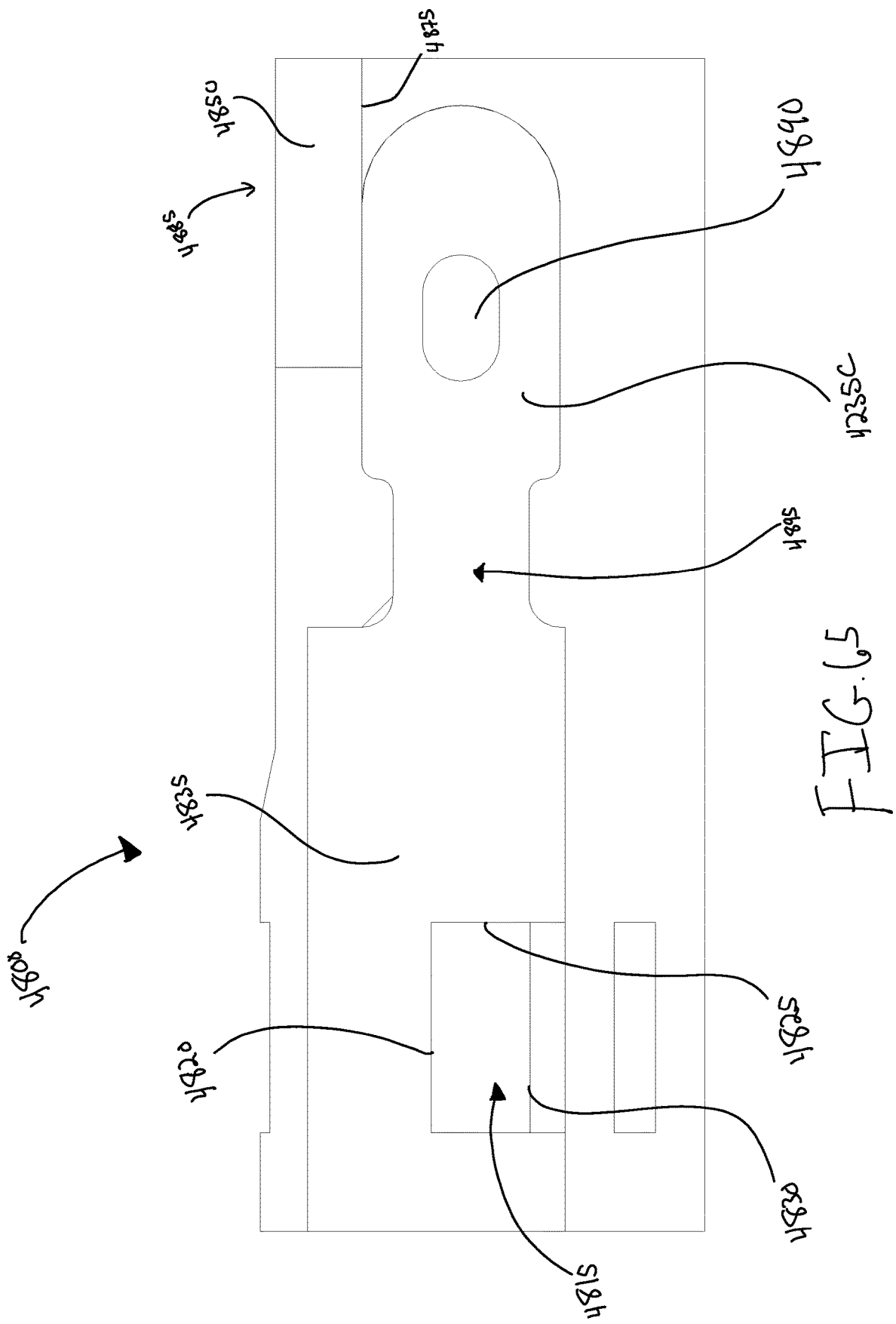
FIG. 65 depicts a side elevational view of the distal body portion of FIG. 55A.

FIGS. 64-65 illustrate distal body portion (8400). Similarly to intermediate body portion (4700), distal body portion (4800) comprises an arched base (4805), an articulation band ledge (4810), a tab window (4815), an exterior surface (4835), an interior surface (4850), a leg channel (4840), and a cable channel (4874). Tab window (4815) is defined by transverse walls (4825), tab floor (4830), and tab ceiling (4820). Leg channel (4840) is defined by interior tab contact surface (4845) and transverse walls (4825).

All of the features mentioned above for the distal body portion (4800) are substantially the same as their counterparts of intermediate body portion (4700). However, distal body portion (4800) additionally comprises a resilient tab (4885), a mating feature for articulation band (4890), a narrowed pathway (4895), and third channel for articulation band (4235C). Resilient tab (4885) further comprises a transverse surface (4875) and an extending surface (4850). Articulation band ledge (4810) extends transversely from exterior surface and terminates at arched base (4805). Each articulation band ledge (4810) is configured to at least partially support or otherwise accommodate a corresponding articulation band (4440, 4442) between second channel for articulation band (4235B) and third channel for articulation band (4235C). Leg channel (4840) is configured and dimensioned to act as a guide for insertion of resilient legs (4625) of flexible locking feature (4600). Cable channel (4874) provides a linear path for a drive feature (e.g., cable (174) as described above) to communicate with trigger (28) in order to move clamp arm (4344).

Figure 66:
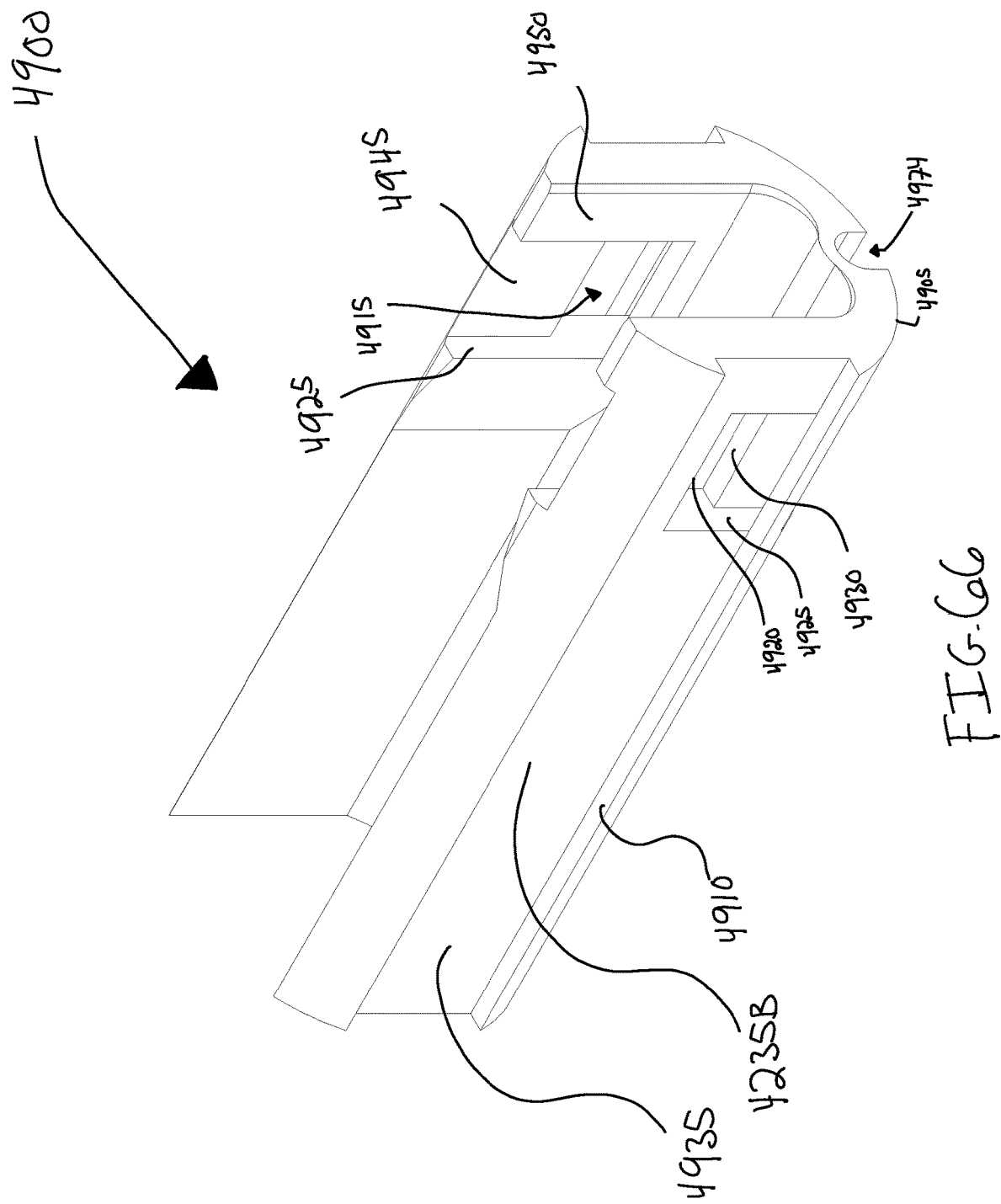
FIG. 66 depicts a perspective view of the proximal body portion of FIG. 55A.

FIG. 66 illustrates proximal body portion (4900). Similarly to intermediate body portion (4700), proximal body portion (4900) comprises an arched base (4905), an articulation band ledge (4910), a tab window (4915), an exterior surface (4935), an interior surface (4950), a leg channel (4940), and a cable channel (4974). Tab window (4915) is defined by transverse walls (4925), tab floor (4930), and tab ceiling (4920). Leg channel (4940) is defined by interior tab contact surface (4945) and transverse walls (4925).

All of the features mentioned above for the proximal body portion (4900) are substantially the same as their counterparts for both intermediate body portions (4700) and distal body portion (4900). However, proximal body portion (4900) additionally comprises second channel (4235B) for articulation band (4440, 4442). Articulation band ledge (4910) extends transversely from exterior surface and terminates at arched base (4905). Each articulation band ledge (4910) is configured to at least partially support or otherwise accommodate a corresponding articulation band (4440, 4442) as articulation band ledge (4910) helps partially define second channel (4235B) for articulation band (4440, 4442). Leg channel (4940) is configured and dimensioned to act as a guide for insertion of resilient legs (4625) of flexible locking feature (4600). Cable channel (4974) provides a linear path for a drive feature (e.g., cable (174) as described above) to communicate with trigger (28) in order to move clamp arm (4344).

Figure 55C:
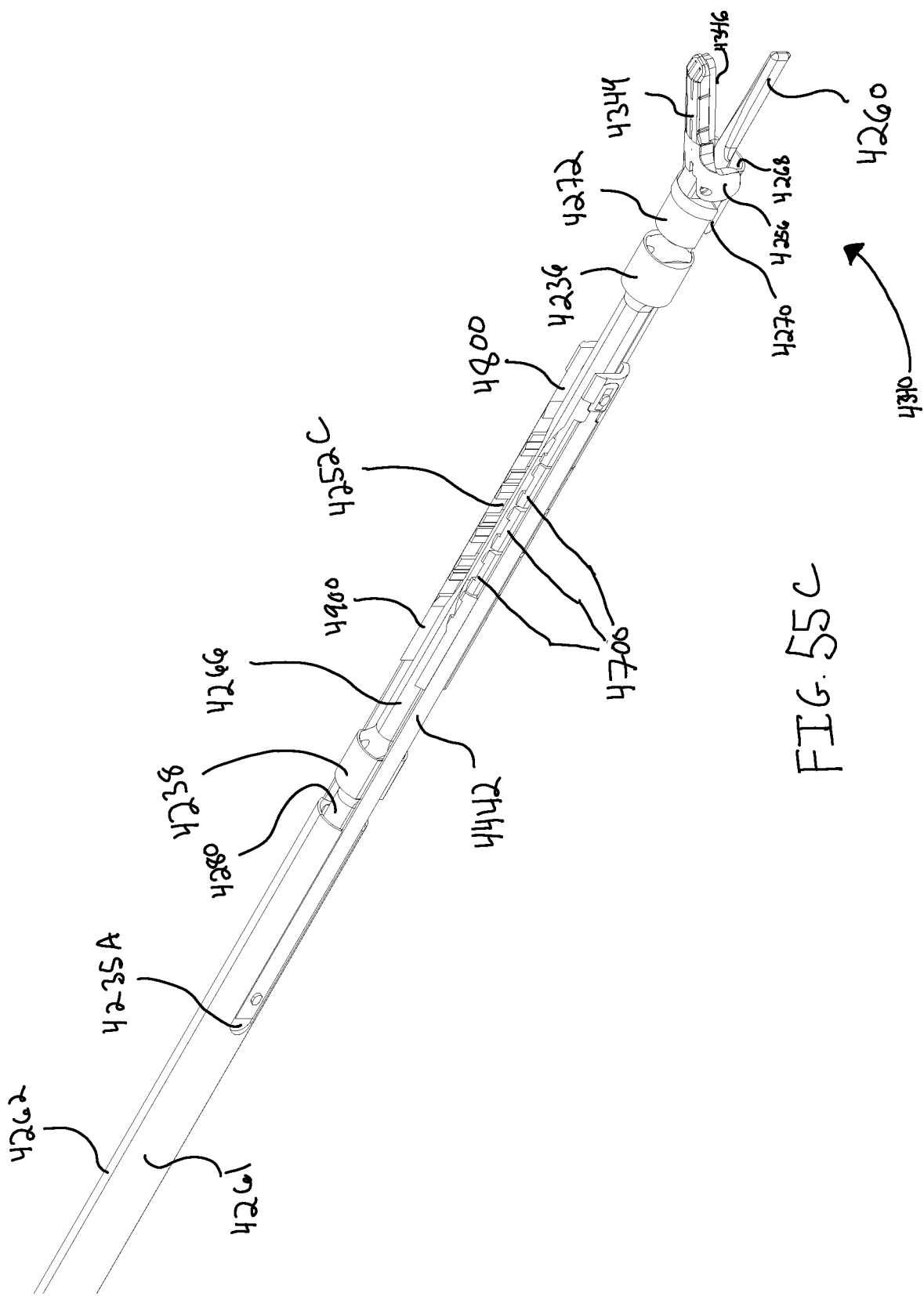
FIG. 55C depicts a perspective view of the articulation section of the shaft assembly and the end effector of FIG. 55A with certain elements omitted to show greater detail.
Figure 55D:
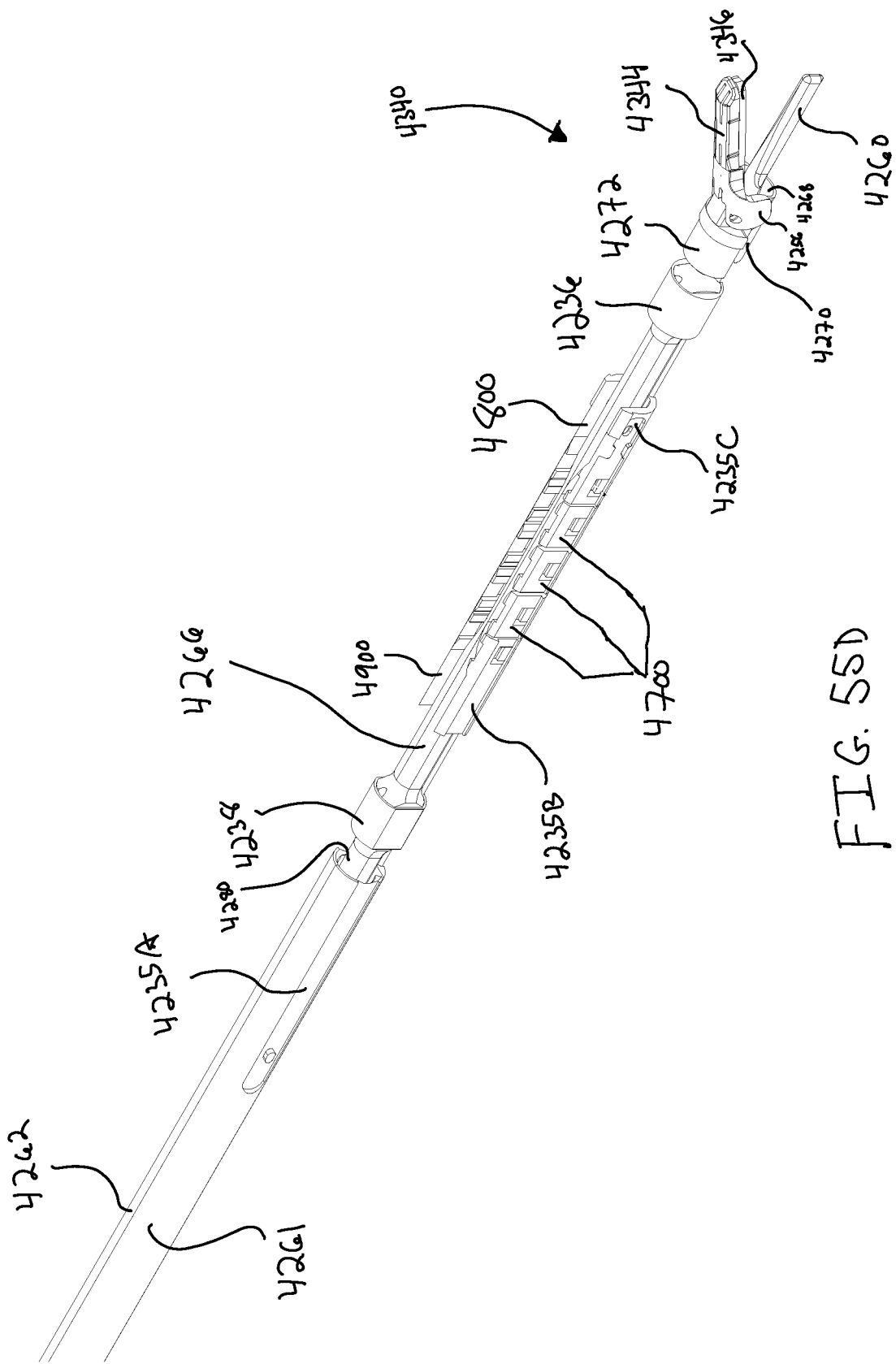
FIG. 55D depicts a perspective view of the articulation section of the shaft assembly and the end effector of FIG. 55A with certain elements omitted to show greater detail.

FIGS. 55A-56 illustrate the assembly of articulation section (4230). As illustrated in FIGS. 55D, 56, and 61, body portions (4700, 4800, 4900) are longitudinally aligned with one another between flanges (4236, 4238). In the present example, body portions (4700, 4800, 4900) are formed as discrete pieces positioned adjacent to each other, thereby promoting lateral flexing of articulation section (4230). Alternatively, body portions (4700, 4800, 4900) may be joined together by living hinges or any other structures that provide lateral flexing of articulation section (4230) as will be apparent to those of ordinary skill in the art in view of the teachings herein. In the current example, there is one proximal body portion (4900), three intermediate body portions (4700), and one distal body portion (4800). Of course, any suitable number of intermediate body portions (4700) may be provided.

As illustrated in FIGS. 55C and 56, body portions (4700, 4800, 4900) also partially define a channel (4235B, 4235C) that is configured to receive articulation band (4440) while allowing articulation band (4440) to slide relative to proximal body portion (4900) and intermediate body portions (4700). Unlike the previously mentioned articulation section (130), articulation bands (4440, 4442) are fixed to distal body portion (4800) rather than distal flange (4236). Because of this, distal flange (4236) does not require features, such as flats (192) to accommodate articulation bands (4440, 4442). Additionally, the shortened distance of articulation bands (4440, 4442) provides a user with greater control of articulation. During longitudinal deflection, more force is required from the shortened length of articulation bands (4440, 4442) to provide an equivalent moment as provided by longer articulation bands (140, 142). Therefore, a user has more tolerance control of the articulation angle due to the greater force required with shorter articulation bands (4440, 4442) than longer articulation bands (140, 142).

As illustrated in FIG. 55B, Proximal body portion (4900) is located within distal mating feature (4332A) of proximal outer sheath (4332) while distal body portion (4800) is located within proximal mating feature (4333A) of distal outer sheath (4333). Intermediate body portions (4700) are located in between proximal outer sheath (4332) and distal outer sheath (4333). More specifically, insert holes (4515) are located directly above leg channels (4740, 4840, 4940) of body portions (4700, 4800, 4900) in order to provide an insertion pathway for resilient legs (4625) of flexible locking feature (4600). In other words, retention collars (4500) are located at longitudinal positions corresponding to intermediate body portions (4700) while proximal mating feature (4333A) and distal mating feature (4332A) are located at longitudinal positions corresponding to distal body portion (4800) and proximal body portion (4900) respectively. Additionally, resilient tab (4885) of distal body portion (4800) is sized to fit within coupling features (4338) of distal outer sheath (4333), thereby ensuring distal body portion (4800) is fixed relative to distal outer sheath (4333). Of course, a similar feature can be added to proximal body portion (4900) to ensure sufficient attachment to proximal outer sheath (4332).

Figure 67:
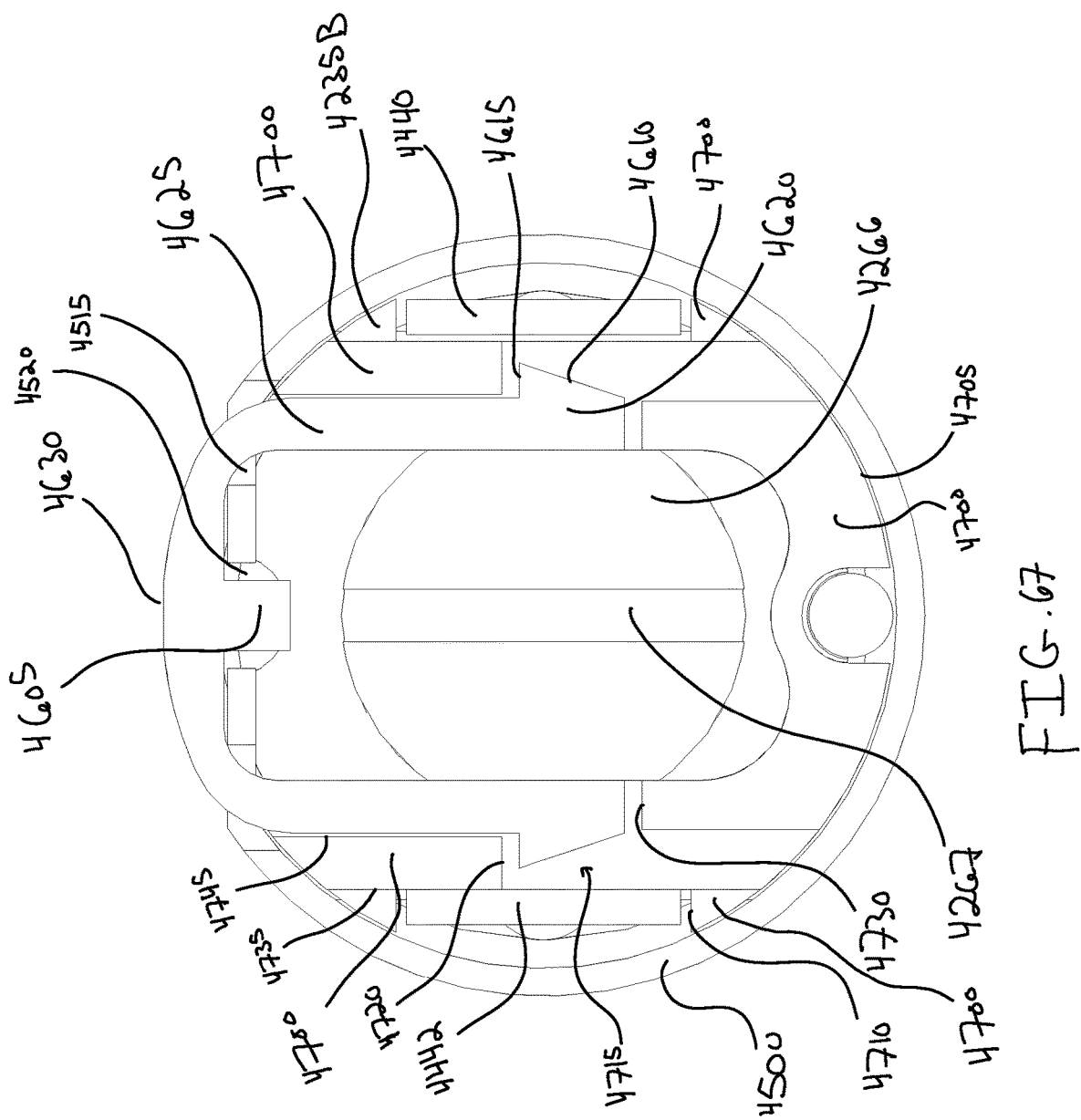
FIG. 67 depicts a cross sectional view of the articulation section of FIG. 55A across the intermediate body portion.

As illustrated in FIGS. 55A and 67-68, flexible locking feature (4600) is inserted into distal mating feature (4332A), retention collars (4500), proximal mating feature (4333A), proximal body portion (4900), intermediate body portions (4700), and distal body portion (4800). Flexible locking feature (4600) unitarily couples distal mating feature (4332A), retention rings (4500), and proximal mating feature (4333A) with proximal body portion (4900), intermediate body portions (4700), and distal body portion (4800) respectively. This coupling can be seen in greater detail in FIG. 67. When tabs (4620) of resilient legs (4625) are first inserted into insert holes (4515), resilient legs (4625) must be compressed inwardly to accommodate transverse surface (4615). Contact between interior tab contact surface (4745) and tab (4620) keeps resilient legs (4625) in a compressed position. Once transverse surface (4615) passes interior tab contact surface (4745) to tab window (4715), resilient legs (4625) transition from a compressed state to an original state substantially parallel with each other. Tab (4620) then enters through tab window (4715). At this point, flexible locking member (4600) is locked in place through a snap fit due to overlapping dimensions of tab ceiling (4720) and transverse surface (4615). Rib (4605) is now located within pathway (4520) of retention collar (4500). No object is in contact with the narrow section of waveguide (4267).

Due to the insertion of resilient legs (4625) into insert holes (4515) and leg channel (4740), retention collar (4500) is fixed along the longitudinal axis relative to intermediate body portions (4700). Similarly, due to the insertion of resilient legs (4625) into insert holes (4334) and leg channel (4840, 4940), proximal body portion (4900) and distal body portion (4800) are fixed along the longitudinal axis relative to distal mating feature (4332A) and proximal mating feature (4333A).

As mentioned before, the distal ends of articulation bands (4440, 4442) are unitarily secured to distal body portion (4800) via mating feature for articulation band (4890). When articulation bands (4440, 4442) translate longitudinally in an opposing fashion (e.g., one articulation band (4440) translating distally while the other articulation band (4442) simultaneously translates proximally), this will cause articulation section (4330) to bend due to creation of a moment applied to a distal end of distal outer sheath (4333) via upper distal shaft element (4272). The force provided by translation of articulation bands (4440, 4442) is communicated to distal body portion (4800) via a mating feature for articulation band (4890), which in turn is communicated to distal outer sheath (4333) via the connection of resilient tab (4885) of distal body portion (4800) and coupling feature (4338) of distal outer sheath (4333).

Figure 69A:
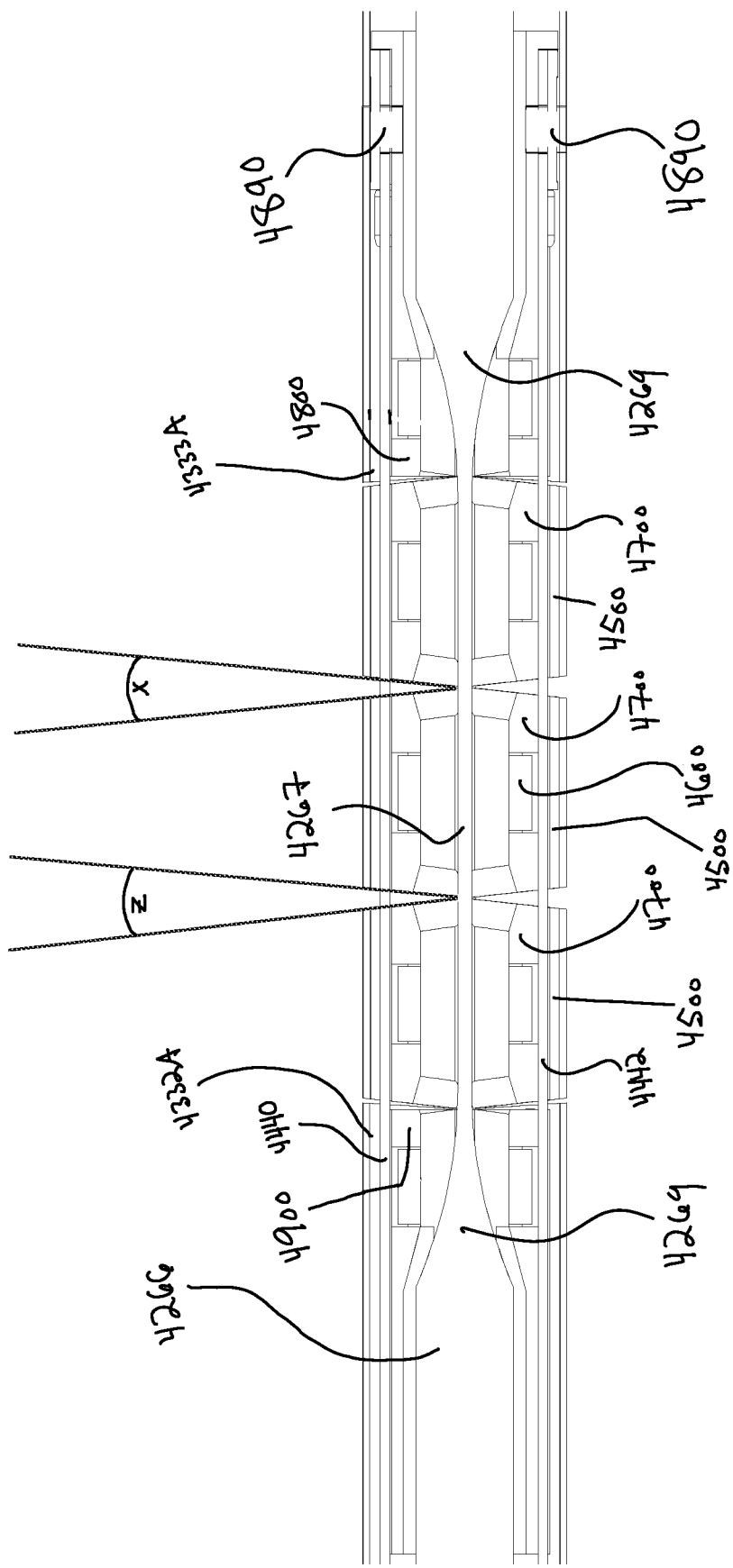
FIG. 69A depicts a cross sectional top view of the articulation section of the shaft assembly of the surgical instrument of FIG. 55A, with the articulation section in a non-articulated state.
Figure 69B:
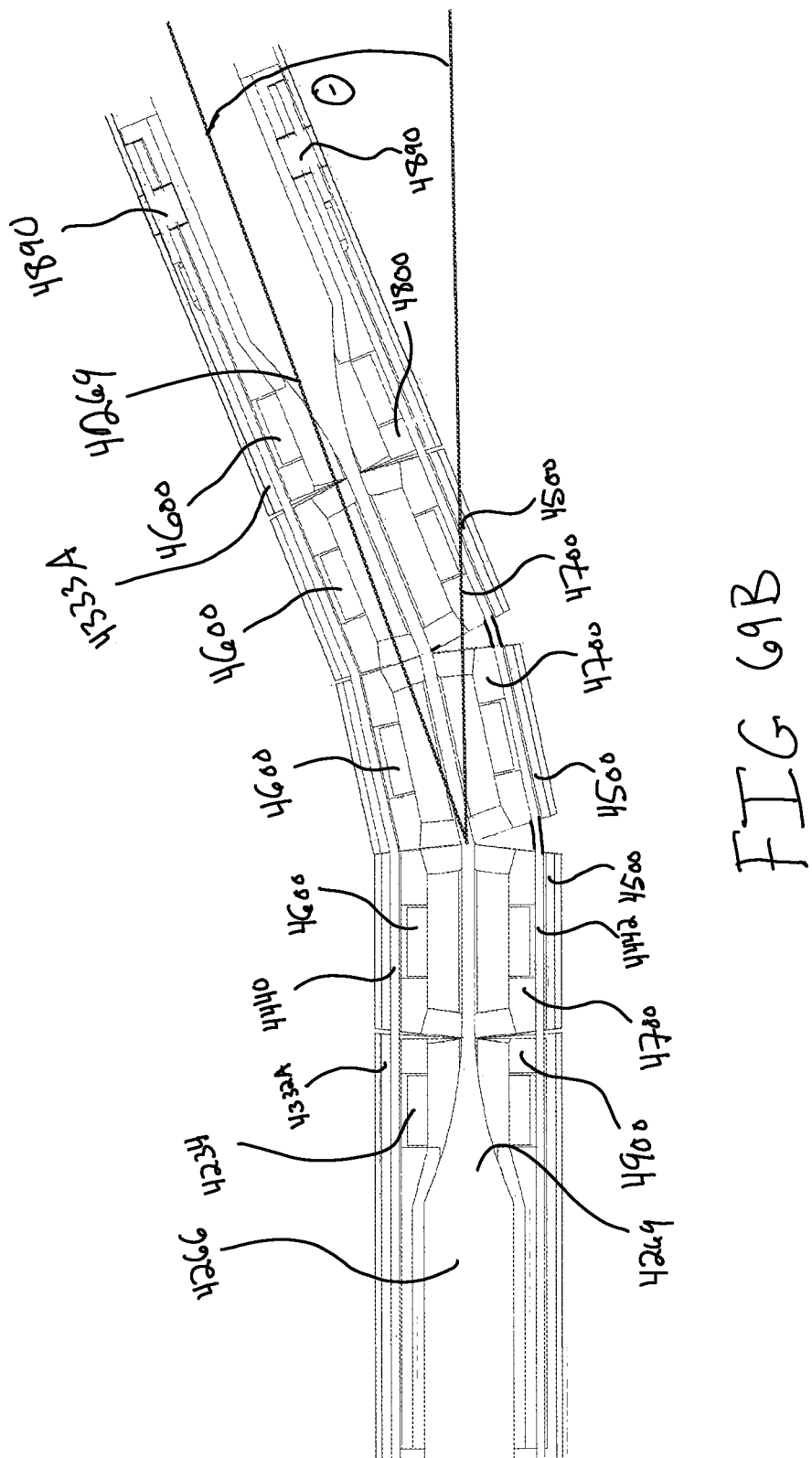
FIG. 69B depicts a cross sectional top view of the articulation section of the shaft assembly of the surgical instrument of FIG. 55A, with the articulation section in an articulated state.

Distal outer sheath (4333) is secured to waveguide (4280) at distal flange (4236), which is located at a position corresponding a node associated with resonant ultrasonic vibrations communicated through waveguide (4280). Therefore, the force required to bend waveguide (4280) for articulation is still communicated to waveguide (4280) at the nodal position of distal flange (4236), similar to waveguide (180). The bend thereby laterally deflects end effector (4340) away from the longitudinal axis of shaft assembly (4300) from a straight configuration as shown in FIGS. 68-69A to an articulated configuration as shown in FIG. 69B. In particular, end effector (4340) will be articulated toward the articulation band (4440, 4442) that is being pulled proximally. During such articulation, the other articulation band (4440, 4442) may be pulled distally by upper distal shaft element (4272). Alternatively, the other articulation band (4440, 4442) may be driven distally by an articulation control.

Flexible locking feature (4600) and narrowed section (4267) are sufficiently flexible to accommodate the above-described articulation of end effector (4340). Intermediate body portions (4700) and retention collars (4500) are able to articulate by moving relative to each other due to force provided by flexible locking feature (4600). Furthermore, flexible acoustic waveguide (4266) is configured to effectively communicate ultrasonic vibrations from waveguide (4280) to blade (4260) even when articulation section (4230) is in an articulated state as shown in FIG. 69B.

However, the flexible locking feature (4600) and the narrowed section (4267) are limited in articulation due to the geometry of retention collars (4500) and flexible locking element (4600). As best illustrated in FIG. 68, second angled contact surface (4525) of retention collar (4500) is dimensioned to allow a certain amount of clearance between articulation between rib (4605) of flexible locking member (4600) and retention collar (4500), thereby permitting articulation.

As best shown in FIG. 69A-B, first angled contact surface (4501) of one retention collar (4500) is dimensioned to abut against first angled contact surface (4501) of a second retention collar (4500), thereby providing a stop to limit articulation at a predetermined angle. As seen in FIG. 69A, angles X and Z are formed between first angled contact surfaces (4501) in an unarticulated position. While in this example, the angles X and Z are substantially similar, there is no requirement that the angles formed by first angled contact surfaces (4501) be identical. Alternatively, X could be twice the amount as Z, or X could be 0 degrees and Z could determine the entire articulation range. FIG. 69B shows articulation section (4230) in a maximum articulated state. First angled contact surfaces (4501) on one side of retention collars (4500) lock each other while the opposite side of first angled contact surfaces (4501) are further apart. Accordingly, the maximum articulation is limited to theta. In the present example, the maximum articulation angle is 30°.

Similar to articulation feature (130), articulation bands (4440, 4442) are laterally interposed within channels (4235B, 4235C) between retention collars (4500) and intermediate body portions (4700). Retention collars (4500) are configured to keep articulation bands (4440, 4442) in a parallel relationship with each other, particularly when articulation section (4330) is in a bent configuration (e.g., similar to the configuration shown in FIG. 69B). In other words, when articulation band (4440) is on the inner diameter of a curved configuration presented by a bent articulation section (4330), retention collars (4500) may retain articulation band (4440) such that articulation band (4440) follows a curved path that complements the curved path followed by articulation band (4442). It should be understood that channels (4235B, 4235C) are sized to accommodate respective articulation bands (4440, 4442) in such a way that articulation bands (4440, 4442) may still freely slide through articulation section (4330), even with retention collars (4500) being secured to intermediate body portions (4700). It should also be understood that retention collars (4500) may be secured to body portions (4700, 4800, 4900) in various ways, including but not limited to interference fitting, adhesives, welding, etc.

VIII. EXEMPLARY DISTAL FLANGE WITH CRUSH RIBS

Figure 70:
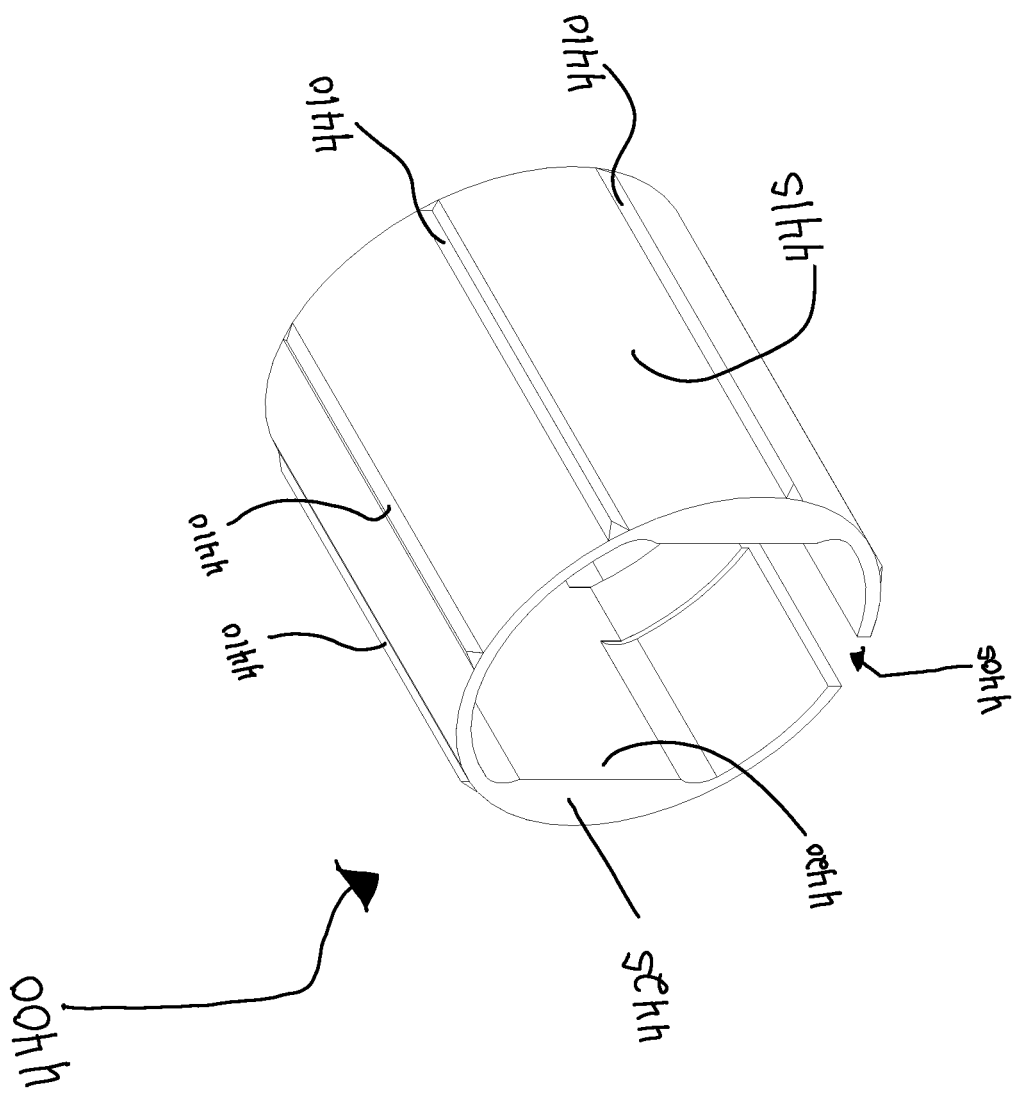
FIG. 70 depicts a perspective view of an exemplary distal node bumper that may be incorporated into the shaft assembly of FIG. 2.

In some instances it may be desirable for distal outer sheath (33, 4333) to be secured against distal flange (136, 4236) while maintaining minimal contact with distal flange (136, 4236). Minimal contact between distal outer sheath (33, 4333) and distal flange (136, 4236) may be desirable in order to limit the amount energy absorbed by outer sheath (33, 4333) in order to maintain a structurally secured connection between distal outer sheath (33, 4333) and distal flange (136, 4236). To that end, FIGS. 70-71 show an exemplary distal node bumper (4400) that may be used to secure distal outer sheath (33, 4333) to distal flange (136, 4236).

Distal node bumper (4400) of the present example is formed of an elastomeric material (e.g., silicone, etc.) and comprises a pair of flats (4420), a slot (4405), an outer surface (4415), crush ribs (4410) longitudinally disposed on surface (4415), and a face (4425). Flats (4420) complement flats of distal flange (136), thereby ensuring a secure connection between distal node (136) and distal node bumper (4400). Slot (4405) allows space for cable (174) to pass through distal node bumper (4400). Crush ribs (4410) are resilient, but compress within distal outer sheath (33) in order to provide a secure connection between distal flange (136) and distal outer sheath (33). Crush ribs (4410) also provide limited contact between distal flange (136) and distal outer sheath (33), thereby transferring minimal ultrasonic vibration energy to distal outer sheath (33), helping maintain a structurally secured connection between distal outer sheath (33) and distal flange (136).

IX. WAVEGUIDE WITH KEYHOLE CROSS SECTIONAL PROFILE

In some instances, articulation of waveguide (180, 4280) might lead to varied location of interaction between clamp pad (46, 4346) and blade (60, 4260) about the longitudinal axis when clamp pad (46, 4346) is in a closed position. For instance, when the articulation section (130, 4230) is in a non-articulated state, and clamp pad (46, 4346) is pivoted toward and away from blade (60, 4260), clamp pad (46, 4346) may traverse a vertically oriented path that is on-plane with a vertical plane that laterally bisects blade (60, 4260).

In some instances when the articulation section (130, 4320) is in an articulated state, and clamp pad (46, 4346) is pivoted toward and away from blade (60, 4260), clamp pad (46, 4346) may traverse an obliquely oriented path that is off-plane with a vertical plane that laterally bisects blade (60, 4260). In other words, the path that is traversed by clamp pad (46, 4346) may be obliquely oriented relative to a vertical plane that laterally bisects blade (60, 4260). This may be caused by a tolerance stack in the shaft assembly (30, 4300) and/or due to other factors. If this occurs to a blade that has a radius that varies along the surface range at which clamp pad (46, 4346) may compress tissue, such off-plane closure of clamp pad (34, 4346) may result in a compression force profile on the tissue that differs from the compression force profile that would be encountered by the tissue when clamp pad (46, 4346) is closed on-plane with articulation section (130, 4230) in a non-articulated state. In other words, the compression force profile on the tissue may vary based on whether articulation section (130, 4230) in an articulated state or a non-articulated state. For instance, such variation may lead to different times required to cut and/or seal tissue (e.g., by denaturing proteins in tissue cells). This inconsistency may cause an operator to expose blade (60, 4260) to direct contact with clamp pad (46, 4346) for a longer amount of time than desired. Direct contact between blade (60, 4260) and clamp pad (46, 4346) could lead to higher operating temperatures, possibly leading to deformation of blade (60, 4260) and/or clamp pad (46, 4346). It may therefore be desirable to prevent such variance in the compression force profile, thereby providing an end effector that provides a more consistent and predictable performance.

One method of providing uniform times for cutting and/or sealing is to use a blade (5000) with a keyhole cross sectional area, as shown in FIGS. 72-74. Blade (1000) of this example comprises a clamping surface (5003), an elongated surface (5002), and a back-cutting surface (5001). Clamping surface is substantially circular in shape, with a constant radius of curvature, and with a circumference large enough to prevent clamp pad (46) from clamping tissue on any other surface of blade (5000). By way of example only, the constant radius of curvature may extend for at least 180° of the cross-sectional area of blade (5000), or more particularly for at least 270° of the cross-sectional area of blade (5000), or more particularly for at least 320° of the cross-sectional area of blade (5000). Since clamping surface is substantially circular in shape, the tissue (6000) surface area exposed to blade (5000) is uniform regardless of articulation location, and regardless of whether clamp pad (46) is on-plane or off-plane with blade (5000) during closure. Elongated surface (5002) is relatively thin compared to clamping surface (5003). Elongated surface (5002) also extends from the bottom of clamping surface (5003). The shape and location of elongated surface (5002) ensures elongated surface (5002) will not come into contact with tissue (6000) clamped between clamp pad (46) and blade (5000). Back-cutting surface (5001) is located furthest away from clamp pad (46). Back-cutting surface (5001) is operable to cut and/or seal tissue (e.g., by denaturing proteins in tissue cells) without clamping tissue beforehand. It should also be understood that back-cutting surface (5001) may be used to perform back-cutting on tissue.

X. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus for operating on tissue, the apparatus comprising: (a) a body assembly; (b) a shaft extending distally from the body assembly, wherein the shaft defines a longitudinal axis; (c) an acoustic waveguide, wherein the waveguide comprises a flexible portion; (d) an articulation section coupled with the shaft, wherein a portion of the articulation section encompasses the flexible portion of the waveguide, wherein the articulation section further comprises: (i) a first member, and (ii) a second member, wherein the second member is longitudinally translatable relative to the first member; (e) an end effector comprising: (i) an ultrasonic blade in acoustic communication with the waveguide, and (ii) a clamp arm, wherein the clamp arm is coupled with the first member and the second member; and (f) an articulation drive assembly operable to drive articulation of the articulation section to thereby deflect the end effector from the longitudinal axis.

Example 2

The apparatus of Example 1 or any of the following Examples, wherein the articulation section includes a collar, wherein an upper portion of the collar is defined by the first member, wherein a lower portion of the collar is defined by the second member.

Example 3

The apparatus of any of the preceding or following Examples, further comprising at least one translatable member secured to the first member.

Example 4

The apparatus of Example 3, wherein the at least one translatable member is operable to translate to thereby drive articulation of the articulation section.

Example 5

The apparatus of Example 3, wherein the at least one translatable member comprises a band.

Example 6

The apparatus of any of the preceding or following Examples, further comprising at least one translatable member secured to the second member.

Example 7

The apparatus of Example 6, wherein the at least one translatable member is operable to translate to thereby drive the clamp arm toward and away from the ultrasonic blade

Example 8

The apparatus of Example 6, wherein the at least one translatable member comprises a drive cable.

Example 9

The apparatus of any of the preceding or following Examples, wherein the articulation section further comprises an outer tube engaged with the first member

Example 10

The apparatus of any of the preceding or following Examples, wherein the articulation section comprises a set of ribs separated by gaps configured to promote flexing of the articulation section.

Example 11

The apparatus of any of the preceding or following Examples, wherein the articulation drive assembly comprises a pair of translating members, wherein the translating members are operable to translate simultaneously in opposite directions to thereby deflect the end effector from the longitudinal axis.

Example 12

The apparatus Example 11, wherein the translating members are further operable to translate simultaneously in the same direction to thereby drive the clamp arm toward and away from the ultrasonic blade.

Example 13

The apparatus of Example 11, wherein the waveguide includes at least one flange defining a pair of flats, wherein the translating members are positioned at respective flats of the pair of flats.

Example 14

The apparatus of any of the preceding or following Examples, wherein the articulation drive assembly comprises at least one rotating member, wherein the rotating member is configured to rotate to thereby cause articulation of the articulation section.

Example 15

The apparatus of Example 14, wherein the articulation drive assembly further comprises a first translating articulation driver and a second translating articulation driver, wherein the first and second translating articulation drivers are translatable to cause articulation of the articulation section, wherein the first translating articulation driver and the second translating articulation driver are coupled with the at least one rotating member.

Example 16

The apparatus of Example 15, wherein the rotating member is rotatable in a single direction to thereby cause translation of the first translating articulation driver in a first direction and simultaneous translation of the second translating articulation driver in a second direction.

Example 17

The apparatus of Example 14, wherein the articulation drive assembly further comprises a locking assembly configured to selectively lock a rotational position of the rotating member.

Example 18

The apparatus of any of the preceding or following Examples, wherein the clamp arm engages the first member in a ball-and-socket configuration.

Example 19

An apparatus for operating on tissue, the apparatus comprising: (a) a body assembly; (b) a shaft extending distally from the body assembly, wherein the shaft defines a longitudinal axis; (c) an articulation section coupled with the shaft; (d) an end effector coupled with the articulation section, wherein the end effector comprises: (i) a working element configured to engage tissue, and (ii) a clamp arm operable to pivot toward and away from the working element; and (e) an articulation drive assembly operable to drive articulation of the articulation section to thereby deflect the end effector from the longitudinal axis, wherein the articulation drive assembly comprises: (i) a first translating driver, and (ii) a second translating driver, wherein the first and second translating drivers are operable to translate simultaneously in opposite directions to thereby deflect the end effector from the longitudinal axis, wherein the first and second translating drivers are operable to translate simultaneously in the same direction to thereby drive the clamp arm toward and away from the working element.

Example 20

An apparatus for operating on tissue, the apparatus comprising: (a) a body assembly; (b) a shaft extending distally from the body assembly, wherein the shaft defines a longitudinal axis; (c) an articulation section coupled with the shaft; (d) an end effector coupled with the articulation section, wherein the end effector comprises: (i) a working element configured to engage tissue, and (ii) a clamp arm operable to pivot toward and away from the working element; and (e) a first pair of translating members, wherein the first pair of translating members is operable to actuate the articulation section to thereby deflect the end effector from the longitudinal axis; (f) a second pair of translating members, wherein the second pair of translating members is operable to drive the clamp arm toward and away from the working element; and (g) an idler configured to provide coordinated opposing longitudinal movement of the second pair of translating members in response to deflection of the end effector from the longitudinal axis.

Example 21

An apparatus comprising: (a) a body assembly; (b) a shaft extending distally from the body assembly, wherein the shaft defines a longitudinal axis; (c) an acoustic waveguide, wherein the waveguide comprises a flexible portion; (d) an articulation section coupled with the shaft, wherein a portion of the articulation section encompasses the flexible portion of the waveguide, wherein the articulation section further comprises: (i) a plurality of body portions aligned along the longitudinal axis, and (ii) a flexible locking member, wherein the flexible locking member is operable to secure the body portions in relation to each other and in relation to the shaft; (e) an end effector comprising an ultrasonic blade in acoustic communication with the waveguide; and (f) an articulation drive assembly operable to drive articulation of the articulation section to thereby deflect the end effector from the longitudinal axis.

Example 22

The apparatus of Example 21 or any of the following Examples, wherein the articulation section includes at least one collar disposed around at least one body portion of the plurality of body portions.

Example 23

The apparatus of Example 22, wherein the at least one collar further comprises an angled surface configured to mechanically stop the flexible locking member from articulation past a predetermined angle.

Example 24

The apparatus of Example 22, wherein the flexible locking member further comprises an insert, wherein the at least one collar further comprises a path configured to receive the insert.

Example 25

The apparatus of any of the preceding or following Examples, wherein the articulation drive assembly comprises at least one translatable member engaged with least one body portion of the plurality of body portions.

Example 26

The apparatus of Example 25, wherein the at least one translatable member is operable to translate to thereby drive articulation of the articulation section.

Example 27

The apparatus of Example 25, wherein the at least one translatable member comprises a first band.

Example 28

The apparatus of Example 27, wherein the band is slidably disposed within or along at least one body portion of the plurality of body portions.

Example 29

The apparatus of Example 28, wherein the band is fixed a distal-most body portion of the plurality of body portions.

Example 30

The apparatus of Example 27, wherein the at least one translatable member further comprises a second band.

Example 31

The apparatus of Example 30, wherein both bands are slidably disposed within or along at least one body portion of the plurality of body portions.

Example 32

The apparatus of Example 31, wherein the first band and the second band are fixed to opposite sides of a distal-most body portion of the plurality of body portions.

Example 33

The apparatus of Example 32, wherein the first band and the second band are operable to simultaneously translate in opposing longitudinal directions.

Example 34

The apparatus of any of the preceding or following Examples, wherein shaft comprises a distal outer sheath located along the longitudinal axis, wherein the distal outer sheath comprises a proximal end and a distal end, wherein the proximal end of the distal outer sheath is connected to both the flexible locking member and a distal-most body portion of the plurality of body portions.

Example 35

The apparatus of Example 34, wherein the shaft further comprises a proximal outer sheath having a proximal end connected to the body assembly and a distal end, wherein the distal end is of the proximal outer sheath is connected to both the flexible locking member and a proximal-most body portion of the plurality of body portions.

Example 36

The apparatus of Example 35, wherein the flexible locking member further comprises at least two sets of resilient legs with a tab at the end of each leg.

Example 37

The apparatus of Example 36, wherein one set of resilient legs with a tab at the end of each leg is configured to connect the distal-most body portion of the plurality of body portions with the proximal end of the distal outer sheath.

Example 38

The apparatus of Example 36, wherein one set of resilient legs with a tab at the end of each leg is configured to connect the proximal-most body portion of the plurality of body portions with the distal end of the proximal outer sheath.

Example 39

An apparatus for operating on tissue, the apparatus comprising: (a) a body assembly; (b) a shaft extending distally from the body assembly, wherein the shaft defines a longitudinal axis; (c) an articulation section coupled with the shaft; (d) an end effector coupled with the articulation section, wherein the end effector comprises: (i) a working element configured to engage tissue, wherein the working element comprises keyhole cross sectional area, wherein the keyhole cross-sectional area is defined by: (A) a bottom cutting surface, and (B) a clamping surface having a constant radius of curvature, wherein the constant radius of curvature extends along at least 180° of an angular extent of the keyhole cross-sectional area, and (ii) a clamp arm operable to pivot toward and away from the clamping surface of the working element; and (e) an articulation drive assembly operable to drive articulation of the articulation section to thereby deflect the end effector from the longitudinal axis.

Example 40

An apparatus for operating on tissue, the apparatus comprising: (a) a body assembly; (b) a shaft extending distally from the body assembly, wherein the shaft defines a longitudinal axis, wherein the shaft includes a sheath; (c) an acoustic waveguide, wherein the waveguide comprises: (i) a proximal flange, (ii) a distal flange, and (iii) a flexible portion positioned between the proximal and distal flanges; (d) an articulation section coupled with the shaft, wherein a portion of the articulation section encompasses the flexible portion of the waveguide, wherein the articulation section further comprises: (i) a plurality of body portions aligned along the longitudinal axis, and (ii) a flexible locking member coupling the body portions with the shaft; (e) a bumper interposed between the distal flange of the waveguide and the sheath, wherein the bumper includes a plurality of longitudinally extending crush ribs; (f) an end effector comprising an ultrasonic blade in acoustic communication with the waveguide; and (g) an articulation drive assembly operable to drive articulation of the articulation section to thereby deflect the end effector from the longitudinal axis.

XI. MISCELLANEOUS

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Moreover, those of ordinary skill in the art will recognize that various teachings herein may be readily applied to electrosurgical instruments, stapling instruments, and other kinds of surgical instruments. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for operating on tissue, the apparatus comprising:
   (a) a shaft extending distally from the body assembly, wherein the shaft defines a longitudinal axis;
   (b) an acoustic waveguide, wherein the waveguide comprises a flexible portion, wherein at least the flexible portion of the acoustic waveguide is a single, unitarily formed structure;
   (c) an articulation section coupled with the shaft, wherein a portion of the articulation section is associated with the flexible portion of the waveguide, wherein the articulation section further comprises:
      (i) a first member, and
      (ii) a second member, wherein the second member is longitudinally translatable relative to the first member;
   (d) an end effector comprising:
      (i) an ultrasonic blade in acoustic communication with the waveguide, wherein the ultrasonic blade longitudinally and rigidly projects relative to the articulation section and is configured to cut tissue transversely thereagainst, and
      (ii) a clamp arm, wherein the clamp arm is coupled with the first member and the second member; and
   (e) an articulation drive assembly operable to drive articulation of the articulation section to thereby deflect the end effector from the longitudinal axis,
   the articulation drive assembly comprises a pair of translating members, wherein the translating members are operable to translate simultaneously in opposite directions to thereby deflect the end effector from the longitudinal axis, and
   wherein the translating members are further operable to translate simultaneously in the same direction to thereby drive the clamp arm toward and away from the ultrasonic blade.

2. The apparatus of claim 1, wherein the articulation section includes a collar.

3. The apparatus of claim 1, further comprising at least one translatable member secured to the first member.

4. The apparatus of claim 3, wherein the at least one translatable member is operable to translate to thereby drive articulation of the articulation section.

5. The apparatus of claim 3, wherein the at least one translatable member comprises a band.

6. The apparatus of claim 1, further comprising at least one translatable member secured to the second member.

7. The apparatus of claim 6, wherein the at least one translatable member is operable to translate to thereby drive the clamp arm toward and away from the ultrasonic blade.

8. The apparatus of claim 6, wherein the at least one translatable member comprises a drive cable.

9. The apparatus of claim 1, wherein the articulation section further comprises an outer tube engaged with the first member.

10. The apparatus of claim 1, wherein the articulation section comprises a set of ribs separated by gaps configured to promote flexing of the articulation section.

11. The apparatus of claim 1, wherein the waveguide includes at least one flange defining a pair of flats, wherein the translating members are positioned at respective flats of the pair of flats.

12. The apparatus of claim 1, wherein the articulation drive assembly comprises at least one rotating member, wherein the rotating member is configured to rotate to thereby cause articulation of the articulation section.

13. The apparatus of claim 12, wherein the articulation drive assembly further comprises a first translating articulation driver and a second translating articulation driver, wherein the first and second translating articulation drivers are translatable to cause articulation of the articulation section, wherein the first translating articulation driver and the second translating articulation driver are coupled with the at least one rotating member.

14. The apparatus of claim 13, wherein the rotating member is rotatable in a single direction to thereby cause translation of the first translating articulation driver in a first direction and simultaneous translation of the second translating articulation driver in a second direction.

15. The apparatus of claim 12, wherein the articulation drive assembly further comprises a locking assembly configured to selectively lock a rotational position of the rotating member.

16. The apparatus of claim 1, wherein the clamp arm engages the first member in a ball-and-socket configuration.

17. An apparatus for operating on tissue, the apparatus comprising:
- (a) a shaft defining a longitudinal axis;
- (b) an articulation section coupled with the shaft;
- (c) an end effector coupled with the articulation section, wherein the end effector comprises:
  - (i) a working element distally and rigidly projecting relative to the articulation section in an extended state and configured to engage tissue in the extended state, and
  - (ii) a clamp arm operable to pivot toward and away from the working element in the extended state; and
- (d) an articulation drive assembly operable to drive articulation of the articulation section to thereby deflect the end effector from the longitudinal axis, wherein the articulation drive assembly comprises:
  - (i) a first translating driver, and
  - (ii) a second translating driver, wherein the first and second translating drivers are operable to translate simultaneously in opposite directions to thereby deflect the end effector from the longitudinal axis, wherein the first and second translating drivers are operable to translate simultaneously in the same direction to thereby drive the clamp arm toward and away from the working element.

18. An apparatus for operating on tissue, the apparatus comprising:
- (a) a shaft defining a longitudinal axis;
- (b) an articulation section coupled with the shaft;
- (c) an end effector coupled with the articulation section, wherein the end effector comprises:
  - (i) a working element distally and rigidly projecting relative to the articulation section in an extended state and configured to engage tissue in the extended state, and
  - (ii) a clamp arm operable to pivot toward and away from the working element in the extended state; and
- (d) a first pair of translating members, wherein the first pair of translating members is operable to actuate the articulation section to thereby deflect the end effector from the longitudinal axis;
- (e) a second pair of translating members, wherein the second pair of translating members is operatively connected to the clamp arm and operable to drive the clamp arm toward and away from the working element; and
- (f) an idler operatively connected between each of the second pair of translating members and configured to provide coordinated opposing longitudinal movement of the second pair of translating members in response to deflection of the end effector from the longitudinal axis.

* * * * *

UNITED STATES PATENT AND TRADEMARK OFFICE
CERTIFICATE OF CORRECTION

| | |
|---|---|
| PATENT NO. | : 10,667,835 B2 |
| APPLICATION NO. | : 14/688692 |
| DATED | : June 2, 2020 |
| INVENTOR(S) | : William B. Weisenburgh, II et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1192 days.

Signed and Sealed this
Seventh Day of February, 2023

Katherine Kelly Vidal
*Director of the United States Patent and Trademark Office*